(12) United States Patent
Meghani et al.

(10) Patent No.: US 6,969,713 B2
(45) Date of Patent: Nov. 29, 2005

(54) PIPERIDINE AND PIPERAZINE ACETAMIDE DERIVATIVES

(75) Inventors: Premji Meghani, Loughborough (GB); Colin Bennion, Loughborough (GB)

(73) Assignee: AstraZeneca AB, Sodertalje (SE)

(*) Notice: Subject to any disclaimer, the term of this patent is extended or adjusted under 35 U.S.C. 154(b) by 160 days.

(21) Appl. No.: 10/168,094

(22) PCT Filed: Dec. 18, 2000

(86) PCT No.: PCT/SE00/02580

§ 371 (c)(1), (2), (4) Date: Jun. 17, 2002

(87) PCT Pub. No.: WO01/46200

PCT Pub. Date: Jun. 28, 2001

(65) Prior Publication Data

US 2003/0013721 A1 Jan. 16, 2003

(30) Foreign Application Priority Data

Dec. 22, 1999 (SE) .............................................. 9904738

(51) Int. Cl.[7] ................... C07D 401/12; C07D 403/12; C07D 403/14; A61K 31/496
(52) U.S. Cl. ............... 514/235.8; 514/249; 514/252.12; 514/252.14; 514/252.16; 514/252.17; 514/253.01; 514/253.07; 514/254.01; 514/254.04; 514/254.05; 514/255.03; 514/255.05; 514/316; 514/317; 514/330; 514/331; 544/121; 544/253; 544/255; 544/277; 544/349; 544/356; 544/357; 544/360; 544/363; 544/369; 544/370; 544/371; 544/372; 544/393; 546/189; 546/234
(58) Field of Search ............................... 514/235.8, 249, 514/252.12, 252.14, 252.16, 252.17, 253.01, 253.07, 254.01, 254.04, 254.05, 255.03, 255.05, 316, 317, 330, 331; 544/121, 253, 255, 277, 349, 356, 357, 360, 363, 369, 370, 371, 372, 393; 546/189, 234

(56) References Cited

U.S. PATENT DOCUMENTS

| | | | |
|---|---|---|---|
| 3,029,241 A | 4/1962 | Fancher et al. ............ 260/268 |
| 6,201,024 B1 | 3/2001 | Baxter et al. |
| 6,242,470 B1 | 6/2001 | Baxter et al. |
| 6,258,838 B1 | 7/2001 | Baxter et al. |
| 6,303,659 B2 | 10/2001 | Baxter et al. |
| 6,492,355 B1 | 12/2002 | Alcaraz et al. |
| 6,555,541 B1 | 4/2003 | Furber et al. |
| 6,720,452 B2 | 4/2004 | Alcaraz et al. |
| 6,812,226 B2 | 11/2004 | Baxter et al. |

FOREIGN PATENT DOCUMENTS

| | | | |
|---|---|---|---|
| EP | 0074768 A2 | 3/1983 |
| EP | 0582164 A1 | 2/1994 |
| FR | 2346011 A1 | 10/1977 |
| WO | WO 97/47601 A1 * | 12/1997 |
| WO | WO 99/31096 A1 | 6/1999 |
| WO | WO 99/59582 A1 | 11/1999 |
| WO | 01/44170 A1 | 6/2001 |

OTHER PUBLICATIONS

West, Anthony R., Solid State Chemistry and its Applications, Wiley, New York, 1988, pp. 358 & 365.*
Vera Ralevica and Geoffrey Burnstock, Pharmacological Reviews, vol. 50, Issue 3, 413–492, Sep. 1998.*
R. Alan North, Physiol. Rev. 82: 1013–1067, 2002.*
Chemical Abstracts, vol. 84, No. 9, Mar. 1, 1976, p. 527, The Abstract No. 59466u, JP 75108264A (Maruyama, Isamu et al.) Aug. 26, 1975.
Chemical Abstracts, vol. 57 (1962), Shin Hayao et al., "New sedative and hypotensive phenylpiperazine amides", The Abstract No. 3443i, J. Org. Chem. 1961, 26, 3414–3419.
STN International, File Caplus, Caplus accession No. 1995:324637, Document No. 122:105919, Kyowa Hakko Kogyo KK: Preparation of quinazolinylpiperazineacetamide derivatives; & JP A2, 06247942, 19940906.
STN International, File Caplus, Caplus accession No. 1991:656226, Document No. 115:256226, Kowa K.K., "Preparation of piperazine derivatives as antiarrhythmics", & JP, A2, 19910617.
Ferrari et al., "Purinergic Modulation of Interleukin–1β Release from Microglial Cells Stimulated with Bacterial Endotoxin", J. Exp. Med., 185 (3),. 1997, pp. 579–582.
Ferrari et al., "Extracellular ATP Triggers IL–1β Release by Activating the Purinergic P2Z Receptor of Human Macrophages", Journal of Immunology, 1997, 159(3), pp. 1451–1458.
Yu et al., "Inhibition of IL–1 Release from Hunan Monocytes and Suppression of Streptococcal Cell Wall and Adjuvant–induced Arthritis in Rats by an Extract of *Tripterygium wilfordii* Hook", General Pharmacology, 1994, 25(6), pp. 1115–1122.
Otterness et al., "Possible Role of IL–1 in Arthritis: Effects of Prostaglandins in the Regulation of IL–1 Synthesis and Actions", Joint Destruction in Arthritis and Osteoarthritis, Agents and Actions Supplements, 1993, 39, pp. 109–120.

(Continued)

*Primary Examiner*—Thomas C. McKenzie
(74) *Attorney, Agent, or Firm*—Morgan, Lewis & Bockius LLP

(57) ABSTRACT

The invention provides piperidine and piperazine derivatives of general formula (I), processes for their preparation, pharmaceutical compositions containing them, a process for preparing the pharmaceutical compositions, and their use in therapy

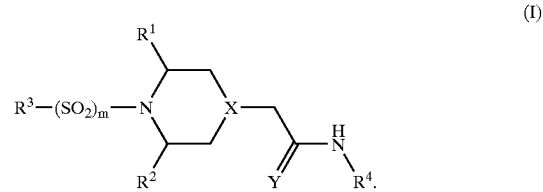

10 Claims, No Drawings

OTHER PUBLICATIONS

Henderson et al., "Inhibition of Interleukin–1–Induced Synovitis and Articular Cartilage Proteoglycan Loss in the Rabbit Knee by Recombinant Human Interleukin–1 Receptor Antagonist", Cytokine, 3(3), 1991, pp. 246–249.

Kodata et al., "Significance of IL–1β and IL–1 receptor antagonist (IL–1Ra) in bronchoalveolar lavage fluid (BALF) in patients with diffuse panbronchiolitis (DPB)", Clin Exp Immunol, 1996, 103, pp. 461–466.

Sakito et al., "Interleukin 1β, Tumor Necrosis Factor Alpha, and Interleukin 8 in Bronchoalveolar Lavage Fluid of Patients with Diffuse Panbronchiolitis: A Potential Mechanism of Macrolide Therapy", Respiration, 63, pp. 42–48.

* cited by examiner

PIPERIDINE AND PIPERAZINE ACETAMIDE DERIVATIVES

The present invention relates to piperidine and piperazine derivatives, processes for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells), hepatocytes, erythrocytes, erythroleukaemic cells, monocytes, fibroblasts, bone marrow cells, neurones and renal mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

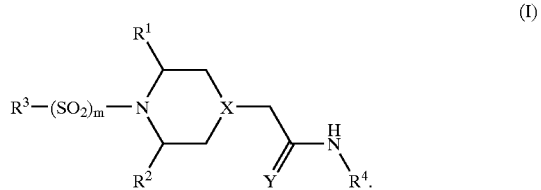

(I)

wherein,

X represents a nitrogen atom or a group $C(R^5)$;

Y represents an oxygen or sulphur atom or a group $NR^6$, preferably an oxygen atom;

either $R^1$ and $R^2$ each independently represent a hydrogen atom or a $C_1$–$C_4$ alkyl group but do not both simultaneously represent a hydrogen atom, or $R^1$ and $R^2$ together represent a group —$CH_2ZCH_2$—;

Z represents a bond, an oxygen or sulphur atom or a group $CH_2$ or $NR^7$, and is preferably a bond;

m is 0 or 1;

$R^3$ represents a 5- to 10-membered unsaturated ring system which may comprise from 1 to 4 ring heteroatoms independently selected from nitrogen, oxygen and sulphur, the ring system being optionally substituted by one or more substituents independently selected from halogen, nitro, cyano, $NR^8R^9$, $C_1$–$C_4$ alkyl-C(O)NH—, $NHR^{12}C(O)$—, $C_1$–$C_4$ alkyl-$SO_2$—, $C_1$–$C_4$ alkyl-$SO_2NH$—, $C_1$–$C_4$ alkyl-$NHSO_2$—, $C_1$–$C_4$ alkoxy, and $C_1$–$C_4$ alkyl optionally substituted by one or more fluorine atoms;

$R^4$ represents a phenyl or pyridinyl group, each of which is substituted in an ortho position with a substituent selected from halogen, $C_1$–$C_4$ alkoxy, $C_1$–$C_4$ alkylthio, and $C_1$–$C_4$ alkyl optionally substituted by one or more fluorine atoms, the phenyl or pyridinyl group being optionally further substituted by one or more substituents independently selected from halogen, cyano, hydroxyl, $C_1$–$C_4$ alkylthio, $C_1$–$C_4$ alkyl-NH—, $NHR^{13}$—$C_1$–$C_4$ alkyl-, $C_1$–$C_4$ alkyl-$SO_2$—, $C_1$–$C_4$ alkyl-$SO_2NH$—, $C_1$–$C_4$ alkyl-$NHSO_2$—, $C_1$–$C_4$ alkyl-C(O)NH—, $C_1$–$C_4$ alkyl-NHC(O)—, -D-G, $C_1$–$C_4$ alkoxy optionally substituted by —$NR^{14}R^{15}$ or by $R^{16}$, and $C_1$–$C_4$ alkyl optionally substituted by one or more fluorine atoms or by one or more hydroxyl groups, or $R^4$ represents a 9- or 10-membered unsaturated bicyclic ring system which may comprise from 1 to 4 ring heteroatoms independently selected from nitrogen, oxygen and sulphur, the bicyclic ring system being optionally substituted by one or more substituents independently selected from halogen, oxo, $C_1$–$C_4$ alkyl, $C_1$–$C_4$ alkoxy, $C_1$–$C_4$ alkylthio and —$NR^{10}R^{11}$;

D represents an oxygen atom or a group $(CH_2)_n$ or $CH_2NH$;

n is 1, 2 or 3;

G represents a piperazinyl, morpholinyl or 2,5-diazabicyclo[2.2.1]heptyl group, or G represents a piperidinyl group optionally substituted by amino (—$NH_2$);

$R^5$ represents a hydrogen atom, or a hydroxyl or $C_1$–$C_4$ alkoxy group;

$R^6$ represents a hydrogen atom, or a cyano, nitro, hydroxyl, $C_1$–$C_4$ alkyl or $C_1$–$C_4$ alkoxy group;

$R^7$, $R^8$ and $R^9$ each independently represent a hydrogen atom or a $C_1$–$C_4$ alkyl group;

$R^{10}$ and $R^{11}$ each independently represent a hydrogen atom or a $C_1$–$C_4$ alkyl group, or $R^{10}$ and $R^{11}$ together with the nitrogen atom to which they are attached form a 5- or 6-membered saturated heterocyclic ring comprising one or two ring nitrogen atoms;

$R^{12}$ represents a hydrogen atom, or a $C_1$–$C_4$ alkyl group optionally substituted by amino (—$NH_2$);

$R^{13}$ represents a hydrogen atom, or a $C_1$–$C_4$ alkyl group optionally substituted by hydroxyl;

$R^{14}$ and $R^{15}$ each independently represent a hydrogen atom or a $C_1$–$C_4$ alkyl group optionally substituted by hydroxyl, or $R^{14}$ and $R^{15}$ together with the nitrogen atom to which they are attached form a 5- or 6-membered saturated heterocyclic ring comprising one or two ring nitrogen atoms; and $R^{16}$ represents a 1-($C_1$–$C_4$-alkyl)-piperidinyl group;

with the proviso that when m is 0, X is N and Y is O, then $R^4$ does not represent 2-benzothiazolyl;

or a pharmaceutically acceptable salt or solvate thereof

In the context of the present specification, unless otherwise indicated, an alkyl substituent or alkyl moiety in a substituent group may be linear or branched. In the present invention, an alkyl group or moiety may contain up to 4 carbon atoms, for example, methyl, ethyl, propyl, isopropyl, butyl, isobutyl and t-butyl.

When the substituent group is $NHR^{13}$—$C_1$–$C_4$ alkyl-, it should be appreciated: that the $NHR^{13}$ moiety may be attached to a terminal or internal carbon atom of the alkyl moiety and when the substituent group is alkoxy substituted by —$NR^{14}R^{16}$, the alkoxy group will contain at least 2 carbon atoms and the group —$NR^{14}R^{15}$ is not attached to the same carbon atom to which the oxygen atom is attached.

$R^3$ represents a 5- to 10-membered unsaturated ring system which may comprise 1, 2, 3 or 4 ring heteroatoms independently selected from nitrogen, oxygen and sulphur, the ring system being optionally substituted by one or more (i.e. at least one), e.g. one, two or three, substituents independently selected from halogen (e.g. fluorine, chlorine, bromnine or iodine), nitro, cyano, $NR^8R^9$, $C_1$–$C_4$ alkyl-C(O)NH— (e.g. $CH_3C(O)NH$—), $NHR^{12}C(O)$— (e.g. $NH_2C(O)$—, $NH(CH_3)C(O)$—, $(CH_3)_2NC(O)$—, $NH_2CH_2CH_2NHC(O)$—), $C_1$–$C_4$ alkyl-$SO_2$— (e.g. $CH_3SO_2$—), $C_1$–$C_4$ alkyl-$SO_2NH$— (e.g. $CH_3SO_2NH$—), $C_1$–$C_4$ alkyl-$NHSO_2$— (e.g. $CH_3NHSO_2$—), $C_1$–$C_4$, preferably $C_1$–$C_2$, alkoxy, and $C_1$–$C_4$, preferably $C_1$–$C_2$, alkyl optionally substituted by one or more (i.e. at least one), e.g. one, two, three or four, fluorine atoms (e.g. trifluoromethyl). Specific substituents that may be mentioned include: methyl, amino (—NH$_2$), cyano, methoxy, chloro, nitro, NH$_2$C(O)—, CH$_3$C(O)NH—, CH$_3$SO$_2$—, CH$_3$SO$_2$NH— and NH$_2$CH$_2$CH$_2$NHC(O)—.

The ring system may be monocyclic or polycyclic. If polycyclic, e.g. bicyclic, the two rings may be fused to one another or may be joined by a bond. If the ring system is bicyclic, it is preferred that the rings are fused to one another. Examples of ring systems that may be used include phenyl, pyridinyl, pyrimidinyl, naphthyl, furanyl, pyrryl, thienyl, isothiazolyl, imidazolyl, benzimidazolyl, tetrazolyl, pyrazinyl, quinolinyl, isoquinolinyl, benzofuranyl, isobenzofuranyl, benzothienyl, pyrazolyl, indolyl, isoindolyl, purinyl, oxazolyl, isoxazolyl, thiazolyl, triazinyl, benzothiazolyl, benzooxazolyl, imidazopyrazinyl, triazolopyrazinyl, naphthyridinyl, furopyridinyl, thiopyranopyrimidinyl, pyridazinyl, quinazolinyl, pteridinyl, triazolopyrimidinyl, triazolopyrazinyl, thiapurinyl, oxapurinyl, deazapurinyl, thiazolopyrimidinyl, indolinyl, benzooxadiazolyl, benzothiadiazolyl, tetrahydroisoquinilinyl, 2-(isoxazol-3-yl)thienyl, and thienopyrimidinyl. Preferred ring systems are phenyl, thienopyrimidinyl, purinyl, pyrimidinyl, thiazolopyrimidinyl, quinazolinyl, benzooxadiazolyl, benzothiadiazolyl, thienyl, imidazolyl, tetrahydroisoquinilinyl, isoquinolinyl, pyrazolyl, isoxazolyl, 2-(isoxazol-3-yl)thienyl and pyridinyl.

R$^4$ may represent a phenyl or pyridinyl group comprising at least one substituent selected from halogen (e.g. fluorine, chlorine, bromine or iodine), C$_1$–C$_4$, preferably C$_1$–C$_2$, alkoxy, C$_1$–C$_4$, preferably C$_1$–C$_2$, alkylthio or C$_1$–C$_4$, preferably C$_1$–C$_2$, alkyl optionally substituted by one or more (i.e. at least one) fluorine atoms (e.g. trifluoromethyl), which substituent is attached to the phenyl or pyridinyl group at a position ortho (*) with respect to the point of attachment of R$^4$ to the rest of the molecule, for example as illustrated below. Examples of preferred ortho substituents include chloro, methyl and trifluoromethyl.

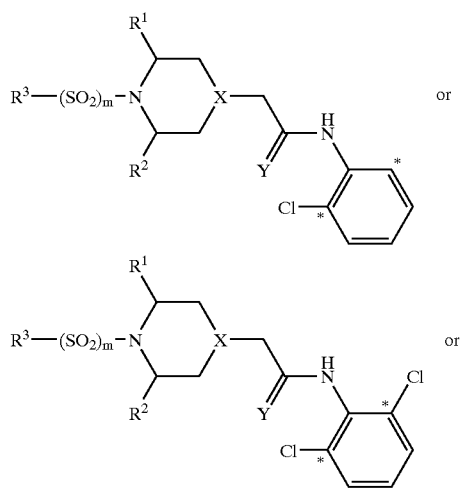

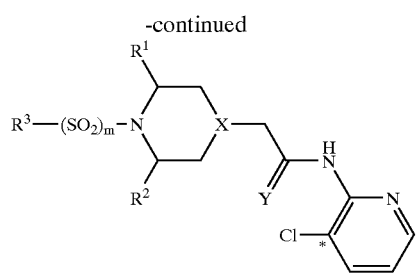

The phenyl or pyridinyl group may be optionally further substituted by one or more (i.e. at least one) (e.g. one, two, three or four) substituents independently selected from halogen (e.g. fluorine, chlorine, bromine or iodine), cyano, hydroxyl, C$_1$–C$_4$ alkylthio (e.g. methylthio or ethylthio), C$_1$–C$_4$ alkyl-NH— (e.g. methylamino or ethylamino), NHR$^{13}$—C$_1$–C$_4$ alkyl-, C$_1$–C$_4$, preferably C$_1$–C$_2$, alkyl-SO$_2$—, C$_1$–C$_4$, preferably C$_1$–C$_2$, alkyl-SO$_2$NH—, C$_1$–C$_4$, preferably C$_1$–C$_2$, alkyl-NHSO$_2$—, C$_1$–C$_4$, preferably C$_1$–C$_2$, alkyl-C(O)NH—, C$_1$–C$_4$, preferably C$_1$–C$_2$, alkyl-NHC(O)—, -D-G, C$_1$–C$_4$ alkoxy optionally substituted by —NR$^{14}$R$^{15}$ or by R$^{16}$, and C$_1$–C$_4$, preferably C$_1$–C$_2$, alkyl optionally substituted by one or more (i.e. at least one) fluorine atoms (e.g. trifluoromethyl) or by one or more (i.e. at least one) hydroxyl groups (e.g. hydroxymethyl).

Alternatively, R$^4$ may represent a 9- or 10-membered unsaturated fused bicyclic ring system which may comprise 1, 2, 3 or 4 ring heteroatoms independently selected from nitrogen, oxygen and sulphur, the ring system being optionally substituted by one or more (i.e. at least one) (e.g. one, two, three or four) substituents independently selected from halogen (e.g. fluorine, chlorine, bromine or iodine), oxo, C$_1$–C$_4$, preferably C$_1$–C$_2$, alkyl, C$_1$–C$_4$, preferably C$_1$–C$_2$, alkoxy, C$_1$–C$_4$, preferably C$_1$–C$_2$, alkylthio and NR$^{10}$R$^{11}$. Examples of suitable bicyclic ring systems include naphthyl, benzimidazolyl, quinolinyl, indolinyl, isoquinolinyl, benzofuranyl, isobenzofuranyl, benzothienyl, indolyl, isoindolyl, benzthiazolyl, benzoxazolyl and quinazolinyl. An example of an unsaturated fused bicyclic ring system substituted by an oxo group is oxindolyl.

D represents an oxygen atom or a group (CH$_2$)$_n$ or CH$_2$NH (in that orientation), where n is 1, 2 or 3.

G represents a piperazinyl, morpholinyl or 2,5-diazabicyclo[2.2.1]heptyl group, or G represents a piperidinyl group optionally substituted by at least one amino group (e.g. 1-piperidinyl, 4-piperidinyl, 1-piperazinyl, 1-morpholinyl or 4-amino-1-piperidinyl).

R$^5$ represents a hydrogen atom, or a hydroxyl or C$_1$–C$_4$ alkoxy group. In a preferred embodiment, R$^5$ represents a hydrogen atom.

R$^6$ represents a hydrogen atom, or a cyano, nitro, hydroxyl, C$_1$–C$_4$, preferably C$_1$–C$_2$, alkyl or C$_1$–C$_4$, preferably C$_1$–C$_2$, alkoxy group.

R$^7$, R$^8$ and R$^9$ each independently represent a hydrogen atom or a C$_1$–C$_4$, preferably C$_1$–C$_2$, alkyl group.

R$^{10}$ and R$^{11}$ each independently represent a hydrogen atom or a C$_1$–C$_4$, preferably C$_1$–C$_2$, alkyl group, or R$^{10}$ and R$^{11}$ together with the nitrogen atom to which they are attached form a 5- or 6-membered saturated heterocyclic ring comprising one or two ring nitrogen atoms (e.g. pyrrolidinyl, piperidinyl or piperazinyl).

R$^{12}$ represents a hydrogen atom, or a C$_1$–C$_4$, preferably C$_1$–C$_2$, alkyl group optionally substituted by at least one amino group (—NH$_2$).

$R^{13}$ represents a hydrogen atom, or a $C_1$–$C_4$, preferably $C_1$–$C_2$, alkyl group optionally substituted by at least one hydroxyl group.

$R^{14}$ and $R^{15}$ each independently represent a hydrogen atom or a $C_1$–$C_4$, preferably $C_1$–$C_2$, alkyl group optionally substituted by at least one hydroxyl group, or $R^{14}$ and $R^{15}$ together with the nitrogen atom to which they are attached form a 5- or 6-membered saturated heterocyclic ring comprising one or two ring nitrogen atoms (e.g. pyrrolidinyl, piperidinyl or piperazinyl).

$R^{16}$ represents a 1-($C_1$–$C_4$-alkyl)-piperidinyl group, e.g. 1-methylpiperidinyl, specifically 1-methylpiperidin-3-yl.

Preferred compounds of the invention include:

(±)-N-(2,6-Dimethylphenyl)-2-(3-methyl-4-(thieno[2,3-d]pyrimidin-4-yl)piperazin-1-yl)acetamide, cis-[2-(3,5-Dimethyl-4-(thieno[2,3-d]pyrimidin-4-yl)piperazin-1-yl)]-N-(2,6-dimethylphenyl)acetamide, (±)-2-[3-Methyl-4-(4-methylphenyl)piperazin-1-yl]-N-(2,6-dimethylphenyl)acetamide, cis-N-[3-Hydroxymethyl-2-methylphenyl]-2-(3,5-dimethyl-4-(thieno[2,3-d]pyrimidin-4-yl)piperazin-1-yl)acetamide, (R)-2-[4-(1-Methylimidazol-4-sulphonyl-4-yl)-3-ethylpiperazin-1-yl]-N-(quinolin-5-yl)acetamide, cis-2-[3,5-Dimethyl-4-(thieno[2,3-d]pyrimidin-4-yl)piperazin-1-yl]-N-(2-methylphenyl)acetamide, cis-N-(2-Chlorophenyl)-2-[3,5-dimethyl-4-(thieno[2,3-d]pyrimidin-4-yl)piperazin-1-yl]acetamide, cis-N-(2-Chlorophenyl)-2-[3,5-dimethyl-4-(9-methyl-9H-purin-6yl)piperazin-1-yl]acetamide, cis-2-(3,5-Dimethyl-4-(thieno[2,3-d]pyrimidin-4-yl)piperazin-1-yl)-N-(isoquinolin-5-yl)acetamide, cis-2-(3,5-Dimethyl-4-thieno[2,3-d]pyrimidin-4-yl)piperazin-1-yl)-N-(quinolin-5-yl)acetamide, cis-2-(3,5-Dimethyl-4-(thieno[2,3-d]pyrimidin-4-yl)piperazin-1-yl)-N-(2-methyl-5-methylsulphonamidophenyl)acetamide, cis-2-(3,5-Dimethyl-4-(thieno[2,3-d]pyrimidin-4-yl)piperazin-1-yl]-N-(2-trifluoromethylphenyl)acetamide, cis-2-(3,5-Dimethyl-4-(thieno[2,3-d]pyrimidin-4-yl)piperazin-1-yl)-N-(3-methylpyridin-2-yl)acetamide, cis-2-(3,5-Dimethyl-4-(thieno[2,3-d]pyrimidin-4-yl)piperazin-1-yl)-N-(isoquinolin-1-yl)acetamide, cis-4-(4-Amino-5-cyanopyrimidin-2-yl)-3,5-dimethylpiperazin-1-yl)-N-(2-chlorophenyl)acetamide, cis-2-(4-Benzenesulphonyl-3,5-dimethylpiperazin-1-yl)-N-(2-chlorophenyl)acetamide, (±)-N-(2,6-Dimethylphenyl)-2-[(3-methyl-4-thiazolo[5,4-d]pyrimidin-7-yl)piperazin-1-yl]acetamide, cis-N-(2-Chlorophenyl)-2-[(3,5-dimethyl-4-quinazolin-4-yl)piperazin-1-yl]acetamide, N-(2-Chlorophenyl)-2-[(8-(thieno[2,3-d]pyrimidin-4-yl)-3,8-diazabicyclo[3.2.1]oct-3-yl]acetamide, N-(2-Methylphenyl)-2-[8-(9-methyl-9H-purin-6-yl)-3,8-diazabicyclo[3.2.1]oct-3-yl]acetamide, 2-[8-(9-Methyl-9H-purin-6-yl)-3,8-diazabicyclo[3.2.1]oct-3-yl]-N-(quinolin-5-yl)acetamide, N-(Quinolin-5-yl)-2-[8-thiazolo[5,4-d]pyrimidin-7-yl)-3,8-diazabicyclo[3.2.1]oct-3-yl]acetamide, N-(2-Methylphenyl)-2-[(8-thiazolo[5,4-d]pyrimidin-7-yl)-3,8-diazabicyclo[3.2.1]oct-3-yl]acetamide, N-(2-Methyl-5-(methylsulphonyl)amidophenyl)-2-[8-(9-methyl-9H-purin-6-yl)-3,8-diazabicyclo[3.2.1]oct-3-yl]acetamide, N-[2-Methyl-5-(methylsulphonyl)amidophenyl]-2-[(8-thiazolo[5,4-d]pyrimidin-7-yl)-3,8-diazabicyclo[3.2.1]oct-3-yl]acetamide, N-[2-Methyl-5-(methylsulphonyl)amidophenyl]-2-[4-(thieno[2,3-d]pyrimidin-4-yl)-3,8-diazabicyclo[3.2.1]oct-3-yl]acetamide, cis-2-(3,5-Dimethyl-4-(thieno[2,3-d]pyrimidin-4-yl)piperazin-1-yl)-N-(2-methyl-5-(1-piperazinylmethyl)phenyl)acetamide, hydrochloride salt, N-(2-Methylphenyl)-2-[(8-(thieno[2,3-d]pyrimidin-4-yl)-3,8-diazabicyclo[3.2.1]oct-3-yl]acetamide, N-[5-(Methanesulphonylamido-2-methylphenyl)-2-[8-(thieno[2,3-d]pyrimidin-4-yl)-8-azabicyclo[3.2.1]oct-3-yl]acetamide, N-(2-Methyl-5-(1-piperazinylmethyl)phenyl)-2-[-(thieno[2,3-d]pyrimidin-4-yl)-3,8-diazabicyclo[3.2.1]oct-3-yl]acetamide, cis-N-(5-(2-Aminoethoxy)-2-methyl-phenyl)-2-(3,5-dimethyl-4-(thieno[2,3-d]pyrimidin-4-yl)piperazin-1-yl)acetamide, hydrochloride salt, cis-N-(5-(2-(N-Methylamio)ethoxy)-2-methyl-phenyl)-2-(3,5-dimethyl-4-(thieno[2,3-d]pyrimidin-4-yl)piperazin-1-yl)acetamide, hydrochloride salt, cis-N-(5-(2-(N-Methylamino)ethoxy)-2-methyl-phenyl)-2-(4-benzenesulphonyl)-3,5-dimethyl)piperazin-1-yl)acetamide, cis-N-[5-(2-Aminoethoxy)-2-methyl-phenyl)-2-(4-benzenesulphonyl-3,5-dimethyl)piperazin-1-yl]acetamide, hydrochloride salt, N-(2-Oxo-2,3-dihydro-1H-indol-4-yl)-2-(8-thieno[2,3-d]pyrimidin-4-yl-3,8-diazabicyclo[3.2.1]oct-3-yl)acetamide N-(3-Fluoro-2-methyl-phenyl)-2-((8-quinazolin-4-yl)-3,8-diazabicyclo[3.2.1]oct-3-yl)acetamide, N-(2-Methylphenyl)-2-[8-(benzenesulphonyl)-3,8-diazabicyclo[3.2.1]oct-3-yl]acetamide, N-(3-Fluoro-2-methylphenyl)-2-[8-(benzenesulphonyl)-3,8-diazabicyclo[3.2.1]oct-3-yl]acetamide, cis-N-(3-Fluoro-2-methyl-phenyl)-2-(4-benzenesulphonyl)-3,5-dimethyl)piperazin-1-yl)acetamide, N-(2-Methylphenyl)-2-[8-(3-cyanobenzenesulphonyl)-3,8-diazabicyclo[3.2.1]oct-3-yl]acetamide, 2-[8-(3-Methoxybenzenesulphonyl)-3,8-diazabicyclo[3.2.1]oct-3-yl]-N-(2-methylphenyl)acetamide, 2-[8-(Benzo[1,2,5]oxadiazole-4-sulphonyl)-3,8-diazabicyclo[3.2.1]oct-3-yl]-N-(2-methylphenyl)acetamide, 2-[8-(Benzo[1,2,5]thiadiazole-4-sulphonyl)-3,8-diazabicyclo[3.2.1]oct-3-yl]-N-(2-methylphenyl)acetamide, 2-[8-(5-Chlorothieno-2-yl)sulphonyl)-3,8-diazabicyclo[3.2.1]oct-3-yl]-N-(2-methylphenyl)acetamide, 2-[8-(2-Chlorobenzenesulphonyl)-3,8-diazabicyclo[3.2.1]oct-3-yl]-N-(2-methylphenyl)acetamide, 2-[8-(5-Chloro-2-methoxybenzenesulphonyl)-3,8-diazabicyclo[3.2.1]oct-3-yl]-N-(2-methylphenyl)acetamide, 2-[8-(4-Acetylaminomethoxybenzenesulphonyl)-3,8-diazabicyclo[3.2.1]oct-3-yl]-N-(2-methylphenyl)acetamide, N-(2-Methylphenyl)-2-[(8-(3-methylthieno[2,3-d]pyrimidin-4-yl)-3,8-diazabicyclo[3.2.1]oct-3-yl]acetamide, cis-2-(3,5-Dimethyl-4-(thieno[2,3-d]pyrimidin-4-yl)piperazin-1-yl)-N-(1-methyl-1H-benzoimidazol-2-yl)acetamide, cis-2-(3,5-Dimethyl-4-(thieno[2,3-d]pyrimidin-4-yl)piperazin-1-yl)-N-(2-methyl-5-(4-piperidinyloxy)phenyl)acetamide, hydrochloride salt, cis-2-(3,5-Dimethyl-4-benzenesulphonyl)piperazin-1-yl)-N-(2-methyl-5-(4-piperidinyloxy)phenyl)acetamide, cis-2-(3,5-Dimethyl-4-(quinazolin-4-yl)piperazin-1-yl)-N-(2-methyl-5-(4-piperidinyloxy)phenyl)acetamide, cis-2-(3,5-Dimethyl-4-(4-quinazolinyl)piperazin-1-yl)-N-(2-methyl-5-(piperazin-4-yl-methyl)phenyl)acetamide, cis-2-(3,5-Dimethyl-4-(4-quinazolinyl)piperazin-1-yl)-N-(2-methyl-5-(2-(N-methylamino)ethoxy)phenyl)acetamide, cis-2-[4-(3-Cyanobenzenesulphonyl)-3,5-dimethylpiperazin-1-yl]-N-(2-methylphenyl)acetamide, cis-N-(2-Methylphenyl)-2-[4-(3]-nitrobenzenesulphonyl)-3,5-dimethylpiperazin-1-yl]-acetamide, cis-2-[4-(3-Aminobenzenesulphonyl)-3,5-dimethylpiperazin-1-yl]-N-(2-methylphenyl)acetamide, cis-2-(3,5-Dimethyl-4-(3-cyanobenzenesulphonyl)piperazin-1-yl)-N-(quinolin-5-yl)acetamide, cis-2-(3,5-Dimethyl-4-(4-cyanobenzenesulphonyl)piperazin-1-yl)-N-(quinolin-5-yl)acetamide, cis-2-(4-(3-Cyanobenzenesulphonyl)-3,5-dimethylpiperazin-1-yl)-N-(3-fluoro-2-methylphenyl)acetamide, cis-2-(4-(4-Cyanobenzenesulphonyl)-3,5-dimethylpiperazin-1-yl)-N-(3-fluoro-2-methylphenyl)acetamide, cis-2-[4-(3-Acetylaminobenzenesulphonyl)-3,5-dimethylpiperazin-1-yl]-N-(2-methylphenyl)acetamide, cis-2-[4-(3-Aminocarbonylbenzenesulphonyl)-3,5-dimethylpiperazin-1-yl]-N-(2-methylphenyl)acetamide, cis-2-[4-(3-Methanesulphonylaminobenzenesulphonyl)-3,5-dimethylpiperazin-1-yl]-N-(2-methylphenyl)acetamide, cis-2-[4-(2-Methanesulphonylbenzenesulphonyl)-3,5-dimethylpiperazin-1-yl]-N-(3-methoxy-2-methylphenyl)acetamide, cis-2-[4-(2-Methanesulphonylbenzenesulphonyl)-3,5-dimethylpiperazin-1-yl]-N-(3-fluoro-2-methylphenyl)acetamide, cis-2-[4-(1-Methylimidazol-4-sulphonyl-4-yl)-3,5-dimethylpiperazin-1-yl]-N-(quinolin-5-yl)acetamide, cis-2-[4-(1-Methylimidazol-4-sulphonyl-4-yl)-3,5-dimethylpiperazin-1-yl]-N-(3-methoxy-2-methylphenyl)acetamide, cis-2-[4-(1-Methylimidazol-4-sulphonyl-4-yl)-3,5-dimethylpiperazin-1-yl]-N-(3-fluoro-2-methylphenyl)acetamide, cis-2-[4-(3-Methanesulphonylbenzenesulphonyl)-3,5-dimethylpiperazin-1-yl]-N-(2-trifluoromethylphenyl)acetamide, cis-2-[4-(2-Aminoethylaminocarbonylbenzenesulphonyl)-3,5-dimethylpiperazin-1-yl]-N-(2-methylphenyl)acetamide, cis-2-[4-(1,2,2-Tetrahydroisoquilin-7-sulphonyl-7-y)-3,5-dimethylpiperazin-1-yl]-N-(2,6-dimethylphenyl)acetamide, cis-2-[4-(3-Cyanobenzenesulphonyl)-3,5-dimethylpiperazin-1-yl]-N-(2,6-dimethylphenyl)acetamide, cis-2-[4-(4-Cyanobenzenesulphonyl)-3,5-dimethylpiperazin-1-yl]-N-(2-methylphenyl)acetamide, cis-2-[4 (2-Cyanobenzenesulphonyl)-3,5-dimethylpiperazin-1-yl]-N-(2,6-dimethylphenyl)acetamide, hydrochloride salt, cis-2-[4-(3-Cyanobenzenesulphonyl)-3,5-dimethylpiperazin-1-yl]-N-(2-chlorophenyl)acetamide, 2-[8-(Isquinolin-1-yl)-3,8-diazabicyclo[3.2.1]oct-3-yl]-N-(2-methylphenyl)acetamide, cis-2-[4-(4-Acetamidobenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(2-trifluoromethylphenyl)acetamide, cis-2-[4-(3-Cyanobenzenesulphonyl)-3,5-dimethylpiperazin-1-yl]-N-(2-methyl-5-methanesulphonamidophenyl)acetamide, 2-[8-(4-Benzenesulphonyl)-3,8-diazabicyclo[3.2.1]oct-3-yl]-N-(2-methylphenyl)acetamide, 2-[8-(2-Benzenesulphonyl)-3,8-diazabicyclo[3.2.1]oct-3-yl]-N-(2-methylphenyl)acetamide, cis-2-[4-(1,2-Dimethylimidazol-4-sulphonyl-4-yl)-3,5-dimethylpiperazin-1-yl]-N-(quinolin-5-yl)acetamide, cis-2-[4-(5-Chloro-1,3-dimethylpyrazole-4-sulphonyl-4-yl)-3,5-dimethylpiperazin-1-yl]-N-(3-methoxy-2-methylphenyl)acetamide, 2-[8-(2-(Isoxazol-3-yl)thiophen-5-yl)-3,8-diazabicyclo[3.2.1]oct-3-yl]-N-(2-methylphenyl)acetamide, 2-[8-(1,1,2,2-Tetrahydroisoquinilin-7-sulphonyl)-3,8-diazabicyclo[3.2.1]oct-3-yl]-N-(2-methylphenyl)acetamide, cis-2-[4-(5-Chloro-1,3-dimethylpyrazole-4-sulphonyl-4-yl)-3,5-dimethylpiperazin-1-yl]-N-(2-methylphenyl)acetamide, cis-2-[4-(3,5-Dimethylisoxazole-4-sulphonyl-4-yl)-3,5-dimethylpiperazin-1-yl]-N-(2-methylphenyl)acetamide, cis-2-[4-(2-Methanesulphonylbenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(3-methoxy-2-methylphenyl)acetamide, cis-2-[4-(4-Methanesulphonylbenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(5-cyano-2-methylphenyl)acetamide, cis-2-[4-(3-Cyanobenzenesulphonyl)-3,5-dimethylpiperazin-1-yl]-N-(5-acetamido-2-methylphenyl)acetamide, (R)-2-[4-(4-Cyanobenzenesulphonyl)-3-methylpiperazin-1-yl]-N-(quinolin-5-yl)acetamide, (S)-2-[4-(4-Cyanobenzenesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-5-methanesulphonylphenyl)acetamide, cis-2-[4-(3-Cyanobenzenesulphonyl)-3,5-dimethylpiperazin-1-yl]-N-(2-methyl-5-(4-amino-1-piperidinyl)methyl)phenyl]acetamide, (R)-2-[4-(4-Methanesulphonylbenzenesulphonyl)-3-methylpiperazin-1-yl]-N-(quinolin-5-yl)acetamide, (R)-2-[4-(4-Acetamidobenzenesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-5-(1-piperazinylmethyl)phenyl)acetamide, cis-2-[4-(3-Cyanobenzenesulphonyl)-3,5-dimethylpiperazin-1-yl]-N-(2-methyl-5-(4-piperidinylamino)methyl)phenyl]acetamide, cis-2-[4-(3-Cyanobenzenesulphonyl)-3,5-dimethylpiperazin-1-yl]-N-(2-methyl-5-(1-morpholinyl)methyl)phenyl]acetamide, cis-2-[4-(3-Cyanobenzenesulphonyl)-3,5-dimethylpiperazin-1-yl]-N-(2-methyl-5-(2-hydroxyethylamino)methyl)phenyl]acetamide, cis-2-[4-(3-Cyanobenzenesulphonyl)-3,5-dimethylpiperazin-1-yl]-N-(2-methyl-5-(S,S)-(2,5-diazabicyclo[2.2.1]hept-2-yl)methyl)phenyl]acetamide, (R)-2-[4-(2-Pyridinesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-3-(4-amino-1-piperidinyl)methyl)phenyl]acetamide, cis-2-[4-(3-Cyanobenzenesulphonyl)-3,5-dimethylpiperazin-1-yl]-N-(2-methyl-3-(4-piperidinylamino)methyl)phenyl]acetamide, cis-2-[4-(3-Cyanobenzenesulphonyl)-3,5-dimethylpiperazin-1-yl]-N-(2-methyl-3-(1-piperazinylmethyl)phenyl)acetamide, cis-2-[4-(3-Cyanobenzenesulphonyl)-3,5-dimethylpiperazin-1-yl]-N-(2-methyl-3-(S,S)-(2,5-diazabicyclo[2.2.1]hept-2-yl)methyl)phenyl)acetamide, cis-2-[4-(3-Cyanobenzenesulphonyl)-3,5-dimethylpiperazin-1-yl]-N-((2-methyl-3-(1-morpholinyl)methyl)phenyl)acetamide, cis-2-[4-(3-Cyanobenzenesulphonyl)-3,5-dimethylpiperazin-1-yl]-N-((2-methyl-3-(2-(1-pyrrolidinyl)ethoxy)phenyl)acetamide, (±) cis-2-[4-(3-Cyanobenzenesulphonyl)-3,5-dimethylpiperazin-1-yl]-N-((2-methyl-3-(1-methylpiperidin-3-yl)methoxy)phenyl)acetamide, cis-2-[4-(3-Cyanobenzenesulphonyl)-3,5-dimethylpiperazin-1-yl]-N-((2-methyl-4-(2-(1-pyrrolidinyl)ethoxy)phenyl)acetamide, (±) cis-2-[4-(3-Cyanobenzenesulphonyl)-3,5-dimethylpiperazin-1-yl]-N-((2-methyl-4-(1-methylpiperidin-3-yl)methoxy)phenyl)acetamide, (±) cis-2-[4-(3-Cyanobenzenesulphonyl)-3,5-dimethylpiperazin-1-yl]-N-((2-methyl-5-(1-methylpiperidin-3-yl)methoxy)phenyl)acetamide, (±) cis-2-[4-(3-Cyanobenzenesulphonyl)-3,5-dimethylpiperazin-1-yl]-N-((2-methyl-6-(1-methylpiperidin-3-yl)methoxy)phenyl)acetamide, and cis-2-[4-(1-Methylimidazol-4-sulphonyl-4-yl)-3,5-dimethylpiperazin-1-yl]-N-((2-methyl-3-(2-(1-pyrrolidinyl)ethoxy)phenyl)acetamide, and their pharmaceutically acceptable salts and solvates.

The present invention further provides a process for the preparation of a compound of formula (I) as defined above which comprises:

(a) reacting a compound of general formula

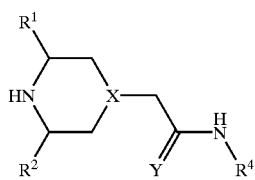

(II)

wherein X, Y, $R^1$, $R^2$ and $R^4$ are as defined in formula (I), with a compound of general formula (III), $R_3$—$(SO_2)_m$-$L^1$, wherein $L^1$ represents a leaving group (e.g. a halogen atom or triflate) and m and $R^3$ are as defined in formula (I); or (b) when X represents a nitrogen atom and Y represents an oxygen atom, reacting a compound of general formula

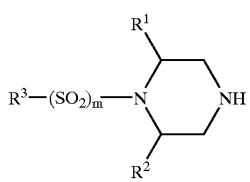

(IV)

wherein m, $R^1$, $R^2$ and $R^3$ are as defined in formula (I), with a compound of general formula

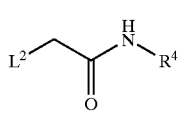

(V)

wherein $L^2$ represents a leaving group such as a halogen atom and $R^4$ is as defined in formula (I); or (c) reacting a compound of general formula

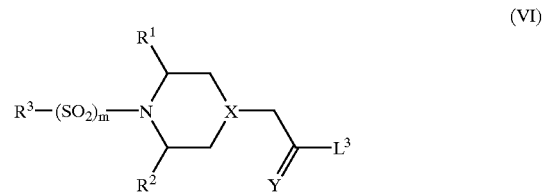

(VI)

wherein $L^3$ represents a leaving group such as a halogen atom or hydroxyl group and m, X, Y, $R^1$, $R^2$ and $R^3$ are as defined in formula (I), with a compound of general formula (VII), $H_2N$—$R^4$, wherein $R^4$ is as defined in formula (I);

and optionally after (a), (b) or (c) converting the compound of formula (I) obtained to a pharmaceutically acceptable salt or solvate thereof.

Processes (a) and (b) are conveniently carried out in the presence of a base, e.g. a metal carbonate such as potassium or caesium carbonate or a trialkylamine such as triethylamine, preferably N,N-diisopropylethylamine, and in the presence of a polar solvent (e.g. 1-methyl-2-pyrrolidinone, dimethylformamide, ethanol, tetrahydrofuran or 1,4-dioxane).

Process (c) is conveniently carried out in the presence of a base and a polar solvent as described above for processes (a) and (b). In addition, a coupling reagent is suitably used, for example, 1,1'-carbonyldiimidazole, 1,3-dicyclohexylcarbodiimide or bromo-tris-oxy-tripyrrolidinophosphonium hexafluorophosphate.

Compounds of formulae (II), (III), (IV), (V), (VI) and (VII) are either commercially available, are well known in the literature or may be prepared easily using known techniques.

It will be appreciated by those skilled in the art that in the processes of the present invention certain functional groups such as hydroxyl, carboxyl or amino groups in the starting reagents or intermediate compounds may need to be protected by protecting groups. Thus, the preparation of the compounds of formula (I) may involve at a certain stage the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

It will be appreciated that certain compounds of formula (I) may be converted to further compounds of formula (I) by techniques known in the art such as alkylation, hydrolysis, amide bond formation, esterification or reductive amination.

The compounds of formula (1) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity and have utility as modulators of $P2X_7$ receptor activity. They are therefore indicated as pharmaceuticals for use in the treatment or prevention of rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, meningitis, osteoporosis, burn injury, ischaemic heart disease, stroke, peripheral vascular disease and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of rheumatoid arthritis, irritable bowel disease, atherosclerosis, psoriasis, pulmonary disease, e.g. COPD or bronchitis, or diseases of the central nervous system, e.g. Alzheimer's disease or stroke) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disease or condition indicated. For effecting immunosuppression, the daily dosage of the compound of formula (I) will typically be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (1) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

(±)-N-(2,6-Dimethylphenyl)-2-(3-methyl-4-(thieno[12,3-d]pyrimidin-4-yl)piperazin-1-yl)acetamide

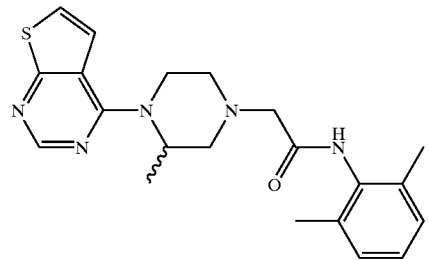

i) (±)-1,1-Dimethylethyl, 3-methyl-4-(thieno[2,3-d]pyrimidin-4-yl)piperazine-1-carboxylate A solution of 4-chloro-thieno[2,3-d]pyrimidine (0.2 g) and (±)-1,1-dimethylethyl, 3-methylpiperazine-1-carboxylate (J. Med. Chem., 1993, 36, 690–698) (0.23 g) in ethanol (50 ml) was heated under reflux for 24 hours. The solvent was evaporated and the residue purified by flash column chromatography eluting with ethyl acetate/isohexane (3:7) to give the subtitle compound as a yellow gum. Yield 0.33 g.

MS: APCI(+ve) 335 (M+1,100%)

ii) (±)-2-Methyl-1-(thieno[2,3-d]pyrimidine-4-yl)piperazine, Trifluoroacetic Acid Salt A mixture of the product from step (i) (0.33 g) and trifluoroacetic acid (4 ml) in dichloromethane (5 ml) was stirred at room temperature for 2 hours. The solvent was evaporated under reduced pressure. Toluene (20 ml) was added to the residue and then evaporated under reduced pressure to give the crude subtitle compound as a gum. The product was used without further purification in the next step.

MS: APCI(+ve) 235 (M+1,100%)

iii) (±)-N-(2,6-Dimethylphenyl)-2-(3-methyl-4-(thieno[2,3-d]pyrimidin-4-yl)piperazin-1-yl)acetamide A mixture of the product from step (ii) (0.23 g), N,N-diisopropylethylamine (0.65 g) and 2-chloro-N-(2,6-dimethylphenyl)acetamide (0.2 g) in dimethylformamide (4 ml) was heated at 80° C. for 18 hours. The reaction mixture was cooled and diluted with ethyl acetate. The organic solution was washed with a small volume of water and the solvent evaporated under reduced pressure. The residue was purified by flash chromatography eluting with ethyl acetatelisohexane (6:4) to give the product as a gum. The gum was further purified by reverse phase high pressure liquid chromatography (methanol/0.1% aqueous ammonium acetate, gradient elution 15% to 85% organic phase) to give the title product, after freeze drying, as a beige solid. Yield 0.095 g.

MS: APCI(+ve) 396 (M+1,100%)

¹H NMR: δ (CDCl₃) 8.5(2H, s); 7.32(2H, q); 7.13(3H, m); 4.98(1H, bs); 4.60(1H, bd); 3.59(1H, dt); 3.25(2H, q); 3.12(1H, bd); 2.98(1H, d); 2.72(1H, dd); 2.55(1H, dt); 2.28(6H, s); 1.53(3H, d).

MP: 184–185° C.

EXAMPLE 2 cis-[2-(3,5-Dimethyl-4-(thieno[2,3-d]pyrimidin-4-yl)piperazin-1-yl)]-N-(2,6-dimethylphenyl)acetamide

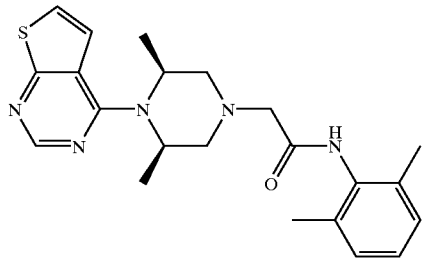

i) cis-1,1-Dimethylethyl, 3,5-dimethyl-4-(thieno[2,3-d]pyrimidine-4-yl)piperazin-1-carboxylate A solution of 4-chloro-thieno[2,3-d]pyrimidine (4.0 g), cis-1,1-dimethylethyl, 3,5-dimethylpiperazine-1-carboxylate (J. Med. Chem., 1999, 4(7), 1123–1114) (12 g) and N,N-diisopropylethylamine (10 ml) in 1-methyl-2-pyrrolidinone (30 ml) was heated at 120° C. for 5 days under nitrogen. The reaction mixture was cooled and diluted with ethyl acetate. The organic solution was washed with water, dried (MgSO₄) and the solvent evaporated under reduced pressure. The residue was purified by flash column chromatography eluting with ethyl acetate/isohexane (2:8) to give the subtitle compound as a beige solid. Yield 5.5 g.

MS: APCI(+ve) 349 (M+1,100%)

ii) cis-2,6-Dimethyl-1-(thieno[2,3-d]pyrimidin-4-yl)piperazine, trifluoroacetic acid salt The subtitle compound was prepared from the product of step (i) (0.15 g) by the method of Example 1 step (ii) as a gum. This was used without purification in the next step.

MS: APCI(+ve) 249 (M+1,100%).

iii) cis-[2-(3,5-Dimethyl-4-(thieno[2,3-d]pyrimidin-4-yl)piperazin-1-yl)]-N-(2,6-dimethylphenyl)acetamide A mixture of the product from step (ii), N,N-diisopropylethylamine (0.37 ml) and 2-chloro-N-(2,6-dimethylphenyl)acetamide (0.08 g) in 1-methyl-2-pyrrolidinone (5 ml) was heated at 100° C. for 24 hours. The reaction mixture was cooled and diluted with ethyl acetate. The organic solution was washed with a small volume of water, dried (MgSO₄) and the solvent evaporated under reduced pressure. The residual red oil was purified by reverse phase high pressure liquid chromatography (acetonitrile/0.1% aqueous ammonium acetate, gradient elution 20% to 80% organic phase) to give the title product, after freeze drying, as a cream solid. Yield 0.05 g.

MS: APCI(+ve) 410 (M+1,100%)

¹H NMR: δ (CDCl₃) 8.5(2H, s); 7.38(1H, d); 7.26(1H, d); 7.14(3H, m); 5.10(2H, bs); 3.29(2H, d); 3.01(2H, d); 2.65 (2H, dd); 2.30(6H, s); 1.56(6H, d).

MP: 186–189° C.

EXAMPLE 3

(±)-2-[3-Methyl-4-(4-methylphenyl)piperazin-1-yl]-N-(2,6-dimethylphenyl)acetamide

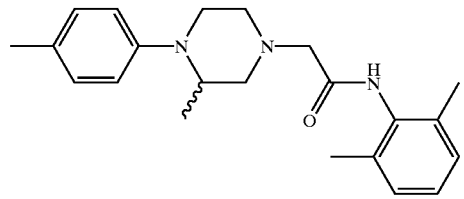

The title compound was prepared from (±)-3-methyl-4-(4-methylphenyl)piperazine (0.1 g) and 2-chloro-N-(2,6-dimethylphenyl)acetamide (0.1 g) by the method of Example 1 step (iii) as a white solid. Yield 0.056 g.

MS: APCI(+ve) 352 (M+1,100%).

¹H NMR: δ (CDCl₃) 8.63(1H, s); 7.09(5H, m); 6.87(2H, d); 3.78(1H, bm); 3.24(2H, d); 3.17(2H, m); 2.95(1H, m); 2.88(1H, dd); 2.72(2H, m); 2.29(3H, s); 2.26(6H, s); 1.08 (3H, d).

EXAMPLE 4 cis-N-[3-Hydroxymethyl-2-methylphenyl]-2-(3,5-dimethyl-4-(thieno[2,3-d]pyrimidin-4-yl)piperazin-1-yl)acetamide

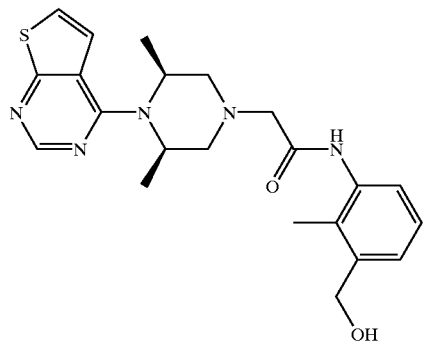

i) cis-N-[3-((1,1-Dimethyl)-1-dimethylethyl)silyloxymethyl-2-methylphenyl]-2-(3,5-dimethyl-4-(thieno[2,3-d]pyrimidin-4-yl)piperazin-1-yl)acetamide The subtitle compound was prepared from N-(3-((1,1-dimethyl-1-dimethylethyl)silyloxymethyl)-2-methylphenyl)-2-chloroacetamide (Chem. Abs., 1997, 765311) (0.1 g) and the product from Example 2 step (ii) (0.1 g) by the method of Example 2 step (iii) as a red oil. This was used directly in the next step without further purification.

ii) cis-N-[3-Hydroxymethyl-2-methylphenyl]-2-(3,5-dimethyl-4-(thieno[2,3-d]pyrimidin-4-yl)piperazin-1-yl)acetamide The subtitle product from step (i) (0.15 g) in anhydrous tetrahydrofuran was treated with a 1M solution of tetrabutyl ammonium fluoride in tetrahydrofuran (0.31 ml) and the mixture stirred at room temperature for 1 hour. The solvent was removed under reduced pressure and the residue purified by high pressure liquid chromatography (acetonitrile/0.1% aqueous ammonium acetate, gradient elution 20% to 80% organic phase) to give the title compound as a white solid. Yield 0.025 g.

MS: APCI(+ve) 426 (M+1,100%)

¹H NMR: δ (CDCl₃/DMSO) 8.97(1H, s), 8.49(1H, s), 7.89(1H, d), 7.32(1H, d), 7.26(3H, m), 5.09(2H, bs), 4.74 (2H, s), 3.27(2H, s), 2.96(2H, d), 2.63(2H, dd), 2.36(3H, s), 1.58(6H, bs)

MP: 203–204° C.

EXAMPLE 5

(R)-2-[4-(1-Methylimdazol-4-sulphonyl-4-yl)-3-ethylpiperazin-1-yl]-N-(quinolin-5-yl)acetamide

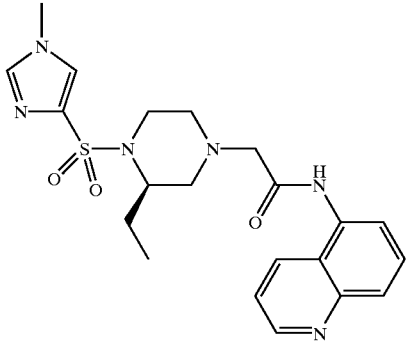

i) (R)-3-Ethyl-1-(phenylmethyl)-2,5-piperazinedione

To a stirred solution of (R)—N-BOC-2-aminobutyric acid (3.36 g) and ethyl N-benzylglycine (4.52 g) in dichloromethane (50 ml) at 15° C. was added dicyclohexylcarbodiimide (3.59 g). The temperature was maintained at 10–15° C. for a further 2 h and then allowed to stir at ambient temperature for a further 16 h. The mixture was filtered and the mother liquor collected and solvent evaporated under reduced pressure. The residue was re-dissolved in dichloromethane (20 ml) and hydrogen chloride gas passed through the mixture for 20 minutes. The mixture was quenched with aq. saturated sodium bicarbonate solution and extracted with ethyl acetate, collected, dried (MgSO₄) and solvent evaporated under reduced pressure to leave a colourless oil. This was purified by crystallisation from ether/iso-hexane mixtures to give the subtitle compound as a white solid. Yield: 1.35 g ¹H NMR δ (DMSO) 8.30(s, 1H), 7.24–7.39(m, 5H), 4.60(d, 1H), 4.44 (d, 1H), 3.92(t, 1H), 3.78(d, 3H), 1.75(m, 2H), 0.84(t, 3H).

ii) (R)-3-Ethyl-1-phenylmethyl)piperazine

A stirred solution of the product from step (i) (6.0 g) in tetrahydrofuran (250 ml) at 0° C. was treated with lithium aluminium hydride (3.44 g). The mixture was allowed to stir at ambient temperature for 24 h and then set at reflux for 4 h. The mixture was carefully quenched with 10% aq. sodium hydroxide solution (10 ml). After stirring for 30 minutes the mixture was filtered and the mother liquor partitioned between ethyl acetate and brine. The organic layer collected, dried (MgSO₄) and solvent evaporated under reduced pressure to give the subtitle compound as a pale yellow oil. Yield: 5.8 g ¹H NMR δ (CDCl₃) 7.32(s, 5H), 3.50(dd, 2H), 2.62–3.0 (m, 5H), 2.00 (m, 1H), 1.70(t, 1H), 1.57(s, 1H), 1.27(m, 2H), 0.90(t, 3H)

iii) (R)-1-(1-Methylimidazol-4-sulphonyl-4-yl)-2-ethyl-4-phenylmethyl)piperazine The subtitle compond was prepared from the product of step (ii) (0.5 g) and 1-methylimidazole-4-sulphonyl chloride (0.5 g) by the method of Example 80 step (i) as a pale yellow solid. Yield: 0.53 g ¹H NMR δ (CDCl₃) 7.46(s, 1H), 7.38(s, 1H), 7.29(m, 5H), 3.80(s, 2H), 3.47(d, 1H), 3.3(d+m, 2H), 2.64(d, 2H), 2.08(m, 2H), 1.79(m, 2H), 0.82(t, 3H)

iv) (R)-1-(1-Methylimidazol-4-sulphonyl-4-yl)-2-ethyl) piperazine

The subtitle compound was prepared from the product of step (iii) (0.49 g) by the method of Example 80 step (ii) as a pale yellow solid. Yield: 0.32 g ¹H NMR δ (CDCl₃) 7.6(d, 2H), 7.5(m, 4H), 4.05(s, 1H), 3.73(s, 3H), 3.42(d, 1H), 3.04(d, 2H), 2.87(m, 1H), 2.32(m, 1H), 1.87(m, 2H), 0.91(t, 3H)

v) (R)-2-[4-(1-Methylpiperazin-4-sulphonyl-4-yl)-3-ethylpiperazin-1-yl]-N-(quinolin-5-yl)acetamide The title compound was prepared from the product of step (iv) (0.23 g) and 2-chloro-N-(quinolin-5-yl)acetamide (0.21 g)) (J. Indian Chem Soc, 1940, 17, 619–621) by the method of Example 80 step (iii) as a cream solid. Yield: 21 mg MS: APCI (+ve) 443 (M+1)

¹H NMR δ (CD₃OD) 9.16(d, 1H), 9.07(d, 1H), 8.10(s, 3H), 7.97(t, 1H), 7.81(d, 1H), 7.70(t, 1H), 7.50(dd, 1H), 4.29(m, 2H), 4.10(m, 2H), 3.81(s, 3H), 3.69(m, 2H), 3.32(m, 2H), 3.15(m, 2H), 1.84(m, 2H), 0.99(t, 3H)

EXAMPLE 6 cis-2-[3,5-Dimethyl-4-(thieno[2,3-d]pyrimidin-4-yl) piperazin-1-yl]-N-(2-methylphenyl)acetamide

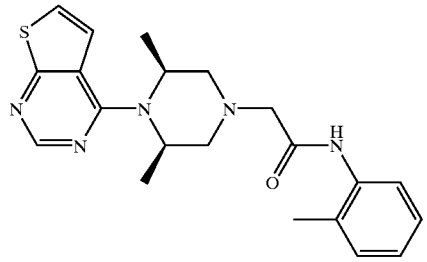

The title compound was prepared from the product of Example 9 step (ii) (0.316 g) and 2-methylaniline (0.09 g) by the method of Example 8 step (v) as a white solid. Yield 0.202 g MS: APCI(+ve) 396 (M+1,100%)

¹H NMR: δ (DMSO) 9.25(1H, s), 8.40(1H, d), 7.60–7.67 (3H, m), 7.26(2H, m), 7.10(1H, m), 5.01(2H, bs), 3.23(2H, s), 2.96(2H, d), 2.45(2H, m), 2.29(3H, s), 1.50(6H, m)

MP: 174–175° C.

EXAMPLE 7 cis-N-(2-Chlorophenyl)-2-[3,5-dimethyl-4-(thieno[2,3-d]pyrimidin-4-yl)piperazin-1-yl]acetamide

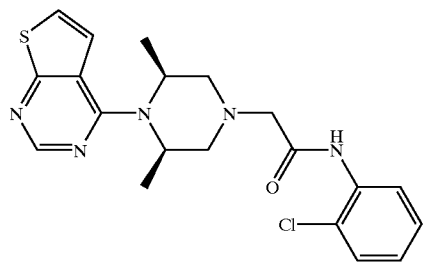

The title compound was prepared from the product of Example 8 step (ii) (0.316 g) and 2-chloroaniline (0.107 g) by the method of Example 1 step (iii) as a white solid. Yield 0.119 g.

MS: APCI(+ve) 416 (M+1,100%)

¹H NMR: δ(DMSO) 9.70(1H, s), 8.55(1H, d), 7.27–7.42 (3H, m), 7.26(2H, s), 7.08(1H, t), 5,08(2H, bs), 3.26(2H, s), 2.94(2H, d), 2.60(2H, m), 1.63(6H, d)

MP: 206–207° C.

EXAMPLE 8 cis-N-(2-Chlorophenyl)-2-[3,5-dimethyl-4-(9-methyl-9H-purin-6yl)piperazin-1-yl]acetamide

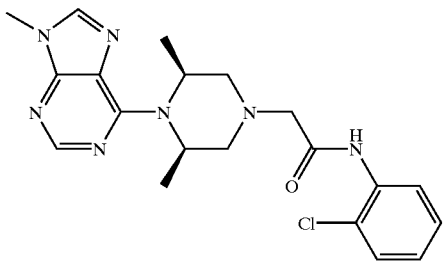

i) cis-1,1-Dimethylethyl, 3,5-dimethyl-4-(9-methyl-9H-purin-6-yl)piperazine-1-carboxylate The subtitle compound was prepared from 6-chloro-9-methyl-9H-purine (J. Org. Chem., 1983, 48 (6), 850–5) (2 g) and cis-1,1-dimethylethyl, 3,5-dimethylpiperazine-1-carboxylate (2.74 g) by the method of Example 2 step (i) as beige solid. Yield 0.2 g.

¹H NMR: δ (CDCL₃) 8.40(1H, S), 7.73(1H, S), 4.20–4.00 (3H, BRM), 3.30–3.00(3H, BRM), 1.5(9H, S), 1.40(6H, D)

ii) cis-2,6-Dimethyl-1-(9-methyl-9H-purin-6-yl)piperazine, trifluoroacetic acid salt The subtitle compound was prepared from the product of step (i) (0.2 g) by the method of Example 1 step (ii) as a red gum. This was used directly in the next step.

MS: APCI(+ve) 247 (M+1,100%)

iii) cis-1,1-Dimethylethyl, 2-(3,5-dimethyl-4-(9-methyl-9H-purin-6-yl)piperazin-1-yl)acetate A mixture of the product from step (ii) (0.34 g), tert-butyl bromoacetate (0.13 g) and sodium bicarbonate (0.8 g) in acetone was heated at 45° C. for 18 hours. The reaction mixture was filtered and the filtrate evaporated under reduced pressure. The residual brown gum was purified by flash chromatography eluting with ethyl acetate/isohexane/triethylamine (7:2.5:0.5) to give the subtitle compound as a pale yellow gum. Yield 0.12 g.

MS: APCI(+ve) 361 (M+1,100%)

iv) cis-2-(3,5-Dimethyl-4(9-methyl-9H-purin-6-yl)piperazin-1-yl)acetic acid, hydrochloride salt The product from step (iii) (0.12 g) in dichloromethane was treated with 1M hydrogen chloride in diethyl ether (12 ml). The mixture was stirred at room temperature for 18 hours. The solvent was evaporated under reduced pressure to give the subtitle product as a pale yellow solid. Yield 0.15 g.

MS: APCI(+ve) 305 (M+1,100%)

v) cis-N-(2-Chlorophenyl)-2-[3,5-dimethyl-4-(9-methyl-9H-purin-6yl)piperazin-1-yl]acetamide Bromo-tris-oxy-tripyrrolidinophosphonium hexafluorophosphate (known as PyBroP) (0.18 g) was added to a stirred solution of the product from step (iv) (0.14 g), 2-chloroaniline (0.05 g) and N,N-diisopropylethylamine (0.3 g) in anhydrous dimethylformamide (6 ml). After stirring for 4 hours a further aliquot of 2-chloroaniline (0.1 ml) and PyBroP (0.18 g) were added and the mixture further stirred at room temperature for four days. Water was added and the precipitate filtered to give the crude product as a brown solid (0.07 g). This was purified by high pressure liquid chromatography (acetonitrile/0.1% aqueous ammonium acetate, gradient elution 25% to 75% organic phase) to give the title product as a white solid. Yield 0.04 g.

MS: APCI(+ve) 414/416 (M+1,100%)

¹H NMR: δ (CDCl₃/DMSO) 9.76(1H, s), 8.52(1H, dd), 8.39(1H, s), 7.78(1H, s), 7.40(1H, dd), 7.31(1H, dt), 7.07 (1H, dt), 5.50(2H, bs), 3.83(3H, s), 3.26(2H, s), 2.94(2H, d), 2.59(2H, m), 1.58(6H, d)

MP: 221–222° C.

EXAMPLE 9 cis-2-(3,5-Dimethyl-4-(thieno[2,3-d]pyrimidin-4-yl) piperazin-1-yl)-N-(isoquinolin-5-yl)acetamide

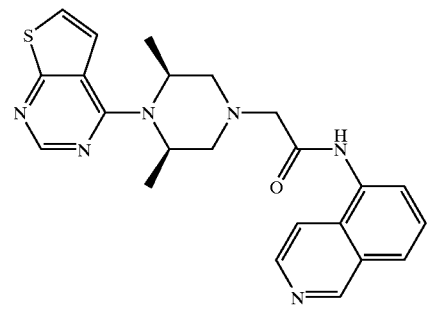

i) cis-1,1-Dimethylethyl, 2-(3,5-dimethyl-4-(thieno[2,3-d] pyrimidin-4-yl)piperazin-1-yl)acetate The subtitle compound was prepared from the product of Example 2 step (ii) (3.0 g) and tert-butyl bromoacetate (1.15 g) by the method of Example 8 step (iii) as a white solid. Yield 1.0 g.

MS: APCI(+ve) 363 (M+1,100%)

ii) cis-2-(3,5-Dimethyl-4-(thieno[2,3-d]pyrimidin-4-yl) piperazin-1-yl)acetic acid, hydrochloride salt The product from step (i) (1.0 g) in 1,4-dioxane was treated with 4M hydrogen chloride in 1,4-dioxane (40 ml). The mixture was stirred at room temperature for 18 hours. The solvent was evaporated under reduced pressure to give the subtitle compound as a white 15 solid. Yield 1.9 g.

MS: APCI(+ve) 307 (M+1,100%)

iii) cis-2-(3,5-Dimethyl-4-(thieno[2,3-d]pyrimidin-4-yl) piperazin-1-yl)-N-(isoquinolin-5-yl)acetamide The title product was prepared from the product of step (ii) (0.2 g) and 5-aminoisoquinoline (0.084 g) by the method of Example 8 step (v) as a white solid. Yield 0.11 g.

MS: APCI(+ve) 433 (M+1,100%)

¹H NMR: δ (CDCl₃) 9.62(1H, bs), 9.30(1H, s), 8.59(1H, d), 8.51(1H, s), 8.46(1H, d), 7.85(1H, d), 7.68(2H, m), 7.38(1H, d), 7.28(1H, m), 5.13(2H, bs), 3.38(2H, s), 3.03 (2H, d), 2.70(2H, dd), 1.65(6H, d)

MP: 213–216° C.

EXAMPLE 10 cis-2-(3,5-Dimethyl-4-thieno[2,3-d]pyrimidin-4-yl)
piperazin-1-yl)-N-(quinolin-5-yl)acetamide

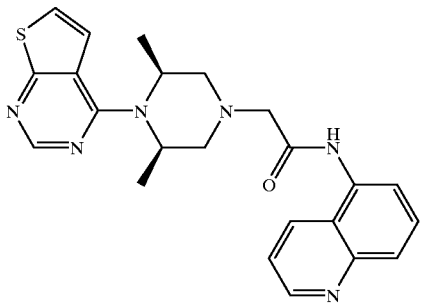

The title compound was prepared from the product of Example 9 step (ii) (0.207 g) and 5-aminoquinoline (0.072 g) by the method of Example 8 step (v) as a white solid. Yield 0.11 g.

MS: APCI(+ve) 433 (M+1, 100%)

$^1$H NMR: δ (CDCl$_3$) 9.53(1H, s), 8.97(1H, s), 8.51(1H, s), 8.28(1H, s). 8.00(1H, s), 7.77(1H, t), 7.47(1H, m), 7.42(1H, d), 7.37(1H, d), 5.13(2H, s), 3.38(2H, s), 3.03(2H, d), 2.71(2H, d), 2.29(3H, s), 1.63(6H, d)

MP: 194–195° C.

EXAMPLE 11 cis-2-(3,5-Dimethyl-4-(thieno[2,3-d]pyrimidin-4-yl)
piperazin-1-yl)-N-(2-methyl-5-
methylsulphonamidophenyl)acetamide

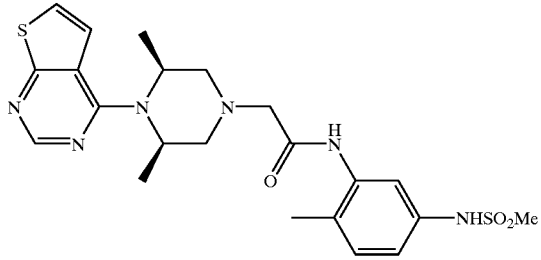

i) 2-Methyl-5-bis(methylsulphonyl)amido-1-nitrobenzene

To a mixture of 5-nitro-4-methylaniline (3.04 g) and N,N-diisopropylethylamine (5.2 ml) in dichloromethane (40 ml) was added dropwise a solution of methanesulphonyl chloride (2.29 g) in dichloromethane (10 ml) over 40 mins. After stirring for 16 hours the mixture was poured into 2% aq. HCl. The organic phase collected and further washed with brine, dried (Na$_2$SO$_4$) and solvent evaporated under reduced pressure to leave the crude product. This was purified by silica-gel chromatography eluting with dichloromethane to give the subtitle compound as a pale yellow solid. Yield 4.46 g. This was used directly in the next step.

ii) 2-Methyl-5-bis(methylsulphonyl)amido-1-aniline

A mixture of the product from step (i) (3.8 g), ammonium chloride (3.8 g), reduced iron powder (3.8 g) in ethanol (30 ml) and water (10 ml) were stirred at 80° C. for 5 minutes. The mixture was filtered through Celite and further washed with ethanol and dichloromethane. The filtrate was concentrated to a quarter of the volume and then water added to give a brown precipitate. This was filtered to give the subtitle compound as a brown solid. Yield 1.25 g. The mother liquor was further partitioned between water and ethyl acetate. The organic phase collected, dried (Na$_2$SO$_4$) and evaporated to give a second batch of the subtitle compound as an orange solid. Yield 1.1 g.

$^1$H NMR: δ (DMSO) 6.98(1H, d), 6.65(1H, s), 6.56(1H, d), 2.50(6H, s), 2.06(3H, s)

iii) cis-2-(3,5-Dimethyl-4-(thieno[2,3-d]pyrimidin-4-yl)piperazin-1-yl)-N-(2-methyl-5-bis(methylsulphonyl)amidophenyl)acetamide The subtitle product was prepared from the product of Example 9 step (ii) (0.318 g) and the product of step (ii) (0.172 g) by the method of Example 8 step (v) as a white solid. Yield 0.21 g. This product was used directly in the next step without further purification.

iv) cis-2-(3,5-Dimethyl-4-(thieno[2,3-d]pyrimidin-4-yl)piperazin-1-yl)-N-(2-methyl-5-methylsulphonamidophenyl)acetamide A mixture of the product from step (iii) (0.21 g) and potassium carbonate (0.5 g) was stirred in methanol (20 ml) and water (10 ml) over 24 hours at room temperature. The solid product was filtered and purified by reverse phase HPLC to give the title compound as white solid. Yield 0.058 g.

MS: APCI(+ve) 489 (M+1, 100%)

$^1$H NMR: δ (DMSO) 9.66(1H, s), 9.23(1H, s), 8.40(1H, s), 7.60(3H, s), 7.17(1H, d), 6.94(1H, d), 4.50(2H, bs), 3.22(2H, s), 2.93(2H, s), 2.43(2H, m), 2.22(3H, s), 1.49(6H, d)

EXAMPLE 12 cis-2-(3,5-Dimethyl-4-(thieno[2,3-d]pyrimidin-4-yl)
piperazin-1-yl]-N-(2-trifluoromethylphenyl)
acetamide

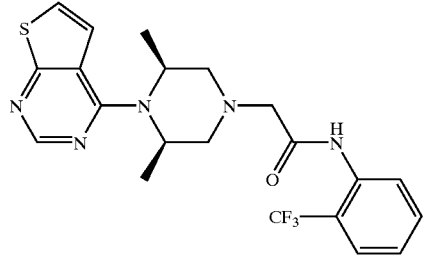

i) cis-2-(3,5-Dimethyl-4-(thieno[2,3-d]pyrimidin-4-yl)piperazin-1-yl)acetyl chloride, hydrochloride salt A mixture of the product from Example 9 step (ii) (1.15 g) and oxalyl chloride (1.2 ml) in dichloromethane (100 ml) was treated with 2 drops of dimethylformamide. After 24 hours at room temperature a further aliquot of oxalyl chloride (3.6 ml) was added and the mixture heated under reflux for 48 hours. The solvent was evaporated under reduced pressure. Toluene was added to the residue and then evaporated under reduced pressure to give the subtitle product as a yellow oil (0.95 g).

MS: (methanol added to give the methyl ester): APCI(+ve) 320 (M(methyl ester)+1,100%)

ii) cis-2-(3,5-Dimethyl-4-(thieno[2,3-d]pyrimidin-4-yl)piperazin-1-yl]-N-(2-trifluoromethylphenyl)acetamide A mixture of the product from step (i) (0.2 g), 2-trifluoromethylaniline (0.11 g) and N,N-diisopropylethylamine in 1,4-dioxane (5 ml) was heated at 80° C. for 18 hours. LC mass spectrum analysis showed cis-(3,5-dimethyl-4-(thieno[2,3-d]pyrimidin-4-yl)piperazin- 1-yl]acetic acid present. PyBroP (0.18 g) and 4-dimethylaminopyridine (0.05 g) were added and the mixture further stirred at room temperature for 18 hours. The solvent was evaporated under reduced pressure and the residue purified by high pressure liquid chromatography (acetonitrile/0.1% aqueous ammonium acetate, gradient elution 25% to 75% organic phase) to give the title product as a white solid. Yield 0.08 g.

MS: APCI(+ve) 450 (M+1,100%)

$^1$H NMR: δ (CDCl$_3$) 9.41(1H, bs), 8.49(1H, s), 8.34(1H, d), 7.65(1H, d), 7.60(1H, t), 7.37(1H, d), 7.27(2H, m), 5.06(2H, bs), 3.24(2H, s), 2.92(2H, d), 2.59(2H, dd), 1.55 (6H, d)

MP: 154–155° C.

EXAMPLE 13 cis-2-(3,5-Dimethyl-4-(thieno[2,3-d]pyrimidin-4-yl) piperazin-1-yl)-N-(3-methylpyridin-2-yl)acetamide

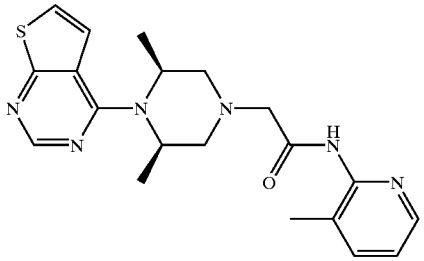

The title compound was prepared by from the product of Example 12 step (i) (0.2 g) and 2-amino-3-methylpyridine (0.076 g) by the method of Example 12 step (ii) as a cream solid. Yield 0.025 g.

MS: APCI(+ve) 397 (M+1,100%)

$^1$H NMR: δ (CDCl$_3$) 9.13(1H, s), 8.47(1H, s), 8.31(1H, d), 7.60(1H, d), 7.40(1H, m), 7.27(1H, d), 7.13(1H, m), 5.09(2H, bs), 3.28(2H, s), 2.91(2H, d), 2.61(2H, m), 2.3(3H, s), 1.60(6H, d)

MP: 157–159° C.

EXAMPLE 14 cis-2-(3,5-Dimethyl-4-(thieno[2,3-d]pyrimidin-4-yl) piperazin-1-yl)-N-(isoquinolin-1-yl)acetamide

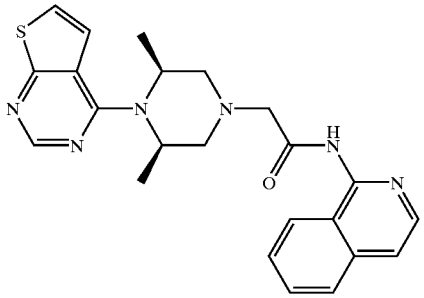

The title product was prepared by from the product of Example 12 step (i) (0.2 g) and isoquinolin-1-ylamine (0.1 g) by the method of Example 12 step (ii) as a cream solid. Yield 0.055 g.

MS: APCI(+ve) 433 (M+1,100%)

$^1$H NMR: δ (CDCl$_3$) 9.65(1H, bs); 8.49(1H, s); 8.37(1H, bs); 8.05(1H, bd); 7.72(1H, t); 7.60(2H, t); 7.39(1H, d); 7.26(1H, m); 5.12(2H, bs); 3.39(2H, s); 3.07(2H, d); 2.67 (2H, dd); 1.63(6H, d).

MP: 206–207° C.

EXAMPLE 15 cis-2-(4-(4-Amino-5-cyanopyrimidin-2-yl)-3,5-dimethyl-piperazin-1-yl)-N-(2-chlorophenyl) acetamide

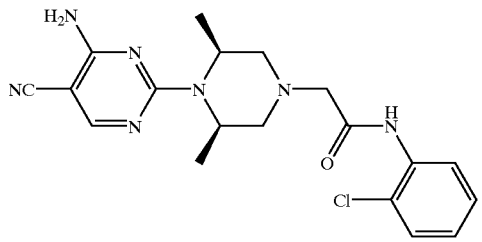

i) 2-Chloro-N-(2-chlorophenyl)acetamide

2-Chloroaniline (5 g) was dissolved in dichloromethane (100 ml) and chloroacetyl chloride (3.11 ml) and N,N-diisopropylethylamine (13.65 ml) were added at 0° C. under a nitrogen atmosphere. The mixture was stirred for 1 hour at 0° C. and 12 hours at room temperature, then quenched with water. The product was extracted with dichloromethane. The organic layer was washed with water, brine, dried (MgSO$_4$) and concentrated under reduced pressure to leave the subtitle product as a beige solid. Yield 7.5 g. This was used in the next step without further purification.

MS: ES(–ve) 203 (M–1,100%)

ii) cis-N-(2-Chlorophenyl)-2-(3,5-dimethylpiperazin-1-yl) acetamide

The product of step (i) (5.9 g) was dissolved in ethanol (50 ml) and cis-2,6-dimethylpiperazine (3 g) and sodium hydrogencarbonate (6.63 g) were added at room temperature under a nitrogen atmosphere. The mixture was heated under reflux for 24 hours and the cooled solution was filtered and the filtrate was evaporated under reduced pressure. The residue was dissolved in 1M HCl (22 ml) and washed with dichloromethane. The aqueous solution was then basified to pH13 with a solution of sodium hydroxide and the product was extracted with dichloromethane. The organic layer was washed with water, brine, collected, dried (MgSO$_4$) and concentrated under reduced pressure to give the subtitle compound as a beige solid. Yield 4 g.

MS: ES(+ve) 282 (M+1,100%)

iii) cis-2-(4-(4-Amino-5-cyanopyrimidin-2-yl)-3,5-dimethylpiperazin-c-yl)-N-(2-chlorophenyl)acetamide A mixture of the product from step (ii) (0.5 g), 4-amino-2-chloro-5-cyanopyrimidine (0.275 g) and N,N-diisopropylethylamine (1.55 ml) in 1-methyl-2-pyrrolidinone (5 ml) was heated under nitrogen at 120° C. for 3 days. The cooled mixture was partitioned between ethyl acetate and water. The organic phase collected was dried (MgSO$_4$) and the solvent evaporated. The crude product purified by silica-gel chromatography eluting with 2% ethyl acetate in isohexane to give the title compound as white solid. Yield 0.1 g.

MS: APCI (+ve) 400 (M+1,100%)

$^1$H NMR: δ (DMSO) 9.67(1H, s), 8.32(1H, dd), 8.29(1H, s), 7.53(1H, dd), 7.37(1H, t), 7.23(2H, brs), 7.15(1H, t), 4.76–4.72(2H, m), 3.23(2H, s), 2.86(2H, d), 2.38(2H, dd), 1.36(6H, d)

EXAMPLE 16 cis-2-(4-Benzenesulphonyl-3,5-dimethylpiperazin-1-yl)-N-(2-chloro-phenyl)acetamide

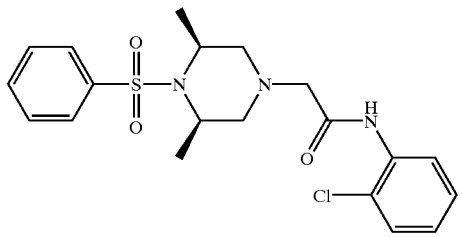

Benzenesulphonyl chloride (0.124 g) was added to a solution of the product from Example 15 step (ii) (0.2 g) in pyridine (2 ml). The mixture was stirred at room temperature for 16 hours and then the solvent was evaporated under reduced pressure. The residue was purified by flash silica-gel chromatography eluting with 1% EtOH, 1% Et$_3$N, 98% CH$_2$Cl$_2$ followed by trituration with ethyl acetate to give the title compound. Yield 0.03 g.

MS: APCI(+ve) 422 (M+1,100%)

$^1$H NMR: δ (CDCl$_3$) 9.49(brs, 1H), 8.48(dd, 1H), 7.82(dd, 2H), 7.60–7.50(m, 3H), 7.37(dd, 1H), 7.30(m, 1H), 7.05(dt, 1H), 4.17(quin, 2H), 3.07(s, 2H), 2.65(d, 2H), 2.15(dd, 2H), 1.55(s, 6H).

MS: 182–3° C.

EXAMPLE 17

(±)-N-(2,6-Dimethylphenyl)-2-[(3-methyl-4-thiazolo(5,4-d)pyrimidin-7-yl)piperazin-1-yl]acetamide

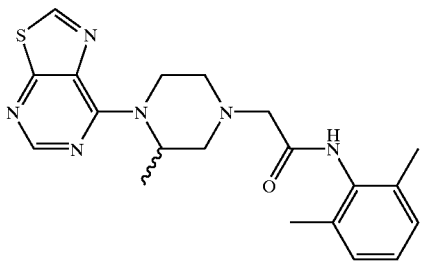

i) (±)-N-(2,6-Dimethylphenyl)-2-(3-methylpiperazin-1-yl)acetamide

The subtitle compound was prepared from 2-chloro-N-(2,6-dimethylphenyl)acetamide (7 g) and (±)-2-methylpiperazine (3.55 g) by the method of Example 15 step (ii) as a white solid. Yield 7 g.

MS: ES(+ve) 262 (M+1,100%)

ii) (±)-N-(2,6-Dimethylphenyl)-2-[(3-methyl-4-thiazolo(5,4-d)pyrimidin-7-yl)piperazin-1-yl]acetamide The title compound was prepared from the product of step (i) (0.381 g) and 7-chloro-thiazolo[5,4,d]pyrimidine (Chem. Pharm. Bull. 1968, (16 (4), 750–755) (0.25 g) by the method of Example 15 step (iii) as a beige solid. Yield 0.01 g.

MS: ES(+ve) 397 (M+1,100%)

$^1$H NMR: δ (CDCl$_3$) 8.84(1H, s), 8.77(1H, s), 8.48(1H, s), 7.18–7.06(3H, m), 3.14(2H, s), 3.88–2.68(7H, brm), 2.26 (6H, s), 1.25(3H, m)

EXAMPLE 18 cis-N-(2-Chlorophenyl)-2-[(3,5-dimethyl-4-quinazolin-4-yl)piperazin-1-yl]acetamide

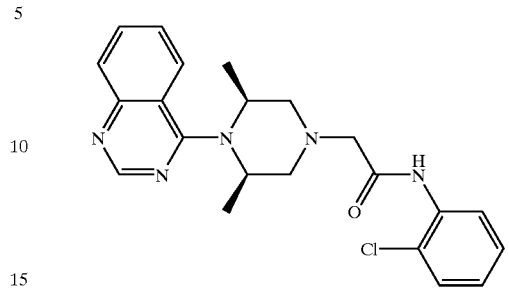

A mixture of the product from Example 15 step (ii) (2.1 g), 4-chloroquinazoline (1.23 g) (J. Chem. Soc., 1944, 619–623) and N,N-diisopropylethylamine (6.15 ml) in 1-methyl-2-pyrrolidinone (14 ml) under nitrogen was heated at 120° C. for 4 days. The cooled mixture was partitioned between ethyl acetate and water. The organic layer was further washed with water, brine, dried (MgSO$_4$) and concentrated under reduced pressure. The residue was purified by silica-gel chromatography eluting with ethyl acetate/isohexane (4:6) to give the title compound as a white solid. Yield 0.08 g.

MS: ES(+ve) 410 (M+1,100%), ES(−ve) 408 (M−1, 1000%)

$^1$H NMR: δ (DMSO) 9.81(1H, s), 8.82(1H, brs), 8.30(1H, dd), 8.18(1H, d), 7.87(2H, d), 7.63–7.58(1H, m), 7.55(1H, dd), 7.38(1H, t), 7.17(1H, t), 4.38(2H, brs), 3.26(2H, s), 2.69(4H, brs), 1.30–1.15(6H, m)

EXAMPLE 19

N-(2-Chlorophenyl)-2-[(8-(thieno[2,3-d]pyrimidin-4-yl)-3,8-diazabicyclo[3.2.1]oct-3-yl]acetamide

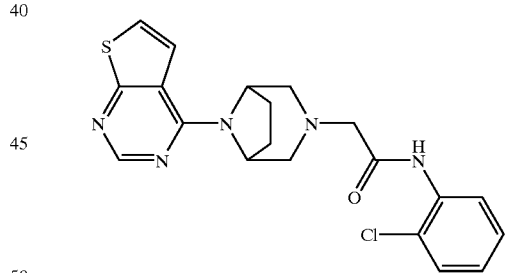

i) 1,1-Dimethylethyl, 3-[(2-chlorophenylcarbamoyl)methyl]-3,8-diaza-bicyclo[3.2.1]octane-8-carboxylate A mixture of 1,1-dimethylethyl, 3,8-diazabicyclo[3.2.1]octane-8-carboxylate (0.048 g) (J. Med. Chem., 1998, 41(5), 674–681), sodium bicarbonate (0.058 g), potassium iodide (0.003 g) and the product of Example 15 step (i) (0.051 g) in ethanol (0.5 ml) was heated at 70° C. for 3 hours. The cooled mixture was partitioned between ethyl acetate and water and the organic phase was washed with water and brine, dried (MgSO$_4$) and the solvent evaporated under reduced pressure. Purification was by flash silica-gel chromatography eluting with 2% EtOH, 1% Et$_3$N, 97%CH$_2$Cl$_2$. Yield 0.068 g.

MS: ES(+ve) 380 (M+1,100%)

ii) N-(2-Chlorophenyl)-2-(3,8-diazabicyclo[3.2.1]oct-3-yl)acetamide trifluoroacetic acid salt The subtitle compound was prepared from the product of step (i) (0.068 g) by the method of Example 1 step (ii) as a white solid. Yield 0.061 g.

MS: ES(+ve) 280 (M+1,100%)

iii) N-(2-Chlorophenyl)-2-[(8-(thieno[2,3-d]pyrimidin-4-yl)-3,8-diazabicyclo[3.2.1]oct-3-yl]acetamide The title compound was prepared from the product of step (ii) (0.061 g) by the method of Example 15 step (iii), with heating for 1 hour only, as a white solid. Yield 0.04 g.

MS: APCI(+ve) 414 (M+1,100%)

$^1$H NMR: δ (CDCl$_3$) 9.65(s, 1H), 8.53(dd, 1H), 8.49(s, 1H), 7.41(dd, 1H), 7.33–7.28(m, 3H), 7.07(t, 1H), 5.02(brs, 1H), 3.18(s, 2H), 2.95(d, 2H), 2.77(d, 2H), 2.32(m, 2H), 2.12(m, 2H).

MS: 164° C.

EXAMPLE 20

N-(2-Methylphenyl)-2-[8-(9-methyl-9H-purin-6-yl)-3,8-diazabicyclo[3.2.1]oct-3-yl]acetamide

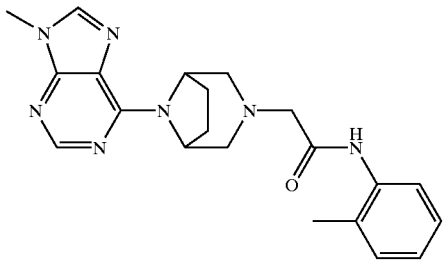

i) 1,1-Dimethylethyl, 3-phenylmethyl-3,8-diazabicyclo[3.2.1]oct-8-carboxylate

3-Phenylmethyl-3,8-diazabicyclo[3.2.1]octane hydrochloride salt (0.115 g) was dissolved in dichloromethane (16 ml) and water (16 ml) and sodium hydrogencarbonate (1.61 g) were added. The mixture was stirred rapidly for 10 minutes at room temperature and then di-tert-butyl dicarbonate (1.15 g) was added in portions. The mixture was stirred rapidly for an additional 2 hours. The organic layer was separated, dried over magnesium sulphate, filtered and concentrated to afford a white crystalline solid. Yield 1.45 g.

MS: ES(+ve) 303 (M+1,100%)

ii) 1,1-Dimethylethyl, 3,8-diazabicyclo[3.2.1]oct-8-carboxylate hydrochloride salt A solution of the product from step (i) (1.45 g) was dissolved in ethyl acetate (12 ml) and cooled at −10° C. under a nitrogen atmosphere. 1M HCl in diethyl ether (4.81 ml) was added dropwise, causing the salt to precipitate out of solution. The mixture was stirred an additional 1 hour and the crystalline product was collected by filtration and dried in a vacuum oven. This white solid was dissolved in methanol (18 ml) and 10% palladium on carbon (0.1 g) added under a nitrogen atmosphere. The mixture was then stirred vigorously under an hydrogen atmosphere for 12 hours. After completion of the reaction, the mixture was filtered through Celite and the mother liquor concentrated to afford the subtitle compound as a white crystalline solid. Yield 1.18 g.

$^1$NMR: δ (CDCl$_3$) 4.34(2H, brs), 3.16(4H, brs), 2.27–2.09 (4H, m), 1.47(9H, s)

iii) 1,1-Dimethylethyl, 3-[(2-methylphenylcarbamoyl)methyl]-3,8-diaza-bicyclo[3.2.1]octane-8-carboxylate A mixture of the product from step (ii) (0.16 g), 2-chloro-N-(2-methyl)acetamide (Synthesis, 1982, (9), 795–796) (0.13 g), sodium hydrogencarbonate (0.16 g), and potassium iodide (8 mg) in ethanol (2 ml) under a nitrogen atmosphere was heated at 70° C. for 4 hours. The reaction mixture was partitioned between ethyl acetate and water. The organic layer was washed with water, brine, dried (MgSO$_4$) and concentrated under reduced pressure. The residue was purified by silica-gel chromatography eluting with 2% ethanol/1% triethylamine in dichloromethane to give the subtitle compound as beige solid. Yield 0.23 g.

MS: ES(+ve) 360 (M+1,100%)

iv) N-(2-Methylphenyl)-2-[3,8-diazabicyclo[3.2.1]oct-3-yl]acetamide, trifluoroacetic acid salt A mixture of the product from step (iii) (0.23 g) in dichloromethane (30 ml) and trifluoroacetic acid (1.80 ml) under a nitrogen at room temperature was stirred for 24 hours. The mixture was concentrated under reduced pressure to leave brown gum. This was used in the next step without further purification.

MS: ES(+ve) 260 (M+1,100%)

v) N-(2-Methylphenyl)-2-[8-(9-methyl-9H-purin-6-yl)-3,8-diazabicyclo[3.2.1]oct-3-yl]acetamide A mixture of the product from step (iv) (0.12 g), 6-chloro-9-methylpurine (0.06 g) (J. Org. Chem., 1983, 48 (6), 850–855), and N,N-disopropylethylamine (1 ml) in 1,4-dioxane (5 ml) were heated together at reflux for 5 hours. The volatiles were removed under reduced pressure and the residue purified by reverse phase HPLC eluting with a gradient from 5% acetonitrile in aqueous 1% ammonium acetate to 75% over 7 min. The title product was obtained, by freeze drying, as a white solid. Yield: 0.027 g.

MS: APCI(+ve) 392 (M+1,100%)

$^1$H NMR: δ (DMSO); 9.16(s, 1H), 8.27(s, 1H), 8.15(s, 1H), 7.75(d, 1H), 7.10(t, 1H), 7.08(t, 1H), 3.74(s, 3H), 5.70(bs, 1H), 5.00(bs, 1H), 3.74(s, 3H), 3.07(s, 2H), 2.90(m, 2H), 2.50–1.80(m, 6H), 2.30(s, 3H)

EXAMPLE 21

2-[8-(9-Methyl-9H-purin-6-yl)-3,8-diazabicyclo[3.2.1]oct-3-yl]-N-(quinolin-5-yl)acetamide

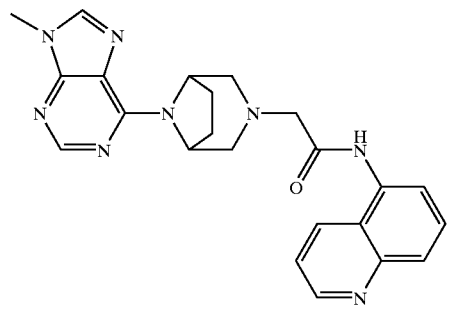

i) 1,1-Dimethlethyl, 3-[(quinolin-5-ylcarbamoyl)methyl]-3,8-diaza-bicyclo[3.2.1]octane-8-carboxylate The subtitle compound was prepared from the product of Example 20 step (ii) (0.24 g) and 2-chloro-N-(quinolin-5-yl)acetamide (J. Indian Chem. Soc, 1940, 17, 619–621) (0.234 g) by the method of Example 20 step (iii) as a pale yellow solid. Yield 0.38 g.

MS: ES(+ve) 397 (M+1,100%)

ii) 2-(3,8-Diazabicyclo[3.2.1]oct-3-yl)-N-(quinolin-5-yl)acetamide, trifluroacetic acid salt The subtitle compound was prepared from the product of step (i) (0.38 g) by the method Example 20 step of step (iv) as a pale yellow gum. This was used directly in the next step.

MS: ES(+ve) 297 (M+1,100%)

iii) 2-[8-(9-Methyl-9H-purin-6-yl)-3,8-diazabicyclo[3.2.1oct-3-yl]-N-(quinolin-5-yl)acetamide A mixture of the product from step (ii) (0.20 g), 6-chloro-9-methylpurine (0.1 g) (J. Org. Chem., 1983, 48 (6), 850–855), and N,N-disopropylethylamine (1 ml) in 1,4-dioxane (5 ml) were heated together at reflux for 4 hours. The volatiles were removed under reduced pressure and the residue purified by reverse phase HPLC eluting with a gradient from 5% acetonitrile in aqueous 1% ammonium acetate to 75% over 7 min. The title product was obtained, by freeze drying, as a white solid. Yield: 0.047 g.

MS: APCI(+ve) 429 (M+100%), APCI(−ve) 427 (M−1, 100%)

$^1$H NMR: δ (DMSO); 9.9(bs, 1H), 8.90(m, 1H), 8.40(d, 1H), 8.30(s, 1H), 8.18(s, 1H), 7.90(d, 1H), 7.80(d, 1H), 7.75(t, 1H), 7.60(m, 1H), 5.78(bs, 1H), 5.00(bs, 1H), 3.78(s, 3H), 3.30(s, 2H), 2.90(m, 2H), 2.70–1.80(m, 6H).

EXAMPLE 22

N-(Quinolin-5-yl)-2-[8-thiazolo [5,4-d]pyrimidin-7-yl)-3,8-diazabicyclo[3.2.1]oct-3-yl]acetamide

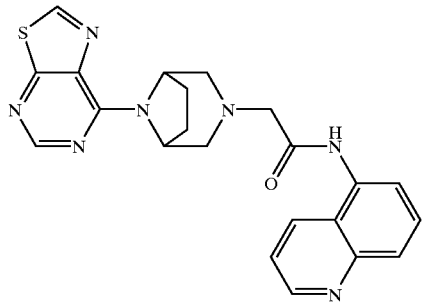

The title compound was prepared from the product Example 21 step (ii) (0.1 g) and 7-chlorothiazolo[5,4-d]pyrimidine (Chem. Pharm. Bull, 1968, 16(4), 750–755) (0.06 g) by the method of Example 21 step (iii) as a pale yellow solid. Yield 0.1 g.

MS: ES(+ve) 432 (M+1,100%)

$^1$H NMR: δ (CDCl$_3$) 9.62(1H, s), 8.99–8.98(1H, m), 8.77(1H, s), 8.50(1H, s), 8.26(1H, d), 8.16(1H, d), 7.99(1H, d), 7.75(1H, t), 7.52–7.49(1H, m), 6.04(1H, brs), 5.29(1H, brs), 3.27(2H, s), 3.03(2H, d), 2.83(2H, brs), 2.22(2H, brs), 1.70(1H, brs), 1.45(1H, dd)

EXAMPLE 23

N-(2-Methylphenyl)-2-[(8-thiazolo[5,4-d]pyrimidin-7-yl)-3,8-diazabicyclo[3.2.1]oct-3-yl]acetamide

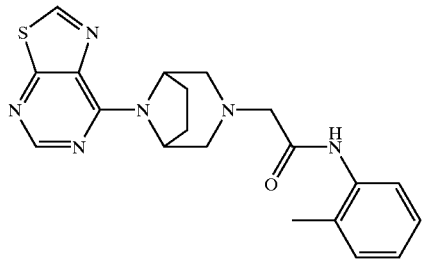

The title compound was prepared from the product of Example 20 step (iv) (0.1 g) and 7-chlorothiazolo[5,4-d]pyrimidine (Chem. Pharm. Bull, 1968, 16 (4), 750–755) (0.06 g) by the method of Example 21 step (iii) as a white solid. Yield 0.06 g.

MS: ES(+ve) 395 (M+1,100%)

$^1$H NMR: δ (CDCl$_3$) 8.99(1H, s), 8.75(1H, s), 8.48(1H, s), 8.08(1H, d), 7.27–7.21(2H, m), 7.08(1H, t), 6.00(1H, brs), 5.29(1H, brs), 3.15(2H, s), 2.95(2H, d), 2.74(2H, brs), 2.38(3H, s), 2.27–2.07(4H, m)

EXAMPLE 24

N-(2-Methyl-S-(methylsulphonyl)amidophenyl)-2-[8-(9-methyl-9H-purin-6-yl)-3,8-diazabicyclo[3.2.1]oct-3-yl]acetamide

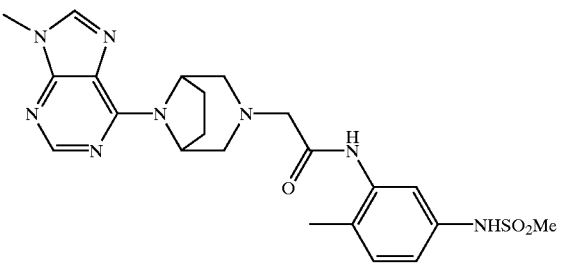

i) 2-Chloro-N-(5-bis(methylsulphonyl)amido-2-methylphenyl)acetamide

A mixture of the product from step (ii) (0.62 g) and N,N-diisopropylethylamine (1.04 ml) in dichloromethane (40 ml) at 10° C. was treated with chloroacetyl chloride (0.19 ml) dropwise. After stirring for 4 hours the mixture was poured into saturated sodium bicarbonate solution and the organic phase collected and further washed with brine, collected, dried (CaCl$_2$) and solvent evaporated under reduced pressure to leave a yellow gum. This was purified by silica-gel chromatography eluting with 10% diethyl ether in dichloromethane to give the subtitle product as a white solid. Yield 0.71 g.

MS: APCI (−ve) 353 (M−1,100%)

ii) 1,1-Dimethylethyl, 3-[(5-bis(methylsulphonyl)amido-2-methyl phenylcarbamoyl)methyl]-3,8-diazabicyclo[3.2.1]octane-8-carboxylate The subtitle compound was prepared from the product of step (i) (0.266 g) and the product from Example 20 step (ii) (0.2 g) by the method of Example 20 step (iii) as a white solid. Yield 0.45 g.

MS: ES(+ve) 531 (M+1,100%)

iii) 2-(3,8-Diazabicyclo[3.2.1]oct-3-yl)-N-[5-bis(methylsulphonyl)amido-2-methylphenyl]acetamide, trifluoroacetic acid salt The subtitle compound was prepared from the product of step (ii) (0.45 g) by the method of Example 20 step (iv) as a white solid. Yield 0.42 g.

MS: ES(+ve) 431 (M+1,100%)

iv) N-[5-Bis(methylsulphonyl)amido-2-methylphenyl]-2-[8-(9-methyl-9H-purin-6-yl)-3,8-diazabicyclo[3.2.1]oct-3-yl]acetamide The subtitle compound was prepared from the product of step (iii) (0.2 g) and 6-chloro-9-methylpurine (J. Org. Chem., 1983, 48(6), 850–855) (0.1 g) by the method of Example 20 step (v) as white solid. Yield 0.1 g.

MS: ES(+ve) 563 (M+1,100%)

v) N-(2-Methyl-5-(methylsulphonyl)amidophenyl)-2-[8-(9-methyl-9H-purin-6-yl)-3,8-diazabicyclo[3.2.1]oct-3-yl]acetamide A mixture of the product from step (iv) (0.1 g) and sodium bicarbonate (0.05 g) in wet ethanol (2 ml) was heated at reflux for 1.5 hours, cooled and filtered. Purification was by flash silica-gel chromatography eluting with 2.5% EtOH, 1% aq. NH$_3$, 96.5% CH$_2$Cl$_2$ followed by trituration with ethyl acetate to give the title product as a white solid. Yield 0.066 g.

MS: AP(+ve) 485 (M+1,100%)

$^1$H NMR: δ (CDCl$_3$): 9.19(s, 1H), 8.40(s, 1H), 8.14(d, 1H), 7.74(s, 1H), 7.20(d, 1H), 7.12(dd, 1H), 7.08(s, 1H), 3.84(s, 3H), 3.17(s, 2H), 2.97(s, 3H), 2.90(d, 2H), 2.75(d, 2H), 2.37(s, 3H), 2.15(brm, 4H).

MS: 216–217° C.

EXAMPLE 25

N-[2-Methyl-5-(methylsulphonyl)amidophenyl]-2-[(8-thiazolo[5,4-d]pyrimidin-7-yl)-3,8-diazabicyclo[3.2.1]oct-3-yl]acetamide

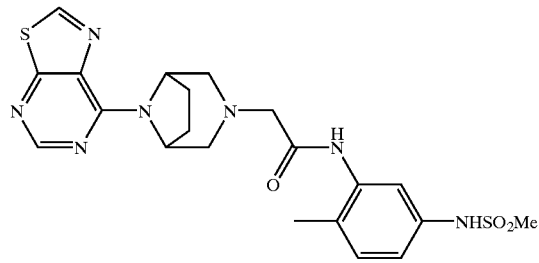

i) N-[5-Bis(methylsulphonyl)amido-2-methylphenyl]-2-[(8-thiazolo[5,4-d]pyrimidin-7-yl)-3,8-diazabicyclo[3.2.1]oct-3-yl]acetamide The subtitle compound was prepared from the product of Example 24 step (iii) (0.21 g) and 7-chloro-thiazolo[5,4-d] pyrimidine (Chem. Pharm. Bull, 1968, 16 (4), 750–755) (0.069 g) by the method of Example 20 step (v) as a white solid. Yield 0.113 g.

MS: APCI(+ve) 566 (M+1,100%)

ii) N-[2-Methyl-5-(methylsulphonyl)amidophenyl]-2-[(8-thiazolo[5,4-d]pyrimidin-7-yl)-3,8-diazabicyclo[3.2.1]oct-3-yl]acetamide The title compound was prepared from the product of step (i) (0.113 g) by the method of Example 24 step (v) as a white solid. Yield 0.085 g.

MS: APCI(+ve) 488 (M+1,100%)

$^1$H NMR: δ (CDCl$_3$) 9.18(s, 1H), 8.76(s, 1H), 8.48(s, 1H), 8.17(d, 1H), 7.31(s, 1H), 7.20(d, 1H), 7.13(dd, 1H), 3.21(s, 2H), 2.95(s, 3H), 2.92(m, 2H), 2.76(m, 2H), 2.38(s, 3H), 2.17(brm, 4H).

MP: 145–187° C.

EXAMPLE 26

N-[2-Methyl-5-(methylsulphonyl)amidophenyl]-2-[4-(thieno[2,3-d]pyrimidin-4-yl)-3,8-diazabicyclo[3.2.1]oct-3-yl]acetamide

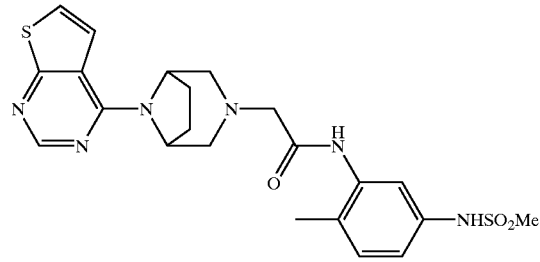

i) N-[(5-Bis(methylsulphonyl)amido-2-methylphenyl]-2-[4-(thieno[2,3-d]pyrimidin-4-yl)-3,8-diazabicyclo[3.2.1]oct-3-yl]acetamide The subtitle compound was prepared from the product of Example 24 step (iii) (0.216 g) and 4-chlorothieno[2,3-d]pyrimidine (0.056 g) by the method of Example 20 step (v) as a white solid. Yield 0.13 g.

MS: ESI (+ve) 565 (M+1,100%)

ii) N-[2-Methyl-5-(methylsuphonyl)amidophenyl-2-[4-(thieno[2,3-d]pyrimidin-4-yl)-3,8-diazabicyclo[3.2.1]oct-3-yl]acetamide The title compound was prepared from the product of step (i) (0.130 g) by the method of Example 24 step (v) as a white solid. Yield 0.025 g.

MS: APCI(+ve) 487 (M+1,100%)

$^1$H NMR: δ (DMSO) 9.18(1H, s), 8.38(1H, s), 7.71–7.62 (3H, m), 7.17(1H, d), 6.93(1H, dd), 5.04(2H, brs), 3.12(2H, s), 2.93(3H, s), 2.90(2H, d), 2.58(2H, d), 2.23(3H, s), 2.13(2H, d), 1.98–1.95(2H, m)

EXAMPLE 27

Cis-2-(3,5-Dimethyl-4-(thieno[2,3-d]pyrimidin-4-yl) piperazin-1-yl)-N-(2-methyl-5-(1-piperazinylmethyl) phenyl)acetamide, hydrochloride salt

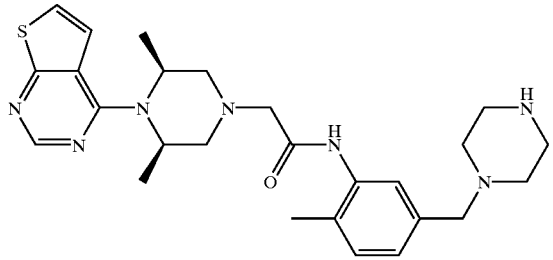

i) 1,1-Dimethylethyl, 4-((4-methyl-3-nitrophenyl)methyl) piperazine-1-carboxylate A mixture of 4-methyl-3-nitrobenzyl chloride (5.55 g), 1,1-dimethylethyl, piperazine-1-carboxylate (5.6 g), N,N-diisopropylethylamine (5 ml) in N,N-dimethylformamide (25 ml) were heated at 110° C. for 3 h. After cooling to ambient temperature the mixture was partitioned between dichloromethane and water. The organic phase collected, dried (MgSO$_4$) and solvent evaporated under reduced pressure to leave the subtitle compound as a pale yellow oil. Yield: 9.6 g MS: APCI(+ve) 336 (M+1)

ii) 1,1-Dimethylethyl, 4-((3-amino-4-methylphenyl)methyl)piperazine-1-carboxylate The product from step (i) (9.6 g), 10% palladium on charcoal (100 mg) in ethanol (100 ml) was stirred under an atmosphere of hydrogen gas for 24 h. The catalyst was filtered through celite and the mother liquor collected and solvent evaporated under reduced pressure to give the subtitle compound as a pale yellow oil. Yield. 9 g MS: APCI(+ve) 322 (M+1)

iii) cis-2-(3,5-Dimethyl-4-(thieno[2,3-d]pyrimidin-4-yl)piperazin-1-yl-N-(2-methyl-5-((4-(1,1-dimethylethyloxycarbonyl)piperazin-1-yl)methyl)phenyl)acetamide The product from Example 9 step (ii) (0.21 g), the product from step (ii) (0.15 g), benzotriazol-1-yl-oxy-tripyrrolidinophosphonium hexfluorophosphate (PyBrop) (0.24 g), N,N-diisopropylethylamine (0.36 ml) in dry N,N-dimethylformamide were stirred together under nitrogen for 20 h. The mixture was poured into water and the resulting precipitate filtered as an off white solid. Purification was by silica gel chromatography eluting with ethyl acetate to give the subtitle compound as a white solid. Yield: 0.21 g MS: APCI (+ve) 594 (M+1)

iv) Cis-2-(3,5-Dimethyl-4-(thieno[2,3-d]pyrimidin-4-yl)piperazin-1-yl)-N-(2-methyl-5-(1-piperazinylmethyl)phenyl)acetamide, hydrochloride salt The product from step (iii) (0.17 mg) was dissolved in 4M hydrogen chloride in 1,4-dioxane (2 ml). After 48 h the solvents were evaporated under reduced pressure to leave the title compound as a white solid. Yield: 0.16 g MS: APCI (+ve) 494 (M+1)

$^1$H NMR: δ (DMSO) 8.50(s, 1H), 7.78(s, 1H), 7.65(d, 1H), 7.58(d, 1H), 7.39(d, 1H), 7.31(d, 1H), 5.25(m, 1H), 5.05(bs, 2H), 4.23(s, 2H), 3.77(bs, 2H), 3.43(s, 4H), 3.18(m, 6H), 3.04(m, 2H), 2.71(s, 1H), 2.30(s, 3H), 1.47(d, 6H)

EXAMPLE 28

N-(2-Methylphenyl)-2-[(8-(thieno[2,3-d]pyrimidin-4-yl)-3,8-diazabicyclo[3.2.1]oct-3-yl]acetamide

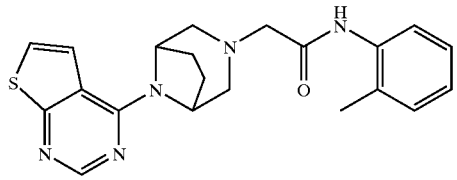

The title compound was prepared from the product of Example 20 step (iv) (0.45 g) and 4-chloro-thieno[2,3-d]pyrimidine by the method of Example 1 step (i). Yield: 0.22 g.

MS: APCI(+ve) 394 (M+1)

$^1$H NMR: δ (DMSO) 9.17(1H, brs), 8.39(1H, s), 7.73–7.62(3H, m), 7.25–7.15(2H, m), 7.07(1H, m), 5.05(2H, brs), 3.12(2H, s), 2.92(2H, d), 2.58(2H, d), 2.28(3H, s), 2.15(2H, m), 1.97(2H, m).

EXAMPLE 29

N-[5-Methanesulphonylamido-2-methylphenyl)-2-[8-(thieno[2,3-d]pyrimidin-4-yl)-8-azabicyclo[3.2.1]oct-3-yl]acetamide

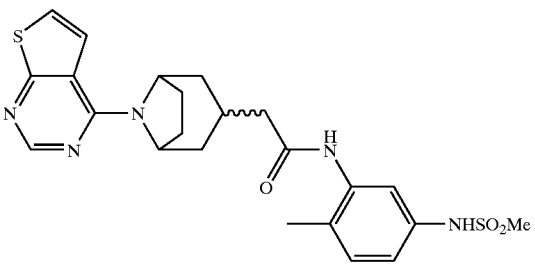

i) Ethyl, 2-(8-(thieno[2,3-d]pyrimidin-4-yl)-8-azabicyclo[3.2.1]oct-3-yl)ethanoate Ethyl, 2-(8-azabicyclo[3.2.1]oct-3-yl)ethanoate (0.64 g) (Arch. Pharm., 1976, 309 (6), 447. Arch. Pharm., 1975, 308(5), 365), 4-chlorothieno[2,3-d]pyrimidine (0.55 g), N,N-diisopropylethylamine (1.7 ml) in 1,4-dioxane (10 ml) were heated at 105° C. for 4 h. The precipitate was filtered and the mother liquor collected, the solvent evaporated under reduced pressure to leave a brown oil. Purification was by silica gel chromatography eluting with ethyl acetate/isohexane (3:7) to give the subtitle compound as a colourless oil. Yield: 0.35 g.

MS: APCI(+ve) 332 (M+1)

ii) 2-(8-(Thieno[2,3-d]pyrimidin-4-yl)-8-azabicyclo[3.2.1]oct-3-yl)ethanoic acid The product from step (i) (0.14 g) in ethanol (0.3 ml) was treated with 1N sodium hydroxide (0.6 ml) at ambient temperature for 48 h. The mixture was acidified to pH 4 with 2N hydrochloric acid and the solvents evaporated under reduced pressure. The residue was treated with ethanol (5 ml) and inorganic salts filtered. The mother liquor collected and solvent evaporated under reduced pressure to leave a gummy residue. Purification was by trituration with diethyl ether. Yield: 0.097 g MS: APCI(+ve) 304 (M+1)

iii) N-[5-bis((Methanesulphonyl)amido-2-methylphenyl)-2-[8-(thieno[2,3-d]pyrimidin-4-yl)-8-azabicyclo[3.2.1]oct-3-yl]acetamide The product from step (ii) (0.097 g), the product from Example 11 step (ii) (0.089 g), benzotriazol-1-yl-oxy-tripyrrolidinophosphonium hexfluorophosphate (PyBrop) (0.16 g), 4-N,N-dimethylaminopyridine (0.04 g), N,N-diisopropylethylamine (0.28 ml) in dichloromethane (10 ml) were stirred at ambient temperature for 48 h. The mixture was partitioned between water and dichloromethane. The organic phase collected, dried (MgSO$_4$) and solvent evaporated under reduced pressure. Purification was by reverse phase HPLC eluting with 1% aq. ammonium acetate/acetonitrile (90% to 50%) to give the subtitle compound as a white solid. Yield: 0.1 g MS: APCI (+ve) 564 (M+1)

iv) N-[5-(Methanesulphonylamido-2-methylphenyl)-2-[8-(thieno[2,3-d]pyrimidin-4-yl)-8-azabicyclo[3.2.1]oct-3-yl]acetamide The product from step (iii) (0.1 g), potassium carbonate (0.14 g), water (5 ml) and 1,4-dioxane (5 ml) were heated at 110° C. for 1 h. The mixture was treated with acetic acid (2 ml) and solvents evaporated under reduced pressure. Purification was by silica gel chromatography eluting with ethyl acetate to give the title compound as a white solid. Yield: 0.011 g MS: APCI (+ve) 486 (M+1)

$^1$H NMR: δ (DMSO) 9.33(bs, 1H), 9.16(bs, 1H), 8.38(2 3 3 s, 1H), 7.6(m, 3H), 7.30(m, 1H), 7.15(t, 1H), 6.90(m, 1H), 5.0(bm, 2H), 2.90(s, 3H), 2.30–1.89(bm, 4H), 2.10(s, 3H), 1.5–0.9(bm, 2H)

EXAMPLE 30

N-(2-Methyl-5-(1-piperazinylmethyl)phenyl)-2-[(8-(thieno[2,3-d]pyrimidin-4-yl)-3,8-diazabicyclo[3.2.1]oct-3-yl]acetamide

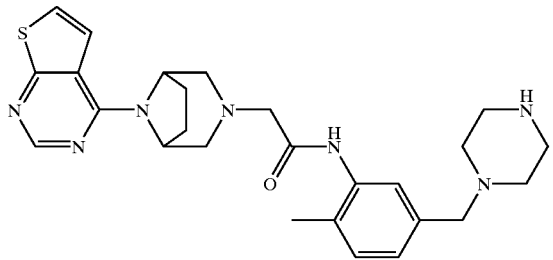

i) Methyl, 2-(8-(1,1-dimethylethyloxycarbonyl)-3,8-diazabicyclo[3.2.1]oct-3-yl)acetate A mixture of 1,1-dimethylethyl, 3,8-diazabicyclo[3.2.1] oct-8-carboxylate (0.35 g), sodium bicarbonate (84 mg), potassium iodide (20 mg) and methyl bromoacetate (355 mg) in ethanol (5 ml) were heated at 70° C. for 6 h. The reaction mixture was partitioned between ethyl acetate and water. The organic phase collected, dried (MgSO$_4$) and the solvent evaporated under reduced pressure to leave the subtitle compound as a pale yellow solid. Yield: 380 mg $^1$H NMR: δ (DMSO) 4.01(bs, 2H), 3.58(s, 2H), 3.29(s, 3H), 2.62–2.49(m, 4H), 1.82–1.64(m, 4H), 1.40(s, 9H)

ii) Methyl, 2-(3,8-diazabicyclo[3.2.1]oct-3-yl)acetate, trifluoroacetic acid salt The subtitle compound was prepared from the product of step (i) (380 mg) by the method of Example 1 step (ii). The product was used without further purification directly in next step.

iii) Methyl, 2-(8-(thieno[2,3-d]pyrimidin-4-yl)-(3,8-diazabicyclo[3.2.1]oct-3-yl)acetate The subtitle compound was prepared from the product of step (ii) (400 mg) and 4-chloro-thieno[2,3-d]pyrimidine (288 mg), N,N-diisopropylethylamine (232 ul) in 1,4-dioxane at 100° C. for 48 h. Solvent was evaporated under reduced pressure. Purification was by silica gel chromatography eluting with 2% ethanol in dichloromethane to give the subtitle compound as a beige solid. Yield: 170 mg.

MS: APCI (+ve) 319 (M+1, 100%)

iv) 2-(8-(Thieno[2,3-d]pyrimidin-4-yl)-(3,8-diazabicyclo[3.2.1]oct-3-yl)acetic acid The product from step (iii) (170 mg) was dissolved in ethanol (1 ml) and treated with 1N sodium hydroxide solution (0.8 ml) at room ambient temperature. After 3 h the mixture was acidified with 2M hydrochloric acid to pH4. The solvents were then evaporated under reduced pressure and the residue treated with ethanol and filtered to remove inorganic salts. The mother liquor was collected and evaporated under reduced pressure to leave the subtitle compound as a white solid. Yield: 160 mg.

MS: APCI(+ve) 305 (M+1)

v) N-(5-(4-(1,1-Dimethylethyloxycarbonyl)piperazin-1-ylmethyl)-2-methyl)phenyl)-2-[(8-(thieno[2,3-d]pyrimidin-4-yl)-3,8-diazabicyclo[3.2.1]oct-3-yl]acetamide The product of step (iv) (83 mg), the product of Example 27 step (ii) (92 mg), benzotriazol-1-yl-oxy-tripyrrolidinophosphonium hexafluorophosphate (PyBrop) (153 mg) and N,N-diisopropylethylamine (95 ul) were stirred in N,N-dimethylformamide (5 ml) at ambient temperature for 12 h. The solvents were evaporated under reduced pressure and purification was by silica gel chromatography eluting with iso-hexane/acetone (7:3) containing 1% triethylamine to give the subtitle compound as a white solid. Yield: 40 mg.

$^1$H NMR δ (DMSO) 9.15(s, 1H), 8.38(s, 1H), 7.67–7.66 (m, 2H), 7.17(d, 1H), 7.00(d, 1H), 5.04(bs, 2H), 3.41(s, 2H), 3.29(s, 4H), 3.11(s, 2H), 2.90(d, 2H), 2.29(t, 4H), 2.24(s, 3H), 2.14(d, 2H), 2.00–1.93(m, 2H), 1.38(s, 9H)

vi) N-(2-Methyl-5-(1-piperazinylmethyl)phenyl)-2-[(8-(thieno[2,3-d]pyrimidin-4-yl)-3,8-diazabicyclo[3.2.1]oct-3-yl]acetamide The title compound was prepared from the product of step (v) (35 mg) by the method of Example 8 step (iv) as a white solid. Yield: 35 mg MS: APCI(+ve) 492 (M+1)

$^1$H NMR: δ (DMSO) 9.66(bs, 1H), 8.53(s, 1H), 7.75(s, 2H), 7.63(bs, 1H), 7.42(d, 1H), 7.33(d, 1H), 5.21(bs, 2H), 4.33(bs, 2H), 3.79–3.13(bm, 10H), 2.40–2.26(bm, 4H), 2.23 (s, 3H), 2.20–2.10(bm, 4H).

EXAMPLE 31

Cis-N-(5-(2-Aminoethoxy)-2-methyl-phenyl)-2-(3,5-dimethyl-4-(thieno[2,3-d]pyrimidin-4-yl)piperazin-1-yl)acetamide, hydrochloride salt

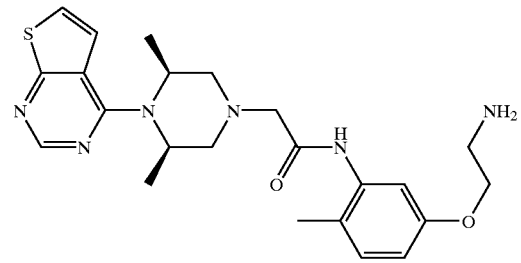

i) 1,1-Dimethylethyl, 2-(4-methyl-3-nitro-phenoxy) ethylamino-1-carboxylate

The subtitle compound was prepared from 4-methyl-3-nitrophenol (2 g) and 1,1-dimethylethyl, 2-hydroxyethylamino-1-carboxylate (2.5 g) by the method of Example 50 step (i) as a beige solid. Yield: 3 g $^1$H NMR δ (CDCl$_3$) 7.50(s, 1H), 7.22(d, 1H), 7.05(dd, 1H), 4.96(bs, 1H), 4.07(t, 2H), 3.56(q, 2H), 2.52(s, 33H), 1.46(s, 9H)

ii) 1,1-Dimethylethyl, 2-(3-amino-4-methyl-phenoxy) ethylamino-1-carboxylate

The subtitle compound was prepared from the product of step (i) (1 g) by the method of Example 50 step (ii) as an off white solid. Yield: 0.9 g MS: APCI (+ve) 267 (M+1)

iii) cis-N-(5-(2-(1,1-Dimethylethyloxycarbonylaminoethoxy))-2-methyl-phenyl)-2-(3,5-dimethyl-4-(thieno[2,3-d]pyrimidin-4-yl) piperazin-1-yl)acetamide The product of Example 9 step (ii) (0.54 g), the product from step (ii) (0.35 g), benzotriazol-1-yl-oxy-tripyrrolidinophosphonium hexafluorophosphate (PyBrop) (0.59 g), N,N-diisopropylethylamine (0.8 ml) in dry N,N-dimethylformamide (15 ml) were stirred together under nitrogen for 24 h. The mixture was poured onto water (50 ml) and the resulting precipitate filtered as a pale yellow solid. Purification was by silica gel chromatography eluting with diethyl ether/ethyl acetate (9:1) as eluant to give the subtitle compound as a white solid. Yield: 0.51 g MS: APCI(+ve) 555 (M+1)

iv) Cis-N-(5-(2-Aminoethoxy)-2-methyl-phenyl)-2-(3,5-dimethyl-4-(thieno[2,3-d]pyrimidin-4-yl)piperazin-1-yl)acetamide, hydrochloride salt The title compound was prepared from the product of step (iii) (0.42 g) according to the method of Example 27 step (iv) as a white solid. Yield: 0.36 g MS: APCI(+ve) 455 (M+1)

$^1$HNMR δ (DMSO) 9.57(bs, 1H), 8.50(s, 1H), 8.15(bs, 2H), 7.65(d, 1H), 7.57(d, 1H), 7.37(s, 1H), 7.15(d, 1H), 6.75(dd, 1H), 5.05(bs, 2H), 4.17(t, 2H), 3.77(bs, 2H), 3.27 (d, 2H), 3.19(d, 2H), 3.00(bs, 2H), 2.22(s, 3H), 1.48(d, 6H)

EXAMPLE 32

Cis-N-(5-(2-(N-Methylamino)ethoxy)-2-methyl-phenyl)-2-(3,5-dimethyl-4-(thieno[2,3-d]pyrimidin-4-yl)piperazin-1-yl)acetamide, hydrochloride salt

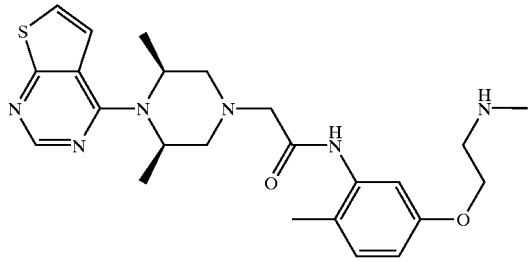

i) 1,1-Dimethylethyl, 2-(4-methyl-3-nitro-phenoxy)ethyl(N-methylamino)-1-carboxylate The subtitle compound was prepared from 4-methyl-3-nitrophenol (0.5 g) and 1,1-dimethylethyl, 2-hydroxyethyl-(N-methylamino)-1-carboxylate (0.69 g) by the method of Example 50 step (i) as a beige solid. Yield: 0.67 g $^1$H NMR δ (CDCl$_3$) 7.5(s, 1H), 7.24(d, 1H), 7.61(dd, 1H), 4.12(bs, 2H), 3.64(t, 2H), 2.98(s, 3H), 2.53(s, 3H), 1.46(s, 9H)

ii) 1,1-Dimethylethyl, 2-(3-amino-4-methyl-phenoxy)ethyl(N-methylamino)-1-carboxylate The subtitle compound was prepared from the product of step (i) (1 g) by the method of Example 50 step (ii) as an off white solid. Yield: 0.95 g MS: APCI (+ve) 281 (M+1)

iii) N-(5-(2-(1,1-Dimethylethoxycarbonyl(N-methylamino)ethoxy))-2-methyl-phenyl)-2-(3,5-dimethyl-4-(thieno[2,3-d]pyrimidin-4-yl)piperazin-1-yl)acetamide The subtitle compound was prepared from the product of Example 9 step (ii) (0.26 g), the product of step (ii) (0.175 g) by the method of Example 31 step (iii). Purification was by silica gel chromatography eluting with diethyl ether/ethyl acetate (9:1) as eluant to give the subtitle compound as a white solid. Yield: 0.25 g MS: APCI(+ve) 569 (M+1)

iv) cis-N-(5-(2-(N-Methylamino)ethoxy)-2-methyl-phenyl)-2-(3,5-dimethyl-4-(thieno[2,3-d]pyrimidin-4-yl)piperazin-1-yl)acetamide, hydrochloride salt The title compound was prepared from the product of step (iii) (0.189 g) by the method of Example 27 step (iv) as a white solid. Yield: 0.077 g MS: APCI(+ve) 469 (M+1)

$^1$HNMR δ (DMSO) 9.50(bs, 1H), 9.00(bs, 1H), 8.49(s, 1H), 7.64(d, 1H), 7.57(d, 1H), 7.39(s, 1H), 7.17(d, 1H), 6.76(d, 1H), 5.05(bs, 2H), 4.24(s, 2H), 3.22–3.30(m, 4H), 2.95(bs, 2H), 2.62(s, 2H), 2.22(s, 3H), 1.48(d, 6H)

EXAMPLE 33

Cis-N-(5-(2-(N-Methylamino)ethoxy)-2-methyl-phenyl)-2-(4-benzenesulphonyl)-3,5-dimethyl)piperazin-1-yl)acetamide

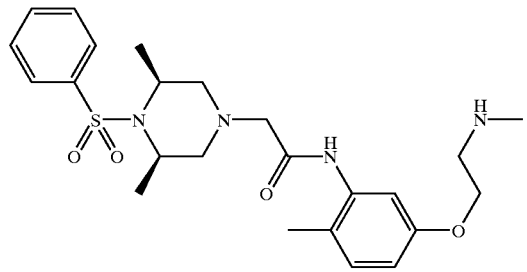

i) cis-1,1-Dimethylethyl, (4-benzenesulphonyl-3,5-dimethyl)piperazine-1-carboxylate A of solution of cis-1,1-dimethyl, 3,5-dimethylpiperazine-1-carboxylate (5 g) in pyridine (60 ml) was treated with benzene sulphonyl chloride (3 ml). After 48 h the solvent was evaporated under reduced pressure and purification of the residue was by silica gel chromatography eluting with ethyl acetate containing 1% triethylamine to give the subtitle compound as a yellow solid. Yield: 5 g MS: APCI(+ve) 255 (M−99)

ii) cis-1-Benzenesulphonyl-3,5-dimethylpiperazine, trifluoroacetic acid salt

The subtitle compound was prepared from the product of step (i) (5 g) by the method Example 1 step (ii). Purification was by recrystallisation from ethanol. Yield: 2 g MS: APCI(+ve) 255 (M+1)

ii) Cis-2-chloro-N-[5-(2-(1,1-dimethylethoxycarbonyl)-N-methylamino)ethoxy)-2-methyl-phenyl]acetamide A solution of the product from Example 32 step (ii) (0.65 g), N,N-diisopropylethylamine (1 ml) in dichloromethane (30 ml) at 0° C. under nitrogen was treated with chloroacetyl chloride (202 ul). After 2 h the mixture was partitioned with water and the product extracted into dichloromethane. The organic phase collected, dried (MgSO$_4$) and solvent removed under reduced pressure to give the subtitle compound as a beige foam. Yield: 0.9 g MS: APCI (−ve) 355 (M−1)

iv) Cis-N-(5-(2-((1,1-dimethylethoxycarbonyl)-N-methylamino)ethoxy)-2-methyl-phenyl)-2-(4-benzenesulphonyl)-3,5-dimethyl)piperazin-1-yl)acetamide The product of step (ii) (100 mg), sodium bicarbonate (99 mg), potassium iodide (5 mg) in ethanol (6 ml) was treated with the product of step (iii) at 70° C. for 12 h. The mixture was partitioned between ethyl acetate and water. The organic phase collected, dried (MgSO$_4$) and solvent evaporated under reduced pressure. Purification was by silica gel chromatography eluting with iso-hexane/acetone (7:3) containing 1% triethylamine to give the subtitle compound as a white solid. Yield: 126 mg MS: APCI(+ve) 575 (M+1), APCI(−ve) 573 (M−1)

v) Cis-N-(5-(2-(N-Methylamino)ethoxy)-2-methyl-phenyl)-2-(4-benzenesulphonyl)-3,5-dimethyl)piperazin-1-yl)acetamide, hydrochloride salt The title compound was prepared from the product of step (iv) (120 mg) by the method of Example 27 step (ii) as a white solid. Yield: 107 mg MS: APCI(+ve) 475 (M+1), APCI (−ve) 473 (M−1)

¹H NMR δ (DMSO) 9.01(bs, 2H), 7.85(d, 2H), 7.69(t, 1H), 7.62(t, 2H), 7.30(bs, 1H), 7.15(d, 1H), 6.74(dd, 1H), 4.18(t, 4H), 4.01(bs, 2H), 3.56(s, 2H), 3.31–3.25(m, 2H), 2.61–2.58(m, 3H), 2.50(m, 2H), 2.15(s, 3H), 1.44(d, 6H)

EXAMPLE 34

Cis-N-15-(2-Aminoethoxy)-2-methyl-phenyl)-2-(4-benzenesulphonyl-3,5-dimethyl)piperazin-1-yl] acetamide, hydrochloride salt

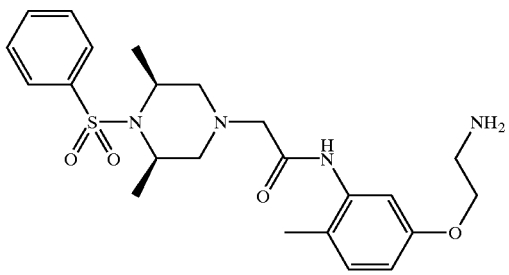

i) Cis-2-chloro-N-[5-(2-(1,1-dimethylethyloxycarbonyl)amino)ethoxy-2-methyl-phenyl]acetamide The subtitle compound is prepared from the product of Example 31 step (ii) (650 mg) and chloroacetyl chloride (213 ul) by the method of Example 33 step (iii) as a beige foam. Yield: 900 mg MS: APCI(–ve) 341 (M–1)

ii) Cis-N-[5-(2-(1,1-Dimethylethoxycarbonyl)amino)ethoxy-2-methyl-phenyl)-2-(4-benzenesulphonyl-3,5-dimethyl)piperazin-1-yl]acetamide The subtitle compound was prepared from the product of step (i) (148 mg) and the product of Example 33 step (ii) by the method of Example 33 step (iv) as a pale yellow solid. Yield: 150 mg.

MS: APCI(+ve) 561 (M+1), APCI (–ve) 559 (M–1)

iii) Cis-N-[5-(2-(Aminoethoxy)-2-methyl-phenyl)-2-(4-benzenesulphonyl-3,5-dimethyl)piperazin-1-yl]acetamide, hydrochloride salt The title compound was prepared from the product of step (ii) (150 mg) by the method Example 27 step (iv) as a white solid. Yield: 150 mg MS: APCI (+ve) 461 (M+1), APCI (–ve) 459 (M–1)

¹H NMR δ (DMSO) 8.13(bs, 2H), 7.85(d, 2H), 7.70–7.59 (m, 3H), 7.32(bs, 1H), 7.14(d, 1H), 6.73(dd, 1H), 4.16(bs, 2H), 4.10(t, 2H), 3.56(s, 2H), 3.19(d, 2H), 3.10–3.03(m, 2H), 2.50(m, 2H), 2.15(s, 3H), 1.43(d, 6H)

EXAMPLE 35

N-(2-Oxo-2,3-dihydro-1H-indol-4-yl)-2-(8-thieno[2,3-d]pyrimidin-4-yl-3,8-diazabicyclo[3.2.1]oct-3-yl) acetamide

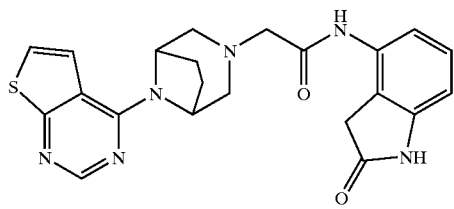

i) 2-Chloro-N-(2-oxo-2,3-dihydro-1H-indol-4-yl)acetamide

The subtitle compound was prepared from 4-aminooxindole (0.19 g) (J. Org. Chem., 1983, 48 (15), 2468–72) and chloroacetyl chloride (0.1 ml) by the method of Example 15 step (i). Yield: 0.25 g MS: ES(–ve) 223 (M–1)

ii) 3-[(2-Oxo-2,3-dihydro-1H-indol-4ylcarbamoyl)-methyl]-3,8-diazabicyclo[3.2.1]octane-8-carboxylic acid, 1,1-dimethylethyl ester The subtitle compound was prepared from the product of step (i) (0.24 g) and 1,1-dimethyl, 3,8-diazabicyclo[3.2.1]octane-8-carboxylate (0.26 g) by the method of Example 19 step (i) Yield: 0.8 g ¹H NMR: δ (DMSO) 10.45(1H, s), 9.26(1H, s), 7.39(1H, d), 7.15(1H, t), 6.62(1H, d), 4.06(2H, brs), 3.45(2H, s), 3.10(2H, s), 2.72(2H, d), 2.38(2H, d), 1.95(2H, d), 1.79(2H, m), 1.41(9H, s).

iii) 2-(3,8-Diazabicyclo[3.2.1]oct-3-yl)-N-(2-oxo-2,3-dihydro-1H-indol-4-yl)acetamide, hydrochloride salt The product of step (ii) (0.8 g) was dissolved in 2M hydrogen chloride in 1,4-dioxane (10 ml), 1,4-dioxane (10 ml), methanol (10 ml) and the reaction mixture was stirred at ambient temperature for 2 hours. The solvents evaporated under reduced pressure to dryness. Yield: 0.8 g MS: ES(+ve) 301 (M+1)

iv) N-(2-Oxo-2,3-dihydro-1H-indol-4-yl)-2-(8-thieno[2,3-d]pyrimidin-4-yl-3,8-diazabicyclo[3.2.1]oct-3-yl)acetamide The title compound was prepared from the product of step (iii) (0.8 g) by the method of Example 1 step (i). Yield: 0.1 g MS: ES(+ve) 435 (M+1)

¹H NMR: δ (DMSO) 10.43(1H, s), 9.27(1H, s), 8.39(1H, s), 7.66(1H, d), 7.62(1H, d), 7.40(1H, d), 7.15(1H, t), 6.62(1H, d), 5.04(2H, brs), 3.47(2H, s), 3.12(2H, s), 2.87 (2H, d), 2.57(2H, d), 2.15(2H, m), 1.97(2H, m).

M.P. 265° C. decomp.

EXAMPLE 36

N-(3-Fluoro-2-methyl-phenyl)-2-((8-quinazolin-4-yl)-3,8-diazabicyclo[3.2.1]oct-3-yl)acetamide

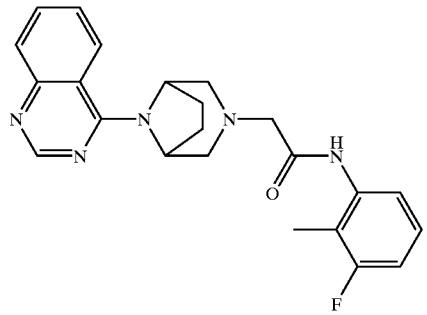

i) 2-Chloro-N-(3-fluoro-2-methyl-phenyl)acetamide

The subtitle compound was prepared from 3-fluoro-2-methylaniline (0.232 g) and chloroacetyl chloride (0.164 ml) by the method of Example 33 step (iii) as a beige solid. Yield: 0.3 g MS: APCI(–ve) 200 (M–1)

ii) N-(3-Fluoro-2-methyl-phenyl)-2-(1,1-dimethylethyloxycarbonyl)-3,8-diazabicyclo[3.2.1]oct-3-yl]acetamide The subtitle compound was prepared from the product of step (i) (179 mg) and 1,1-dimethyl-3,8-diazabicyclo[3.2.1]octane-8-carboxylate (0.2 g) by the method of Example 33 step (iv) as a white solid. Yield: 305 mg MS: APCI (+ve) 378 (M+1)

iii) N-(3-Fluoro-2-methyl-phenyl)-2-(3,8-diazabicyclo[3.2.1]oct-3-yl)acetamide, hydrochloride salt The subtitle compound was prepared from the product of step (ii) (303 mg) by the method of Example 27 step (iv) as a white solid. Yield: 305 mg MS: APCI(+ve) 278 (M+1), APCI (−ve) 276 (M−1)

iv) N-(3-Fluoro-2-methyl-phenyl)-2-((8-quinazolin-4-yl)-3,8-diazabicyclo[3.2.1]oct-3-yl)acetamide The title compound was preapred from the product of step (iii) (223 mg) and 4-chloroquinazoline (133 mg) by the method of Example 2 step (i) as a white solid. Yield: 120 mg MS: APCI(+ve) 406 (M+1)

$^1$H NMR δ (DMSO) 9.34(s, 1H), 8.57(s, 1H), 8.09(d, 1H), 7.84–7.77(m, 2H), 7.60–7.53(m, 2H), 7.22(q, 1H), 6.99(t, 1H), 4.87(bs, 2H), 3.24(s, 2H), 2.97(dd, 2H), 2.77(dd, 2H), 2.17(s, 3H), 2.12–2.04(m, 2H), 1.91–1.85(m, 2H)

EXAMPLE 37

N-(2-Methylphenyl)-2-[8-(benzenesulphonyl)-3,8-diazabicyclo[3.2.1]oct-3-yl]acetamide

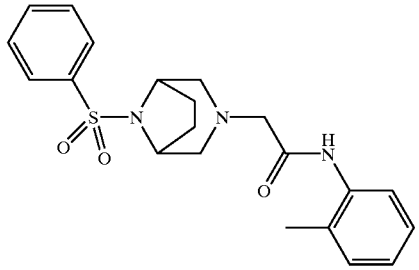

The trifluoroacetate salt of Example 20 step (iv) was converted to the free base by use of aqueous 2N NaOH solution followed by extraction with ethyl acetate. The extracts were dried (MgSO$_4$), filtered and evaporated to dryness, leaving an oil which crystallised on standing.

MS: ES(+ve) 260 (M+1, 100%)

The amine free base (0.075 g) was stirred in acetone (15 ml) and a solution of K$_2$CO$_3$ (0.08 g) in water (0.5 ml) was added, followed by benzenesulphonyl chloride (0.047 g) dissolved in acetone (5.0 ml). The solution was stirred for 1 hour, quenched with water and the white solid was collected by filtration, washed with water and dried in vacuo, to give the title compound. Yield 0.037 g.

MS: APCI(+ve) 487 (M+1, 100%)

$^1$H NMR: δ (CDCl$_3$) 1.55(s, H$_2$O), 1.70(2H, m), 1.85(2H, m), 2.26(3H, s), 2.67(2H, m), 2.85(2H, d of d), 3.18(2H, s), 7.05(2H, m), 7.2(2H, m), 7.52(2H, m), 7.6(1H, m), 7.9(2H, d)

MP: 169–170° C.

EXAMPLE 38

N-(3-Fluoro-2-methylphenyl)-2-[8-(benzenesulphonyl)-3,8-diazabicyclo[3.2.1]oct-3-yl]acetamide

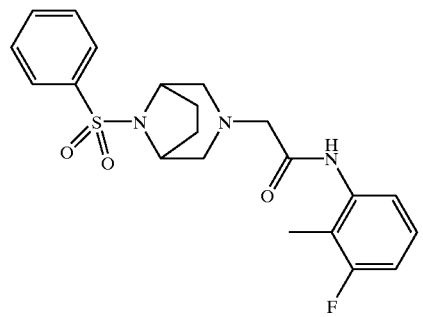

i) Methyl, (3,8-Diazabicyclo[3.2.1]oct-3-yl)acetate, hydrochloride salt

A mixture of the product from Example 30 step (i), 2M HCl in 1,4-dioxane (10 ml) and methanol (10 ml) was stirred at ambient temperature for 2 hours and evaporated to dryness. Yield 0.54 g. Used directly in the next step.

ii) Methyl, (8-benzenesulphonyl-3,8-diazabicyclo[3.2.1]oct-3-yl)acetate

A mixture of the product of step (i) (0.53 g), potassium carbonate (0.66 g) and benzenesulphonyl chloride (0.32 ml) in acetone (10 ml) and 1,4-dioxane (10 ml) was stirred at ambient temperature for 4 hours. The mixture was partitioned between ethyl acetate and water. The organic phase was washed with water, saturated sodium bicarbonate and brine, dried (MgSO$_4$) and evaporated. The product was purified by silica gel chromatography eluting with 0.5% ethanol in dichloromethane. Yield 0.29 g.

$^1$H NMR: δ (DMSO) 7.86(2H, d), 7.69(1H, m), 7.59(2H, m), 4.13(2H, brs), 3.59(3H, s), 3.29(2H, s), 2.67(2H, dd), 2.57(2H, d), 1.59(2H, q), 1.13(2H, m).

iii) (8-Benzenesulphonyl-3,8-diazabicyclo[3.2.1]oct-3-yl) acetic acid

A solution of the product of step (ii) (0.29 g) in ethanol (5 ml) was treated with 1 ml of 1N sodium hydroxide solution. After 1 hour at ambient temperature the reaction mixture was acidified with 2N hydrochloric acid to pH 4 and evaporated to dryness to give a white solid. This was dried at 40° C. in vacuo over phosphorous pentoxide for 2 hours and used directly in the next step.

iv) N-(3-Fluoro-2-methylphenyl)-2-[8-(benzenesulphonyl)-3,8-diazabicyclo[3.2.1]oct-3-yl]acetamide A mixture of the product of step (iii) (0.45 mmol), 2-fluoro-2-methylaniline (60 μl), PyBroP (0.25 g), N,N-dimethylaminopyridine (54 mg) and N,N-diisopropylethylamine (0.23 ml) in N,N-dimethylformamide (5 ml) was stirred at ambient temperature for 16 hours. The reaction mixture was partitioned between ethyl acetate and water. The organic phase was washed with water and brine, dried (MgSO$_4$) and evaporated. The residue was purified by flash chromatography eluting with 1% ethanol in dichloromethane followed by further chromatography with 20% ethyl acetate/iso-hexane to give the title compound as a white solid. Yield: 30 mg.

MS: AP (+ve) 418 (M+1)

$^1$H NMR: δ (DMSO) 9.20(1H, s), 7.88(2H, d), 7.70(1H, m), 7.60(2H, m), 7.49(1H, d), 7.20(1H, q), 6.97(1H, t), 4.17(2H, brs), 3.17(2H, s), 2.81(2H, dd), 2.50(2H, d), 2.09 (3H, s), 1.78(2H, m), 1.20(2H, m).

M.P. 168–9° C.

EXAMPLE 39

Cis-N-(3-Fluoro-2-methyl-phenyl)-2-(4-benzenesulphonyl)-3,5-dimethyl)piperazin-1-yl)acetamide

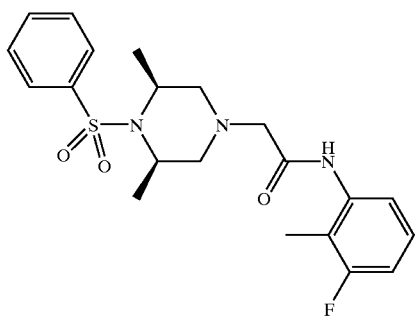

i) Cis-N-(3-Fluoro-2-methyl))phenyl)-2-(4-benzenesulphonyl)-3,5-dimethyl)piperazin-1-yl)acetamide The title compound was prepared from the product of Example 33 step (ii) (152 mg) and the product of Example 36 step (i) (132 mg) by the method of Example 33 step (iv) as a white solid. Purification was by silica gel chromatography eluting with iso-hexane/acetone (7:3). Yield: 58 mg.

MS: APCI(+ve) 420 (M+1)

$^1$H NMR δ (DMSO) 9.23(s, 1H), 7.83(d, 2H), 7.69–7.58 (m, 3H), 7.34(d, 1H), 7.20(q, 1H), 6.99(t, 1H), 4.06–3.99(m, 2H), 3.03(s, 2H), 2.64(d, 2H), 2.08(s, 3H), 1.90(dd, 2H), 1.42(d, 6H)

EXAMPLE 40

N-(2-Methylphenyl)-2-[8-(3-cyanobenzenesulphonyl)-3,8-diazabicyclo[3.2.1]oct-3-yl]acetamide

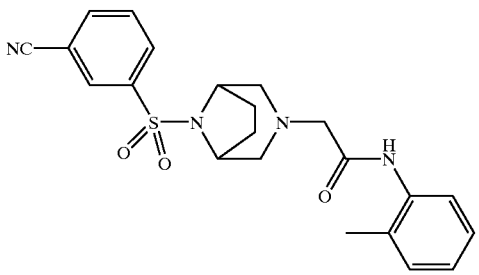

The title compound was prepared from the product of Example 20 step (iv) and 3-cyanobenzenesulphonyl chloride by the method of Example 37 as a white solid. Yield 0.101 g.

MS: APCI(+ve) 425 (M+1, 100%)

$^1$H NMR: δ (CDCl$_3$) 1.76(2H, m), 1.92(2H, m), 2.27(3H, s), 2.64(2H, d), 2.85(2H, m), 3.20(2H, s), 4.26(2H, s), 7.06(1H, m), 7.20(2H, m), 7.68(1H, m), 7.87(1H, m), 8.02 (1H, d), 8.13(1H, m), 8.18(1H, s), 8.68(1H, s) MP: 166–8° C.

EXAMPLE 41

2-[8-(3-Methoxybenzenesulphonyl)-3,8-diazabicyclo[3.2.1]oct-3-yl]-N-(2-methylphenyl)acetamide

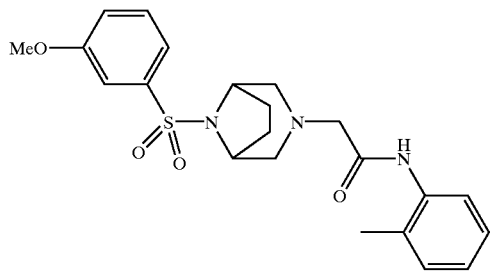

The title compound was prepared from the product of Example 20 step (iv) and 3-methoxybenzenesulphonyl chloride by the method of Example 37 as a white solid Yield 0.095 g.

MS: APCI(+ve) 430 (M+1, 100%)

$^1$H NMR: δ (CDCl$_3$) 1.75(2H, m), 1.82(2H, m), 2.26(3H, s), 2.65(2H, d), 2.82(2H, d of d), 3.18(2H, s), 3.86(3H, s), 4.25(2H, br s), 7.02–7.25(4H, m), 7.40–7.50(3H, m), 8.02 (1H, d), 8.75(1H, br s)

MP: 163–5° C.

EXAMPLE 42

2-[8-(Benzo[1,2,5]oxadiazole-4-sulphonyl)-3,8-diazabicyclo[3.2.1]oct-3-yl]-N-(2-methylphenyl)acetamide

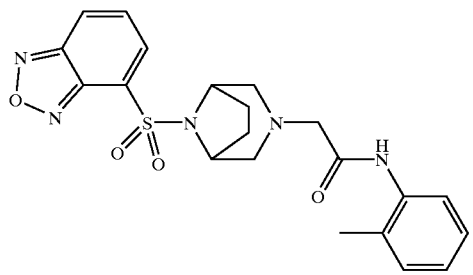

The title compound was prepared from the product of Example 20 step (iv) by the method of Example 37 as a white solid. Yield: 0.088 g.

MS: APCI(+ve) 442 (M+1, 100%)

$^1$H NMR: δ (CDCl$_3$) 1.90–2.02(4H, m), 2.28(3H, s), 2.65(2H, m), 2.90(2H, m), 3.16(2H, s), 4.55(2H, s), 7.06 (1H, m), 7.19(2H, m), 7.54(1H, m), 8.08(3H, d), 8.75(1H, br s)

MP: 167–8° C.

EXAMPLE 43

2-[8-(Benzo[1,2,5]thiadiazole-4-sulphonyl)-3,8-diazabicyclo[3.2.1]oct-3-yl]-N-(2-methylphenyl)acetamide

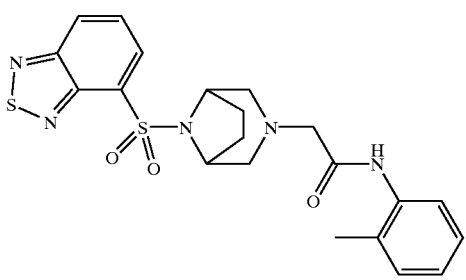

The title compound was prepared from the product of Example 20 step (iv) by the method of Example 37 as a white solid. Yield 0.108 g.

MS: APCI(+ve) 458 (M+1, 100%)

$^1$H NMR: δ (CDCl$_3$) 1.75(2H, m), 1.93(2H, m), 2.27(3H, s), 2.62(2H, m), 2.85(2H, d of d), 3.14(2H, s), 4.61(2H, br s), 7.05(1H, m), 7.20(2H, m), 7.70(1H, m), 8.02(1H, d), 8.26(2H, d of d), 8.77(1H, br s)

MP: 169–70° C.

EXAMPLE 44

2-[8-(5-Chlorothieno-2-yl)sulphonyl)-3,8-diazabicyclo[3.2.1]oct-3-yl]-N-(2-methylphenyl)acetamide

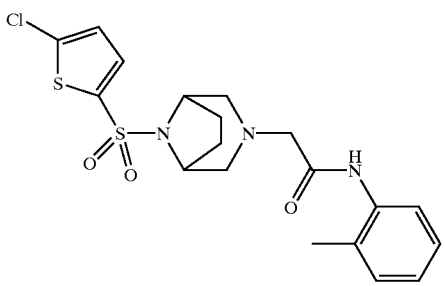

The title compound was prepared from the product of Example 20 step (iv) and 2-chloro-5-chlorosulphonyl-thiophene by the method of Example 37 as a white solid. Yield 0.108 g.

MS: APCI(+ve) 440 (M+1, 100%)

$^1$H NMR: δ (CDCl$_3$) 1.90(4H, m), 2.28(3H, s), 2.70(2H, d), 2.86(2H, m), 3.21(2H, s), 4.27(2H, br s), 6.94(1H, d), 7.05(1H, m), 7.20(2H, m), 7.42(1H, d), 8.04(1H, d), 8.73(1H, br s)

MP: 150–2° C.

EXAMPLE 45

2-[8-(2-Chlorobenzenesulphonyl)-3,8-diazabicyclo[3.2.1]oct-3-yl]-N-(2-methylphenyl)acetamide

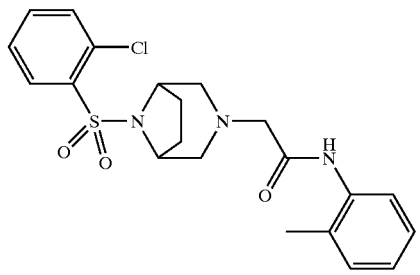

The title compound was prepared from the product of Example 20 step (iv) and 2-chlorobenzenesulphonyl chloride by the method of Example 37 as a white solid. Yield 0.085 g.

MS: APCI(+ve) 434 (M+1, 100%)

$^1$H NMR: δ (CDCl$_3$) 2.07(4H, m), 2.31(3H, s), 2.66(2H, d), 2.82(2H, m), 3.18(2H, s), 4.31(2H, br s), 7.05(1H, m), 7.22(2H, m), 7.40(1H, m), 7.53(2H, m), 8.05(1H, d), 8.12(1H, d of d), 8.80(1H, br s)

MP: 170–1° C.

EXAMPLE 46

2-[8-(5-Chloro-2-methoxybenzenesulphonyl)-3,8-diazabicyclo[3.2.1]oct-3-yl]-N-(2-methylphenyl)acetamide

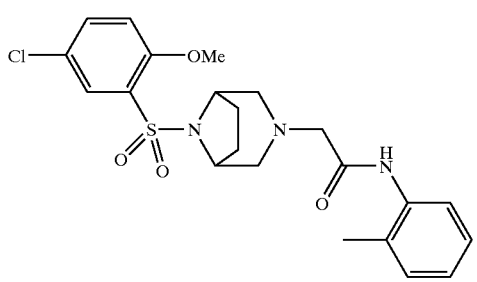

The title compound was prepared from the product of Example 20 step (iv) and 3-chloro-6-methoxybenzenesulphonyl chloride by the method of Example 37 as a white solid Yield 0.105 g.

MS: APCI(+ve) 464 (M+1, 100%)

$^1$H NMR: δ (CDCl$_3$) 1.93(4H, m), 2.30(3H, s), 2.62(2H, m), 2.85(2H, m), 3.17(2H, s), 3.95(3H, s), 4.35(2H, br s), 6.95(1H, d), 7.05(1H, m), 7.20(2H, m), 7.46(1H, d of d), 7.91(1H, d), 8.05(1H, d), 8.80(1H, br s)

MP: 180–1° C.

EXAMPLE 47

2-[8-(4-Acetylaminomethoxybenzenesulphonyl)-3,8-diazabicyclo[3.2.1]oct-3-yl]-N-(2-methylphenyl)acetamide

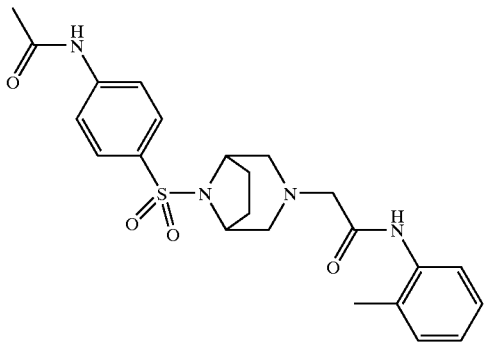

The title compound was prepared from the product of Example 20 step (iv) and 4-acetylamidobenzenesulphonyl chloride by the method of Example 37 as a white solid. Yield 0.108 g.

MS: APCI(+ve) 457 (M+1, 100%)
$^1$H NMR: δ (CDCl$_3$) 1.60(2H, m), 1.82(2H, m), 2.18(3H, s), 2.26(3H, s), 2.65(2H, d), 2.80(2H, d of d), 3.18(2H, s), 4.20(2H, br s), 7.05(1H, m), 7.18(2H, m), 7.78(4H, s), 8.00(1H, d), 8.77(1H, br s), 9.64(1H, s)
MP: 205–6° C.

EXAMPLE 48

N-(2-Methylphenyl)-2-[(8-(3-methylthieno[2,3-d]pyrimidin-4-yl)-3,8-diazabicyclo[3.2.1]oct-3-yl]acetamide

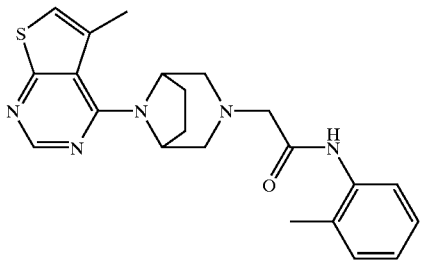

The trifluoroacetate salt of Example 20 step (iv) was converted to the free base by use of aqueous 2N NaOH solution followed by extraction with ethyl acetate. The extracts were dried (MgSO$_4$), filtered and evaporated to dryness, leaving an oil which crystallised on standing.

MS: ES(+ve) 260 (M+1, 100%)

A mixture of the amine free base (0.13 g), N,N-diisopropylethylamine (0.5 ml), 4-dimethylaminopyrimidine (0.06 g) and 4-chloro-3-methylthieno[2,3-d]pyrimidine was heated in N-methylpyrrolidin-2-one (5.0 ml) at 100° C. for 5 hours. The solvent was evaporated under high vacuum and the residue was slurried with water, filtered and dried. Purification was by chromatography on silica gel eluting with dichloromethane containing ethanol (1%) to give the title compound as a white solid. Yield (0.053 g).

MS: APCI(+ve) 408 (M+1, 100%)
$^1$H NMR: δ (CDCl$_3$) 1.98(4H, m), 2.35(3H, s), 2.62(3H, s), 2.95(4H, m), 3.26(2H, s), 4.46(2H, br s), 7.00(1H, s), 7.10(1H, m), 7.20(2H, m), 8.10(1H, d), 8.53(1H, s), 8.96 (1H, br s)
MP: 199–200° C.

EXAMPLE 49 cis-2-(3,5-Dimethyl-4-(thieno[2,3-d]pyrimidin-4-yl)piperazin-1-yl)-N-(1-methyl-1H-benzoimidazol-2-yl)acetamide

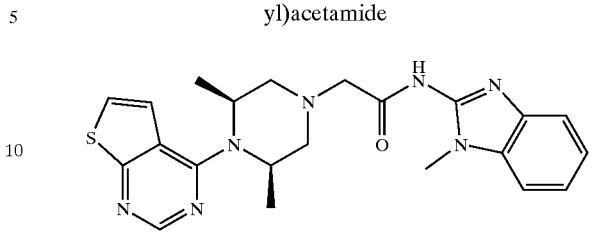

The title compound was prepared from the product of Example 9 step (ii) (0.2 g) and 2-amino-1-methyl-benzimidazole (0.14 g) by the method of Example 38 step (iv). Purification was by silica gel chromatography followed by recrystallisation from methanol. Yield 45 mg.

MS: APCI (+ve) 436 (M+1)
$^1$H NMR: δ (CDCl$_3$) 8.47(1H, s), 7.41(1H, d), 7.26(3H, m), 5.01(2H, brs), 3.68(3H, s), 3.40(2H, s), 3.05(2H, d), 2.50(2H, d), 1.61(6H, s).
M.P. 200° C.

EXAMPLE 50

Cis-2-(3,5-Dimethyl-4-(thieno[2,3-d]pyrimidin-4-yl)piperazin-1-yl)-N-(2-methyl-5-(4-piperidinyloxy)phenyl)acetamide, hydrochloride salt

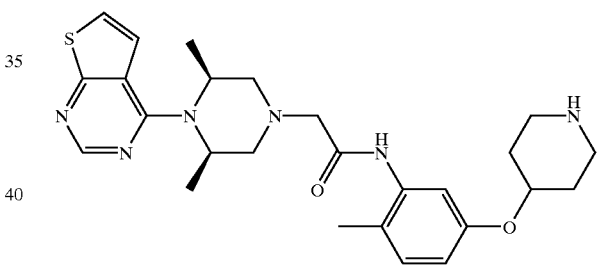

i) 1,1-Dimethylethyl, 4-(4-methyl-3-nitro)phenoxypiperidine-1-carboxylate

A solution of 4-methyl-3-nitrophenol (2 g), 1,1-dimethylethyl, 4-hydroxypiperidine-1-carboxylate (2.6 g), triphenylphosphine (4.11 g) in tetrahydrofuran (40 ml) under nitrogen at 0° C. was treated with diethylazidodicarboxylate (2.3 ml) over 1 minute. The cooling bath was removed and the mixture allowed to stir at ambient temperature for 48 h. The solvent was evaporated under reduced pressure. The residue was purified by silica gel chromatography eluting with dichloromethane containing 1% triethylamine to give the subtitle product as a pale yellow oil. Yield: 3.46 g $^1$H NMR δ (CDCl$_3$) 7.52(dd, 1H), 7.21(dd, 1H), 7.08(dd, 1H), 4.50(m, 1H), 3.70(m, 2H), 3.55(m, 2H), 2.50(s, 3H), 2.0–1.6(m, 4H), 1.5(s, 9H)

ii) 1,1-Dimethylethyl, 4-(3-amino-4-methyl)phenoxypiperidine-1-carboxylate

A solution of the product from step (i) (2 g), 10% Palladium on charcoal (300 mg) were stirred under a 1 bar atmosphere of hydrogen at ambient temperature. The mixture was filtered through celite and solvent removed under reduced pressure to leave the subtitle product as a beige solid. Yield: 1.88 g ¹H NMR δ (CDCl₃) 6.9(d, 1H), 6.3(m, 2H), 4.4(m, 1H), 3.7(m, 2H), 3.6(bs, 2H), 3.3(m, 2H), 2.10(s, 3H), 1.9–1.6(m, 4H), 1.50(s, 9H)

iii) 2-Chloro-N-5-(1-(1,1-dimethylethoxycarbonyl)₄-piperidinyloxy)-4-methyl-5-nitro)acetamide A solution of the product from step (ii) (1.4 g), N,N-diisopropylethylamine (2 ml) in dichloromethane(30 ml) under nitrogen at 0° C. was treated with chloroacetylchloride (0.4 ml). After 4 h the reaction mixture was partitioned between water and dichloromethane. The organic phase collected, dried (MgSO₄) and solvent reduced under reduced pressure to leave the subtitle compound as a brown oil. Yield: 1.8 g This was used directly in the next step.

iv) Cis-2-(3,5-Dimethyl-4-(thieno[2,3-d]pyrimidin-4-yl)piperazin-1-yl)-N-(2-methyl-5-(1-(1,1-dimethylethoxycarbonyl)-4-piperidinyloxy)phenyl)acetamide The subtitle compound was prepared from the product of Example 2 step (ii) (0.4 g) and the product of step (iii) (0.56 g) by the method of Example 33 step (iv) as a pale yellow gum. Yield: 0.25 g MS: APCI(+ve) 595 (M+1), APCI(−ve) 593 (M−1)

v) Cis-2-(3,5-Dimethyl-4-(thieno[2,3-d]pyrimidin-4-yl)piperazin-1-yl)-N-(2-methyl-5-(4-piperidinyloxy)phenyl)acetamide, hydrochloride salt The title compound was prepared from the product of step (iv) (0.24 g) by the method of Example 27 step (iv) as a white solid. Purification was by reverse phase HPLC eluting with aq. 1% ammonium acetate/acetonitrile (95% to 60%). Yield. 80 mg MS: APCI(+ve) 495 (M+1), APCI(−ve) 493 (M−1)

¹HNMR δ (DMSO) 8.97(bs, 1H), 8.52(s, 1H), 7.7(d, 1H), 7.62(d, 1H), 7.26(s, 1H), 7.18(d, 1H), 6.84(d, 1H), 5.30(bs, 2H), 4.60(bs, 1H), 3.30–3.00(2×bs, 4H), 2.20(s, 3H), 2.15–1.80(m, 4H), 1.60(d, 6H)

EXAMPLE 51

Cis-2-(3,5-Dimethyl-4-benzenesulphonyl)piperazin-1-yl)-N-(2-methyl-5-(4-piperidinyloxy)phenyl)acetamide

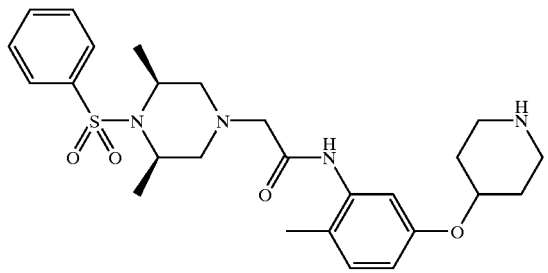

i) Cis-2-(3,5-Dimethyl-4-benzenesulphonyl)piperazin-1-yl)-N-(2-methyl-5-(1-(1,1-dimethylethoxycarbonyl)4-piperidinyloxy)phenyl)acetamide The subtitle compound was prepared from the product of Example 33 step (ii) (0.42 g) and the product of Example 50 step (iii) (0.55 g) by the method of Example 33 step (iv). Purification was by silica gel chromatography eluting with dichloromethane/ethyl acetate (95:5) to give the subtitle compound as colourles gum. Yield: 0.23 g MS: APCI(+ve) 601 (M+1), APCI(−ve) 599 (M−1)

ii) Cis-2-(3,5-Dimethyl-4-benzenesulphonyl)piperazin-1-yl)-N-(2-methyl-5-(4-piperidinyloxy)phenyl)acetamide The title compound was prepared from the product of step (i) (0.2 g) by the method of Example 27 step (iv) as a white solid after purification by reverse phase HPLC eluting with 1% aq. ammonium acetate/acetonitrile (95% to 60%). Yield: 50 mg MS: APCI(+ve) 501 (M+1), APCI(−ve) 499 (M−1)

¹HNMR δ (DMSO) 8.8(bs, 1H), 7.8(d, 2H), 7.7(m, 3H), 7.25(s, 1H), 7.15(d, 1H), 6.75(d, 1H), 4.60(m, 1H), 4.2–4.0 (bs, 2H), 3.3–3.0(2×m, 4H), 2.2(s, 3H), 2.15–1.70(m, 4H), 1.5(d, 6H)

EXAMPLE 52

Cis-2-(3,5-Dimethyl-4-(quinazolin-4-yl)piperazin-1-yl)-N-(2-methyl-5-(4-piperidinyloxy)phenyl)acetamide

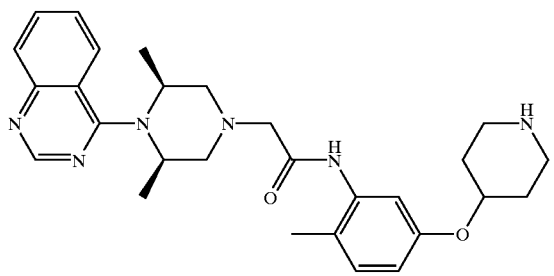

i) 1,1-Dimethylethyl, 4-(4-quinazolinyl)-3,5-dimethylpiperazine-1-carboxylate 4-Chloroquinazoline (6 g), cis-1,1-diethylethyl, 3,5-dimethylpiperazine-1-carboxylate (7.8 g), N,N-diisopropylethylamine (32 ml) in 1-methyl-2-pyrrolidinone (70 ml) were heated at 120° C. for 6 days under nitrogen. The mixture was partitioned between ethyl acetate and brine. The organic phase collected and further washed with brine (×2), collected, dried (MgSO₄) and solvent evaporated under reduced pressure to leave a pale brown solid. Purification was by silica gel chromatograpy eluting with ethyl acetate/iso-hexane (3:7) to give the subtitle compound as a pale yellow oil. Yield: 1.1 g MS: APCI(+ve) 343 (M+1)

ii) cis-4-(4-Quinazolinyl)-2,6-dimethylpiperazine, hydrochloride salt

The subtitle compound was prepared from the product of step (i) (1 g) by the method of Example 27 step (iv) as cream solid. Yield: 1.8 g MS: APCI(+ve) 243 (M+1)

iii) Cis-2-(3,5-Dimethyl-4-(4-quinazolinyl)piperazin-1-yl)-N-(2-methyl-5-(1-(1,1-dimethylethoxycarbonyl)4-piperidinyloxy)phenyl)acetamide The subtitle compound was prepared from the product of step (ii) (0.56 g) and the product of Example 50 step (iii) (0.37 g) by the method of Example 33 step (iv). Purification was by silica gel chromatography eluting with ethyl acetate/iso-hexane (9:1) to give the subtitle compound as a white solid. Yield. 0.18 g MS: APCI(+ve) 589 (M+1)

iv) Cis-2-(3,5-Dimethyl-4-(quinazolin-4-yl)piperazin-1-yl)-N-(2-methyl-5-(4-piperadinyloxy)phenyl)acetamide The title compound was prepared from the product of step (iii) (0.18 g) by the method of Example 27 step (iv). Purification was by reverse phase HPLC eluting qith 1% aq. ammonium acetate/acetonitrile (99% to 50%) to give the title compound as a white solid. Yield: 0.079 g MS: APCI(+ve) 489 (M+1)

¹H NMR δ (CDCl₃) 9.26 (bs, 1H), 9.08(bs, 1H), 8.35(d, 1H), 8.00(d, 1H), 7.95(s, 1H), 7.90(t, 1H), 7.60(t, 1H), 7.10(d, 1H), 6.61(d, 1H), 4.57(m, 1H), 3.25(m+s, 4H), 3.05(m, 2H), 2.90(d, 2H), 2.60(m, 2H), 2.30(s, 3H), 2.10(m, 2H), 2.0(m, 2H), 1.0(d, 6H)

EXAMPLE 53

Cis-2-(3,5-Dimethyl-4-(4-quinazolinyl)piperazin-1-yl)-N-(2-methyl-5-(piperazin-4-yl-methyl)phenyl) acetamide

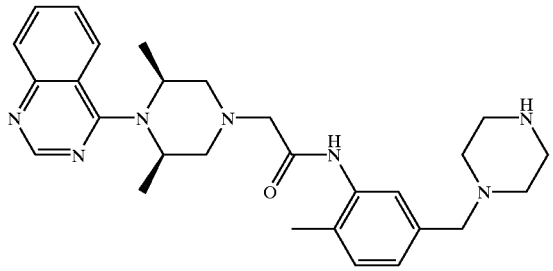

i) 2-Chloro-N-5-((1-(1,1-dimethylethyloxycarbonyl) piperazin-4-yl)methyl)phenyl-2-methyl)acetamide The subtitle compound was prepared from the product of Example 27 step (ii) (0.1 g) by the method of Example 33 step (iii) as a beige foam. Yield: 0.15 g MS: APCI(+ve) 382 (M+1)

ii) Cis-2-(3,5-Dimethyl-4-(4-quinazolinyl)piperazin-1-yl)-N-(2-methyl-5-(1-(1,1-dimethylethyloxycarbonyl) piperazin-4-yl-methyl)phenyl)acetamide The subtitle compound was prepared from the product of Example 52 step (ii) (0.2 g) and the product of step (i) (0.21 g) by the method of Example 33 step (iv). Purification was by silica gel chromatography eluting with ethyl acetate/isohexane (9:1) to give the subtitle compound as a white solid. Yield. 0.068 g MS: APCI(+ve) 588 (M+1)

iii) Cis-2-(3,5-Dimethyl-4-(4-quinazolinyl)piperazin-1-yl)-N-(2-methyl-5-(piperazin-4-yl-methyl)phenyl)acetamide The title compound was prepared from the product of step (ii) (0.069 g) by the method of Example 27 step (iv). Purification was by reverse phase HPLC eluting with 1% aq. ammonium acetate/acetonitrile (99% to 50%) to give the title compound as a white solid. Yield: 0.072 g MS: APCI(+ve) 488 (M+1)

$^1$H NMR δ (CDCl$_3$) 8.58(bs, 1H), 8.25(bs, 1H), 7.63(d, 1H), 7.20(m, 2H), 6.95(t, 1H), 6.50(d, 1H), 6.35(d, 1H), 3.60(bs, 2H), 2.80(s, 1H), 2.60(s, 1H), 2.30(bs, 3H), 2.20(d, 1H), 2.0(m, 1H), 1.90(bs, 2H), 1.70(s, 2H), 1.30(bd, 6H)

EXAMPLE 54

Cis-2-(3,5-Dimethyl-4-(4-quinazolinyl)piperazin-1-yl)-N-(2-methyl-5-(2-(N-methylamino)ethoxy) phenyl)acetamide

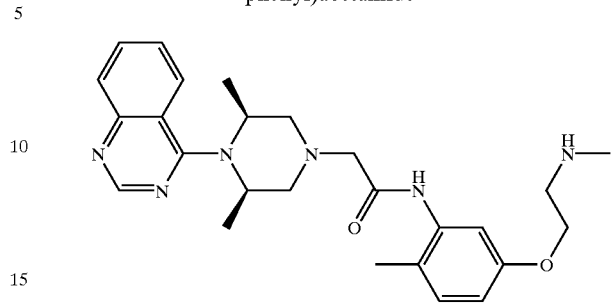

i) Cis-2-(3,5-Dimethyl-4-(4-quinazolinyl)piperazin-1-yl)-N-(2-methyl-5-(2-(1,1-dimethylethyloxycarbonyl-N-methylaminoethoxy)phenyl)acetamide The subtitle compound was prepared from the product of Example 52 step (ii) (0.64 g) and the product from Example 33 step (iii) (0.59 g) by the method of Example 33 step (iv). Yield. 0.45 g MS: APCI(+ve) 563 (M+1), APCI(–ve) 561 (M–1)

ii) Cis-2-(3,5-Dimethyl-4-(4-quinazolinyl)piperazin-1-yl)-N-(2-methyl-5-(2-(N-methylamino)ethoxy)phenyl) acetamide The title compound was prepared from the product of step (i) (0.4 g) by the method of Example 27 step (iv). Purification was by reverse phase HPLC eluting with 1% aq. ammonium acetate/acetonitrile (99% to 50%) to give the title compound as a white solid. Yield: 0.25 g MS: APCI(+ve) 463 (M+1)

$^1$H NMR δ (CDCl$_3$) 9.30(bs, 1H), 9.12(bs, 1H), 8.39(, 1H), 8.05(d, 1H), 7.95(m, 2H), 7.60(t, 1H), 7.10(d, 1H), 6.70(d, 1H), 4.20(m, 2H), 4.0(bs, 2H), 3.30(s, 2H), 3.20(m, 2H), 2.90(m, 2H), 2.60(m+s, 5H), 2.35(s, 3H), 1.0(bs, 6H)

EXAMPLE 55 cis-2-[4-(3-Cyanobenzenesulphonyl)-3,5-dimethylpiperazin-1-yl]-N-(2-methylphenyl) acetamide

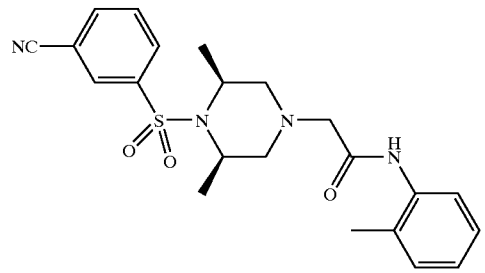

i) cis-2-(3,5-Dimethylpiperazin-1-yl-N-(2-methylphenyl) acetamide

A mixture of 2-chloro-N-(2-methylphenyl)acetamide (1.83 g), N,N-disopropylethylamine (5.0 ml), sodium iodide (0.020 g) and cis-2,6-dimethylpiperazine 1.14 g) in ethanol (50 ml) was heated at reflux for 2.5 hours. The solvent was removed and the residue was crystallised from ethanol as white needles. It was dissolved in water and the solution was made basic with 2N aqueous NaOH, extracted with dichloromethane and the extracts were dried (MgSO$_4$), filtered and evaporated to dryness, leaving an oil which crystallised on standing. Yield 1.1 g.

¹H NMR: δ (CDCl₃) 1.08(6H, d), 1.40(1H br s) 1.94(2H, t), 2.27(3H, s), 2.83(2H, m), 2.98(2H, m) 3.14(2H, s), 7.03(1H, m), 7.20(2H, m), 8.18(1H, d), 9.32(1H, br s)

MP: 105–6° C.

ii) cis-2-[4-(3-Cyanobenzenesulphonyl)-3,5-dimethylpiperazin-1-yl]-N-(2-methylphenyl)acetamide The product of step (i) (0.60 g), 4-dimethylaminopyridine (0.14 g) in pyridine (2.0 ml) was stirred while 3-cyanobenzenesulphonyl chloride (0.46 g) was added. The mixture was stirred for 10 minutes after which it solidified. After 1 hour the solid was triturated with water and filtered off. It was purified by chromatography on silica eluting with ethyl acetate/iso-hexane (1:1) to give the title compound as a pale yellow solid. Yield: 0.22 g.

MS: APCI(+ve) 427 (M+1, 100%)

¹H NMR: δ (CDCl₃) 1.55(6H, d), 2.17(2H, d of d), 2.32(3H, s), 2.73(2H, d), 3.10(2H, s), 4.13(2H, m), 7.10(1H, m), 7.20(2H, m), 7.67(1H, m), 7.85(1H, m), 7.95(1H, m), 8.05(1H, m), 8.12(1H, m), 8.67(1H, br s).

MP: 152–3° C.

EXAMPLE 56 cis-N-(2-Methylphenyl)-2-[4-(3-nitrobenzenesulphonyl)-3,5-dimethylpiperazin-1-yl]-acetamide

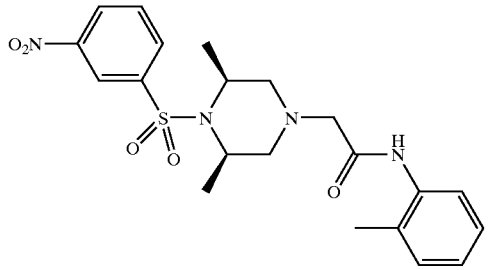

The title compound was prepared from the product of Example 55 step (i) and 3-nitrobenzenesulphonyl chloride by the method of Example 55 step (ii) as an off white solid.

Yield: 3.06 g

MS: APCI(+ve) 447 (M+1, 100%)

¹H NMR: δ (CDCl₃) 1.59(6H, d), 2.20(2H, d of d), 2.30(3H, s), 2.74(2H, d), 3.10(2H, s), 4.16(2H, m), 7.05(1H, m), 7.20(2H, m), 7.75(1H, t), 7.96(1H, d), 8.16(1H, d of d), 8.43(1H, d of d), 8.67(2H, br s).

MP: 163–4° C.

EXAMPLE 57 cis-2-[4-(3-Aminobenzenesulphonyl)-3,5-dimethylpiperazin-1-yl]-N-(2-methylphenyl)acetamide

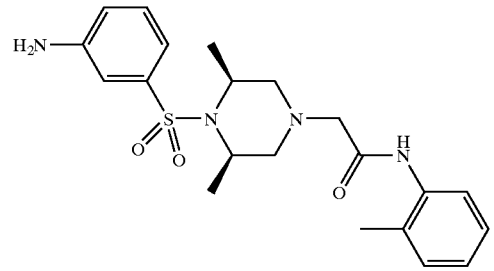

To a stirred solution of the product of Example 56 (3.0 g) in ethanol (1500 ml) was added 5% palladium on charcoal (1.5 g) followed by dropwise addition of hydrazine hydrate (20 ml). The mixture was stirred for 1 hour, filtered through 'hyflo' and the filtrate was evaporated to dryness. The solid residue was crystallised from ethanol to give the title compound as a white solid. Yield 1.6 g.

MS: APCI(+ve) 417 (M+1, 100%)

¹H NMR: δ (CDCl₃) 1.54(6H, d), 2.18(2H, d of d), 2.30(3H, s), 2.65(2H, d), 3.07(2H, s), 3.90(2H, s), 4.15(2H, m), 6.82(1H, d of d), 7.05–7.20(6H, m), 7.99(1H, d), 8.75 (1H, s).

MP: 202–3° C.

EXAMPLE 58

Cis-2-(3,5-Dimethyl-4-(3-cyanobenzenesulphonyl)piperazin-1-yl)-N-(quinolin-5-yl)acetamide

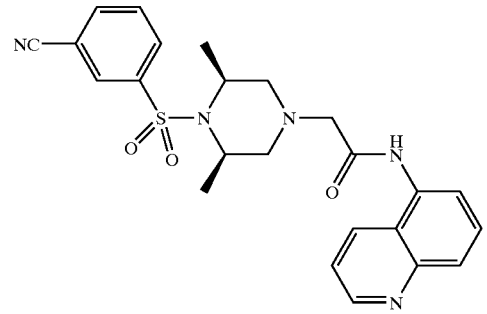

i) Cis-2-(3,5-Dimethyl-piperazin-1-yl)-N-(quinolin-5-yl)acetamide

A mixture of 2-chloro-N-(quinolin-5-yl)acetamide (7.76 g) (J. Indian Chem Soc, 1940, 17, 619–621), cis-2,6-dimethylpiperazine (4.42 g), sodium bicarbonate (8.9 g) in ethanol (100 ml) was heated at reflux for 4 h. The solvent was removed under reduced pressure. The residue was partitioned between chloroform and brine. The organic phase collected and the aqeuous phase further extracted (×6) with chloroform. The combined extracts dried (MgSO₄) and solvent removed under reduced pressure. Yield: 6.8 g MS: APCI(+ve) 299 (M+1)

ii) Cis-2-(3,5-Dimethyl-4-(3-cyanobenzenesulphonyl)piperazin-1-yl)-N-(quinolin-5-yl)acetamide The product from step (i) (150 mg), 4-N,N-dimethylaminopyridine (31 mg) in pyridine (0.5 ml) was treated in one portion with 3-cyanobenzensuphonyl chloride (1 eq) and then immediately heated for 30 minutes. The mixture was partitioned between dichloromethane and water. The organic phase collected, dried (MgSO$_4$) and solvent removed under reduced pressure. The reisdue was purified by reverse phase HPLC eluting with 0.1% aq. ammonium acetate/acetontrile (95% to 50%) as eluant to give the title compound as a white solid. Yield: 8 mg MS: APCI(+ve) 464 (M+1)

$^1$HNMR δ (CD$_3$OD) 9.87(d, 1H), 8.4(d, 1H), 8.3(d, 1H), 8.2(m, 2H), 8.0(m 2H), 7.78(m, 2H), 7.6(m, 1H), 4.2(m, 2H), 3.24(s, 2H), 2.82(d, 2H), 2.1(dd, 2H), 1.57(d, 6H)

EXAMPLE 59

Cis-2-(3,5-Dimethyl-4-(4-cyanobenzenesulphonyl)piperazin-1-yl)-N-(quinolin-5-yl)acetamide

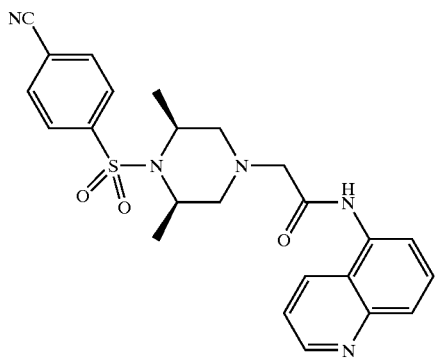

The title compound was prepared from the product of Example 58 step (i) (0.503 mmol) and 4-cyanobenzenesulphonyl chloride (0.503 mmol) by the method of Example 58 step (ii) as a white solid. Yield: 4 mg MS: APCI(+ve) 464 (M+1)

$^1$HNMR δ (CD$_3$OD) 8.9(d, 1H), 8.4(d, 1H), 8.1(d, 2H), 7.93–7.96(m, 2H), 7.8(m, 2H), 7.6(m, 1H), 4.2(m, 2H), 3.24(s, 2H), 2.81(d, 2H), 2.1(dd, 2H), 1.57(d, 6H)

EXAMPLE 60

Cis-2-(4-(3-cyanobenzenesulphonyl)-3,5-dimethylpiperazin-1-yl)-N-(3-fluoro-2-methylphenyl)acetamide

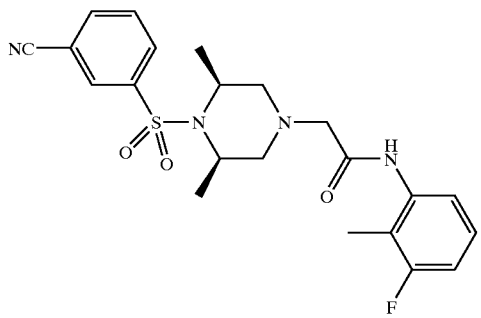

i) cis-(3,5-Dimethylpiperazin-1-yl)-N-(2-methyl-3-fluorophenyl)acetamide

The subtitle compound was prepared from the product of Example 36 step (i) (14.5 g) and cis-2,6-dimethylpiperazine (9.0 g) by the method of Example 58 step (i) as cream solid. Yield: 11.48 g MS: APCI(+ve) 280 (M+1)

ii) Cis-2-(4-(3-Cyanobenzenesulphonyl)-3,5-dimethylpiperazin-1-yl)-N-(3-fluoro-2-methylphenyl)acetamide The title compound was prepared from the product of step (i) (0.503 mmol) and 3-cyanobenzenesulphonyl chloride (0.503 mmol) by the method of Example 58 step (ii) as a white solid. Yield: 44 mg MS: APCI(+ve) 445 (M+1)

$^1$H NMR δ (CD$_3$OD) 8.24(d, 1H), 8.14(d, 1H), 7.98(d, 1H), 7.76(t, 1H), 7.36(d, 1H), 7.1(q, 1H), 6.93(t, 1H), 4.14–4.16(m, 2H), 3.10(s, 2H), 2.73(d, 2H), 2.16(d, 3H), 2.04(dd, 2H), 1.53(d, 6H)

EXAMPLE 61

Cis-2-(-(4-Cyanobenzenesulphonyl)-3,5-dimethylpiperazin-1-yl)-N-(3-fluoro-2-methylphenyl)acetamide

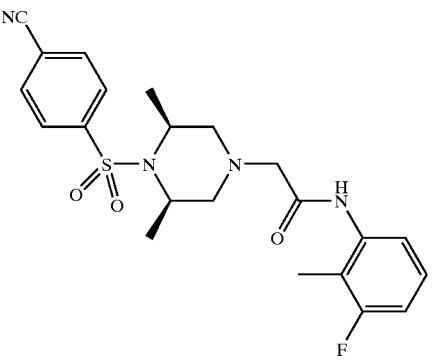

The title compound was prepared from the product of Example 60 step (i) (0.503 mmol) and 4-cyanobenzenesulphonyl chloride (0.503 mmol) by the method of Example 58 step (ii) as a white solid. Yield: 4 mg MS: APCI(+ve) 445 (M+1)

$^1$H NNMR δ (CD$_3$OD) 8.24(d, 1H), 8.14(d, 1H), 7.98(d, 1H), 7.76(t, 1H), 7.36(d, 1H), 7.1(q, 1H), 6.93(t, 1H), 4.14–4.16(m, 2H), 3.10(s, 2H), 2.73(d, 2H), 2.16(d, 3H), 2.04(dd, 2H), 1.53(d, 6H)

EXAMPLE 62 cis-2-[4-(3-Acetylaminobenzenesulphonyl)-3,5-dimethylpiperazin-1-yl]-N-(2-methylphenyl)acetamide

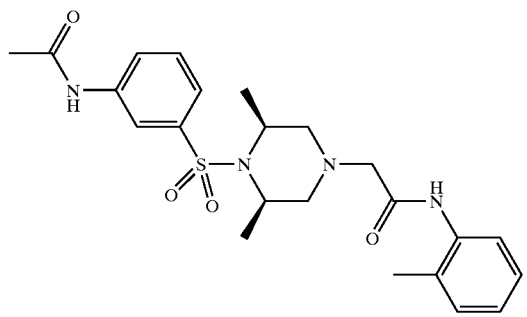

A solution of the product from Example 57 (0.2 g) and N,N-diisopropylethylamine (0.3 ml) in dichloromethane (10 ml) was rapidly stirred whilst a solution of acetyl chloride (0.055 g) in dichloromethane (2.0 ml) was added. After 3 hours a further amount of acetyl chloride (0.022 g) was added, the mixture was stirred 3 hours more then evaporated to dryness. The residue was triturated with water, filtered and dried in vacuo, to give the title compound as a white solid. Yield 0.17 g.

MS: APCI(+ve) 459 (M+1, 100%)

$^1$H NMR: δ (CDCl$_3$+DMSO) 1.53(6H, d), 2.17(3H, s), 2.26(2H, m), 2.30(3H, s), 2.66(2H, d), 3.08(2H, s), 4.14(2H, m), 7.07(1H, m), 7.20(2H, m), 7.42(1H, m), 7.48(1H, m), 7.82(1H, d), 7.95(1H, d), 8.16(1H, s), 8.77(1H, s), 9.49(1H, s)

MP: 236–8° C.

EXAMPLE 63 cis-2-[4-(3-Aminocarbonylbenzenesulphonyl)-3,5-dimethylpiperazin-1-yl]-N-(2-methylphenyl)acetamide

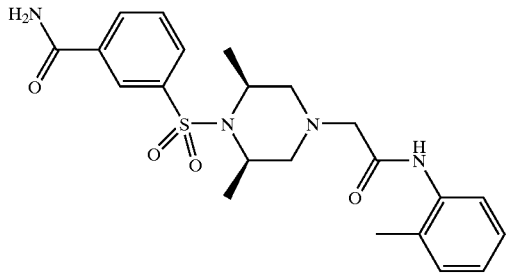

Hydrgen chloride gas was bubbled through a solution of the product of Example 55 step (ii) (0.21 g), in methanol (50 ml) at 0° C. for 4 hours. The mixture was evaporated to dryness, the residue was dissolved in methanol and ethylenediamine (0.18 g) was added. After 3 hours LC/MS indicated mainly amide. After 18 hours the mixture was evaporated to dryness, the residue was triturated with ether/ethanol, filtered and the solid was purified by chromatography on silica gel eluting with dichloromethane containing ethanol (2.5–5%) to give the title compound as a white solid. Yield 0.08 g.

MS: APCI(+ve) 445 (M+1, 100%)

$^1$H NMR: δ (CDCl$_3$+DMSO) 1.54(6H, d), 2.13(2H, m), 2.29(3H, s), 2.70(2H, d), 3.06(2H, s), 4.14(2H, m), 6.24(1H, br s), 7.07(1H, m), 7.21(2H, m), 7.60(1H, t), 7.68(1H, br s), 7.93(2H, d), 8.15(1H, d), 8.41(1H, s), 8.74(1H, s)

MP: 124–5° C.

EXAMPLE 64 cis-2-[4-(3-Methanesulphonylaminobenzenesulphonyl)-3,5-dimethylpiperazin-1-yl]-N-(2-methylphenyl)acetamide

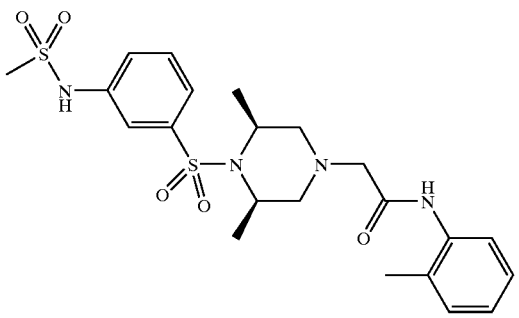

The title compound was prepared from the product of Example 57 and methane sulphonyl chloride by the method of Example 62. The solid obtained at the end of the reaction was suspended in ethanol (50 ml) to which a solution of K$_2$CO$_3$ (0.2 g) in water (10 ml) was added, and stirred for 18 hours, in order to hydrolyse any bis-sulphonamide. The ethanol was removed, water (50 ml) was added and the pH was adjusted to 5.0. The solid was filtered off, washed with water and ether and dried in vacuo to give the title compound as a white solid. Yield 0.13 g.

MS: APCI(+ve) 495 (M+1, 100%)

$^1$H NMR: δ (CDCl$_3$) 1.54(6H, d), 2.20(2H, m), 2.30(3H, s), 2.68(2H, d), 3.06(3H, s), 3.09(2H, s), 4.13(2H, m), 7.07(1H, m), 7.20(2H, m), 7.25(1H, s), 7.40(1H, d of d), 7.48(1H, t), 7.60(1H, d), 7.68(1H, m), 7.95(1H, d), 8.73(1H, s)

MP: 102–3° C.

EXAMPLE 65 cis-2-[4-(2-Methanesulphonylbenzenesulphonyl)-3,5-dimethylpiperazin-1-yl]-N-(3-methoxy-2-methylphenyl)acetamide

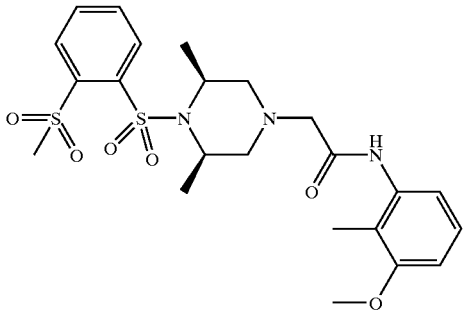

i) cis-[3,5-Dimethylpiperazin-1-yl]-N-(3-methoxy-2-methylphenyl)acetamide

The subtitle compound was prepared from 2-chloro-N-(3-methoxy-2-methylphenyl)acetamide (10.72 g) and cis-2,6-dimethylpiperazine (6.29 g) by the method of Example 58 step (i) as a tan solid. Yield: 13.13 g $^1$H NMR δ (CDCl$_3$) 9.32(bs, 1H), 7.79(d, 1H), 7.18(t, 1H), 6.68(d, 1H), 3.83(s, 3H), 3.14(s, 2H), 2.93–3.04(m, 2H), 2.81–2.85(m, 2H), 2.14(s, 3H), 1.92(t, 2H), 1.10(d, 6H)

ii) cis-2-[4-(2-Methanesulphonylbenzenesulphonyl)-3,5-dimethylpiperazin-1-yl]-N-(3-methoxy-2-methylphenyl)acetamide The title compound was prepared from the product of step (i) (0.503 mmol) and 2-methanesulphonylbenzenesulphonyl chloride (0.503 mmol) by the method of Example 58 step (ii) as a white solid. Yield: 6 mg MS: APCI(+ve) 510 (M+1)

$^1$H NMR δ (CD$_3$OD) 8.4(m, 1H), 8.3(m, 1H), 7.91–7.89 (m, 2H), 7.16–7.18(m, 2H), 6.8(t, 1H), 40.2(m, 2H), 3.84(s, 3H), 3.43(s, 3H), 3.14(s, 2H), 2.74(d, 2H), 2.33(dd, 2H), 2.14(s, 3H), 1.61(d, 6H)

EXAMPLE 66 cis-2-[4-(2-Methanesulphonylbenzenesulphonyl)-3,5-dimethylpiperazin-1-yl]-N-(3-fluoro-2-methylphenyl)acetamide

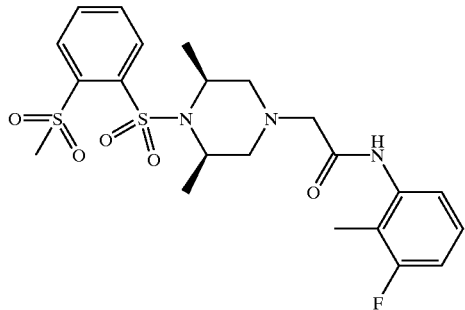

The title compound was prepared from the product of Example 60 step (i) (0.503 mmol) and 2-methanesulphonylbenzenesulphonyl chloride (0.503 mmol) by the method of Example 58 step (ii) as a white solid. Yield: 17 mg MS: APCI(+ve) 498 (M+1)

$^1$H NMR δ (CD$_3$OD) 8.4(m, 1H), 8.3(m, 1H), 7.89–7.91 (m, 2H), 7.4(d, 1H), 7.1(q, 1H), 6.9(t, 1H), 4.2(m, 2H), 3.44(s, 3H), 3.16(s, 2H), 2.74(d, 2H), 2.3(dd, 1H), 2.20(d, 2H), 1.62(d, 6H)

EXAMPLE 67 cis-2-[4-(1-Methylimidazol-4-sulphonyl-4-yl)-3,5-dimethylpiperazin-1-yl]-N-(quinolin-5-yl)acetamide

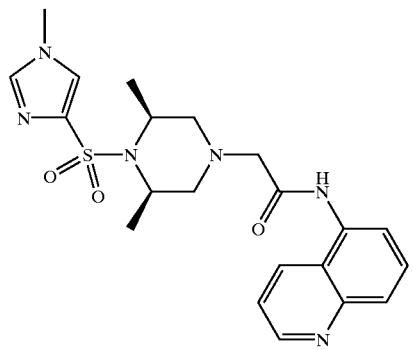

The title compond was prepared from the product of Example 58 step (i) (0.503 mmol) and 1-methylimidazole-4-sulphonyl chloride (0.503 mmol) by the method of Example 58 step (ii) as a white solid. Yield: 16 mg MS: APCI(+ve) 443 (M+1)

$^1$H NMR δ (CD$_3$OD) 8.90(d, 1H), 4.45(d, 1H), 7.97(t, 1H), 7.82(s, 1H), 7.80(d, 1H), 7.68(s, 1H), 7.58–7.63(m, 1H), 4.17–2.21(m, 2H), 3.79(s, 3H), 3.26(s, 2H), 2.80(d, 2H), 2.25(dd, 2H), 1.58(d, 6H)

EXAMPLE 68 cis-2-[4-(1-Methylimidazol-4-sulphonyl-4-yl)-3,5-dimethylpiperazin-1-yl]-N-(3-methoxy-2-methylphenyl)acetamide

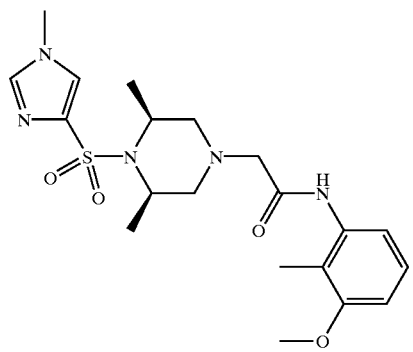

The title compound was prepared from the product of Example 65 step (i) (0.503 mmol) and 1-methylimidazol-4-sulphonyl chloride (0.503 mmol) by the method of Example 58 step (ii) as a white solid. Yield: 31 mg MS APCI(+ve) 436 (M+1)

$^1$H NMR δ (CD$_3$OD) 7.77(s, 1H), 7.67(s, 1H), 7.16–7.18 (m, 2H), 6.82–6.85(m, 1H), 4.14–4.18(m, 2H), 3.84(s, 3H), 3.79(s, 3H), 3.10(s, 2H), 2.72(d, 2H), 2.20(dd, 2H), 2.13(s, 3H), 1.53(d, 6H)

EXAMPLE 69 cis-2-[4-(1-Methylimdazol-4-sulphonyl-4-yl)-3,5-dimethylpiperazin-1-yl]-N-(3-fluoro-2-methylphenyl)acetamide

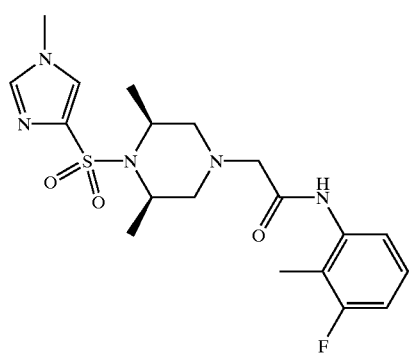

The title compound was prepared from the product of Example 60 step (i) (0.503 mmol) and 1-methylimidazol-4-sulphonyl chloride (0.503 mmol) by the method of Example 58 step (ii) as a white solid. Yield: 21 mg MS: APCI(+ve) 424 (M+1)

$^1$H NMR δ (CD$_3$OD) 7.77(s, 1H), 7.67(s, 1H), 7.43(d, 1H), 7.20(q, 1H), 6.95(t, 1H), 4.12–4.20(m, 2H), 3.79(s, 3H), 3.12(s, 2H), 2.72(d, 2H), 2.17–2.23(m, 5H), 1.54(d, 6H)

EXAMPLE 70 cis-2-[4-(3-Methanesulphonylbenzenesulphonyl)-3,5-dimethylpiperazin-1-yl]-N-(2-trifluoromethylphenyl)acetamide

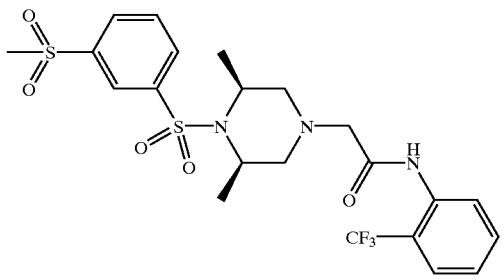

i) 2-Chloro-N-(2-trifluoromethylphenyl)acetamide

The subtitle compound was prepared from 2-trifluoromethylaniline(10.5 g) and chloroacetyl chloride (6.8 ml) by the method of Example 33 step (iii) as a white solid. Yield: 13.7 g MS: APCI(−ve) 236 (M−1)

ii) cis-3,5-Dimethylpiperazin-1-yl]-N-(2-trifluoromethylphenyl)acetamide

The subtitle compound was prepared from the product of step (i) (7.6 g) and cis-2,6-dimethylpiperazine (3.53 g) by the method of Example 58 step (i) as a white solid. Yield: 8.57 g MS: APCI(+ve) 316 (M+1)

iii) cis-2-[4-(3-Methanesulphonylbenzenesulphonyl)-3,5-dimethylpiperazin-1-yl]-N-(2-trifluoromethylphenyl)acetamide The product of step (iii) (0.25 g) and 3-methanesulphonylbenzenesulphonyl chloride (0.606 g), potassium carbonate (0.275 g) in 2,6-lutidine (0.5 ml) were heated in a 100 Watt microwave oven at 120° C. for 10 min. The mixture was then partitioned between dichloromethane and water. The organic phase collected, dried (MgSO$_4$), and the solvent evaporated under reduced pressure. Purification was by revese phase HPLC eluting with 1% aq. ammonium acetate/acetonitrile (95% to 60%) to give the title compound as a white solid. Yield: 0.1 g MS: APCI(+ve) 534 (M+1)

$^1$H NMR δ (CDCl$_3$) 9.16(bs, 1H), 8.41(s, 1H), 8.30(d, 1H), 8.20(d, 1H), 7.58(t, 1H), 7.26(d, 1H), 4.15(m, 2H)

EXAMPLE 71 cis-2-[4-(2-Aminoethylaminocarbonylbenzenesulphonyl)-3,5-dimethylpiperazin-1-yl]-N-(2-methylphenyl)acetamide

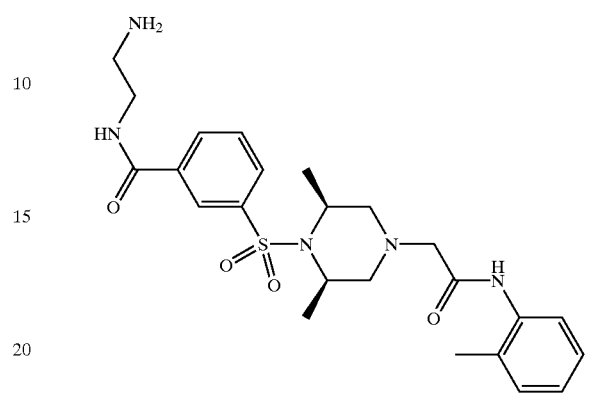

The title compound was prepared from the product of Example 55 by the method of Example 63 followed by addition of ethylenediamine, the mixture was heated at reflux for 5 hours, evaporated to dryness and the residue was crystallised from ethanol to give the title compound as a white solid. Yield 0.15 g MS: APCI(+ve) 488 (M+1, 100%)

$^1$H NMR: δ (CDCl$_3$) 1.56(8H, m), 2.17(2H, m), 2.29(3H, s), 2.68(2H, d), 2.98(2H, t), 3.06(2H, s), 3.51(2H, m), 4.14(2H, m), 6.97(1H, br t), 7.07(1H, m), 7.20(2H, m), 7.60(1H, t), 7.9(3H, m), 8.25(1H, m), 8.71(1H, br s)

MP: 90–2° C.

EXAMPLE 72 cis-2-[4-(1,1,2,2-Tetrahydroisoquinilin-7-sulphonyl-7-yl)-3,5-dimethylpiperazin-1-yl]-N-(2,6-dimethylphenyl)acetamide

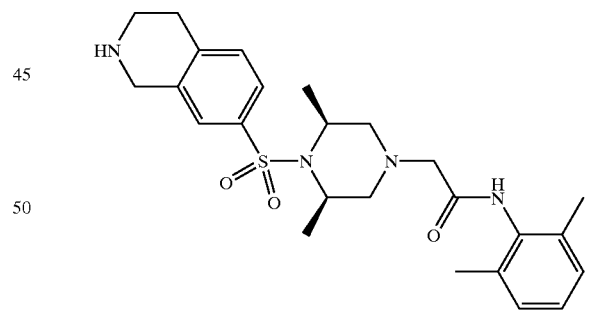

i) cis-3,5-Dimethylpiperazin-1-yl]-N-(2,6-dimethylphenyl)acetamide

The subtitle compound was prepared from 2-chloro-N-(2,6-dimethylphenyl)acetamide (6.54 g) and cis-2,6-dimethylpiperazine (3.78 g) by the method of Example 58 step (i) as a white solid. Yield: 7.85 g MS: APCI(+ve): 276 (M+1)

ii) cis-2-[4-Trifluoroacetyl(1,1,2,2-tetrahydroisoquinilin)-7-sulphonyl-7-yl)-3,5-dimethylpiperazin-1-yl]-N-(2,6-dimethylphenyl)acetamide The subtitle compound was prepared from the product of step (i) (0.165 g) and N-trifluoroacetyl(1,1,2,2- tetrahydroisoquinolin)-7-sulphonyl chloride (0.39 g) by the method of Example 58 step (ii) as a white solid. Yield: 96 mg MS: APCI(+ve) 567 (M+1)

iii) cis-2-[4-(1,1,2,2-Tetrahydroisoquinilin-7-sulphonyl-7-yl)-3,5-dimethylpiperazin-1-yl]-N-(2,6-dimethylphenyl) acetamide The product from step (ii) (90 mg), potassium carbonate (200 mg) in water (10 ml) and methanol (15 ml) were heated at reflux for 2 h. Water (50 ml) was added and the mixture extracted with ethyl acetate. The organic phase collected, dried (MgSO$_4$) and solvent evaporated under reduced pressure to give the title compound as a white solid. Yield: 55 mg MS: APCI(+ve) 471 (M+1)

$^1$H NMR δ (CDCl$_3$) 8.29(s, 1H), 7.55(d, 1H), 7.50(s, 1H), 7.17(d, 1H), 7.11(m, 3H), 4.14(m, 2H), 4.06(s, 2H), 3.48(q, 1H), 3.17(t, 1H), 3.12(s, 2H), 2.87(t, 2H), 2.72(d, 2H), 2.25(d, 1H), 2.22(s, 6H), 2.05(s, 1H), 1.69(bs, 1H), 1.51(d, 6H), 1.19–1.28(m, 4H)

EXAMPLE 73 cis-2-[4-(3-Cyanobenzenesulphonyl)-3,5-dimethylpiperazin-1-yl]-N-(2,6-dimethylphenyl) acetamide

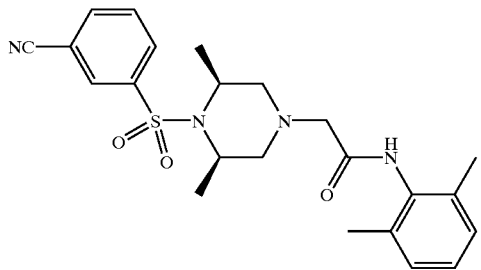

The title compound was prepared from the product of Example 72 step (i) (0.165 g) and 3-cyanobenzenesulphonyl chloride (0.15 g) by the method of Example 58 step (ii) as a white solid. Yield: 40 mg MS: APCI(+ve) 441 (M+1)

$^1$HNMR (CDCl$_3$) 8.22(s, 1H), 8.13(s, 1H), 8.05(d, 1H), 7.86(d, 1H), 7.67(t, 1H), 7.12(m, 3H), 4.15(m, 2H), 3.14(s, 2H), 2.78(d, 2H), 2.22(s, 8H), 1.54(d, 6H)

EXAMPLE 74 cis-2-[4-(4-Cyanobenzenesulphonyl)-3,5-dimethylpiperazin-1-yl]-N-(2-methylphenyl) acetamide

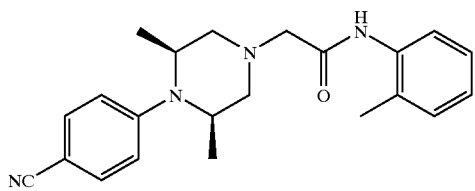

4-Cyanobenzenesulphonyl chloride (0.36 g) was added to a stirred mixture of the product of Example 55 step (i) (0.5 g) and potassium carbonate (0.62 g) in 1-methyl-2-pyrrolidinone (3 ml). After 20 min the reaction mixture was partitioned between ethyl acetate and water. The organic phase was washed with water and brine, dried (MgSO$_4$) and evaporated under reduced pressure. Purification was by flash chromatography eluting with 1% ethanol in dichloromethane followed by trituration with methanol to give the title compound as a white crystalline solid. Yield 55 mg.

MS: ES (+ve) 427 (M+1)

$^1$H NMR: δ (CDCl$_3$) 8.67(1H, brs), 7.99–7.93(3H, m), 7.83(2H, d), 7.21(2H, m), 7.08(1H, m), 4.14(2H, m), 3.10 (2H, s), 2.73(2H, d), 2.30(3H, s), 2.18(2H, dd), 1.57(3H, s), 1.54(3H, s).

EXAMPLE 75 cis-2-[4-(2-Cyanobenzenesulphonyl)-3,5-dimethylpiperazin-1-yl]-N-(2,6-dimethylphenyl) acetamide, hydrochloride salt

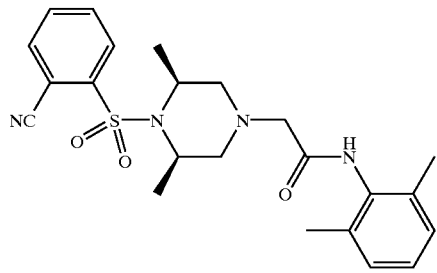

The free base of the title compound was prepared from the product of Example 72 step (i) (0.165 g) and 2-cyanobenzenesulphonyl chloride (0.15 g) by the method of Example 58 step (ii). The title compound was prepared by adding 1M hydrogen chloride in diethyl ether to a solution of the free base to produce a white precipitate. This was filtered and further washed with diethyl ether to give the title compound as a white solid. Yield: 20 mg MS: APCI(+ve) 441 (M+1)

$^1$H NMR δ (CDCl$_3$) 8.19(bs, 1H), 7.91(bs, 1H), 7.78(bs, 2H), 7.10(m, 3H), 4.40(bs, 2H), 4.20(bs, 2H), 3.50(m, 3H), 2.20(s, 6H), 2.00–1.40(m, 6H)

EXAMPLE 76 cis-2-[4-(3-Cyanobenzenesulphonyl)-3,5-dimethylpiperazin-1-yl]-N-(2-chlorophenyl) acetamide

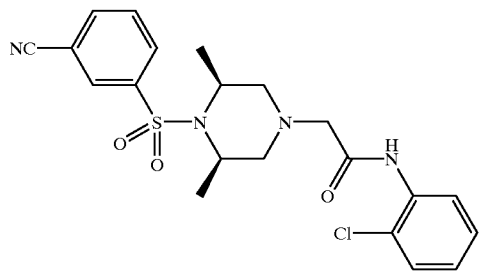

The title compound was prepared from the product of Example 15 step (ii) (0.2 g) and 3-cyanobenzenesulphonyl chloride (0.28 g) by the method of Example 74 as a white solid. Yield 8 mg.

MS: APCI (+ve) 447 (M+1)

$^1$H NMR: δ (CDCl$_3$) 9.45(1H, brs), 8.49(1H, dd), 8.13 (1H, s), 8.05(1H, d), 7.87(1H, d), 7.68(1H, t), 7.38(1H, d), 7.29(1H, m), 7.06(1H, t), 4.14(2H, m), 3.11(2H, s), 2.72(2H, d), 2.18(1H, dd), 1.60(3H, s), 1.58(3H, s).

EXAMPLE 77

2-[8-(Isquinolin-1-yl)-3,8-diazabicyclo[3.2.1]oct-3-yl]-N-(2-methylphenyl)acetamide

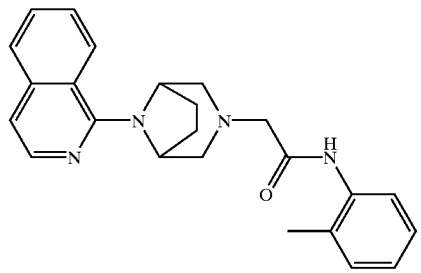

The title compound was prepared from the product Example 20 step (iv) (0.32 g) and 1-chloroisoquinoline (0.14 g) by the method of Example 52 step (i) as a beige solid. Yield: 40 mg MS: ESI(+ve) 387 (M+1)

$^1$H NMR δ (DMSO) 9.21(bs, 1H), 8.20(d, 1H), 8.00(d, 1H) 7.93(d, 2H), 7.70(t, 1H), 7.60(t, 1H), 7.35(d, 1H), 7.20(m, 2H), 7.06(t, 1H), 4.40(bs, 2H), 2.98(d, 2H), 2.85(d, 2H), 2.30(s, 3H), 2.00(d, 2H), 1.90(m, 2H)

EXAMPLE 78 cis-2-[4-(4-Acetamidobenzenesulphonyl)-3,5-dimethylpiperazin-1-yl]-N-(2-methylphenyl)acetamide

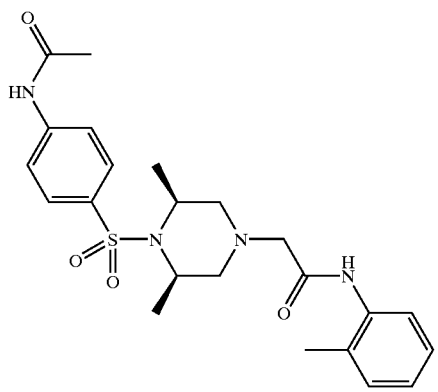

2,6-Lutidine (0.3 ml) was added to a mixture of 4-acetamidobenzenesulphonyl chloride (0.25 g), potassium carbonate (0.18 g) and the product of Example 55 step (i) (0.14 g). The reaction mixture was heated at 100° C. for 5 minutes in a 100 Watt microwave oven, allowed to cool and partitioned between dichloromethane and water. The organic phase was washed with brine, dried (MgSO$_4$) and evaporated under reduced pressure. Purification was by reverse phase HPLC (acetonitile/1% aq. ammonium acetate). Yield 15 mg.

MS: AP (+ve) 459 (M+1)

$^1$H NMR: δ (DMSO) 10.35(1H, s), 7.76(4H, q), 7.55(1H, d), 7.22–7.14(2H, m), 7.07(1H, m), 4.00(2H, m), 3.02(2H, s), 2.64(2H, d), 2.20(3H, s), 2.09(3H, s), 1.92(2H, dd), 1.42(3H, s), 1.40(3H, s)

EXAMPLE 79 cis-2-[4-(3-Cyanobenzenesulphonyl)-3,5-dimethylpiperazin-1-yl]-N-(2-trifluoromethylphenyl)acetamide

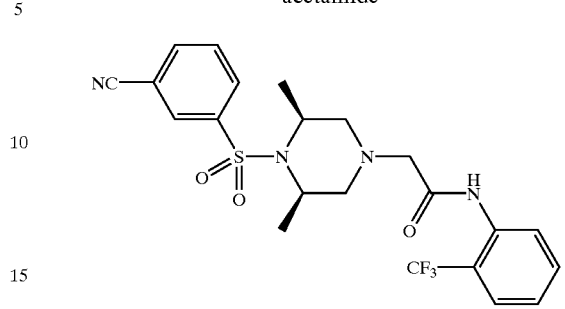

The title compound was prepared from the product of Example 70 step (i) (0.189 g) and 3-cyanobenzenesulphonyl chloride (0.15 g) by the method of Example 58 step (ii) as a white solid. Yield: 17 mg MS: APCI(+ve) 481 (M+1)

$^1$H NMR δ (DMSO) 8.98(bs, 1H), 8.11(m, 2H), 7.93(m, 2H), 7.05(m, 4H), 4.10(m, 2H), 3.30(s, 2H), 2.90(d, 2H), 2.40(bd, 2H), 1.50(d, 6H)

EXAMPLE 80 cis-2-[4-(3-Cyanobenzenesulphonyl)-3,5-dimethylpiperazin-1-yl]-N-(2-methyl-5-methanesulphonamidophenyl)acetamide

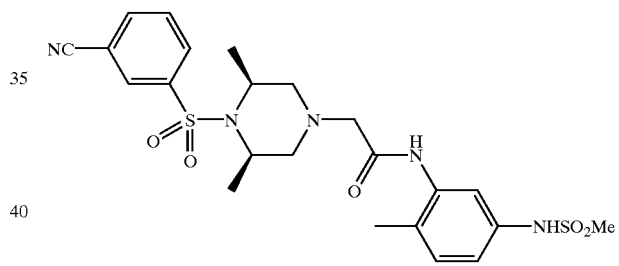

i) cis-1-(3-Cyanobenzenesulphonyl)-2,6-dimethyl-4-phenylmethylpiperazine

A solution of cis-4-benzyl-2,6-dimethylpiperazine (1 g), 4-N,N-dimethylaminopyridine (0.54 g), 3-cyanobenzenesulphonyl chloride (2.13 g) in pyridine (3 ml) were stirred at ambient temperature. After 1 h the mixture was partitioned between dichloromethane and water. The organic phase further washed with brine, collected, dried, (MgSO$_4$) and solvent evaporated under reduced pressure to leave the subtitle compound as an orange gum. Yield: 1 g MS: APCI(+ve) 370 (M+1)

ii) cis-1-(3-Cyanobenzenesulphonyl)-2,6-dimethylpiperazine

A solution of the product from step (i) (1 g) in 1,2-dichloroethane (10 ml) was treated with 1-chloroethyl chloroformate (0.44 ml). The mixture was heated at 80° C. for 16 h. The solvents were then evaporated under reduced pressure and the residue dissolved in methanol (50 ml). The mixture then heated at 50° C. for 1 h. The solvents were then evaporated under reduced pressure. Purification was by trituration with ethyl acetate and filtration to give the subtitle compound as a white solid. Yield: 0.85 g MS: APCI(+ve) 279 (M+1)

iii) cis-2-[4-(3-Cyanobenzenesulphonyl)-3,5-dimethylpiperazin-1-yl]-N-(2-methyl-5-bis(methanesulphonyl)amidophenyl)acetamide A solution of the product from step (ii) (0.5 g) and the product of Example 24 step (i) (0.8 g), N,N-diisopropylethylamine (0.6 ml), potassium iodide (2 mg) in 1-methyl-2-pyrrolidinone (10 ml) were heated at 90° C. for 3 h. The mixture was then partitioned dichloromethane and water. The organic phase collected, further washed with brine, dried (MgSO$_4$) and solvent evaporated under reduced pressure to give the subtitle compound as a brown foam.

Yield: 1.04 g

MS: APCI(+ve) 597 (M+1)

iv) cis-2-[4-(3-Cyanobenzenesulphonyl)-3,5-dimethylpiperazin-1-yl]-N-(2-methyl-5-methanesulphonamidophenyl)acetamide The product from step (iii) (1 g), potassium carbonate (1 g), water (10 ml) and tetrahydrofuran (20 ml) were stirred at ambient temperature for 16 h then heated at 90° C. for 6 h. The mixture partitioned between dichloromethane and water. The organic phase collected, dried (MgSO$_4$) and solvent evaporated under reduced pressure. Purification was by silica gel chromatography eluting with iso-hexane/ethyl acetate (1:9) to give the title compound as a white solid. Yield: 0.5 g MS: APCI(+ve) 520 (M+1), APCI(-ve) 518 (M-1)

$^1$HNMR δ (CDCl$_3$) 8.9(bs, 1H), 8.13(2×s, 2H), 8.05(d, 1H), 7.90(d, 1H), 7.70(t, 1H), 7.40(bs, 1H), 7.10(m, 2H), 4.10(m, 2H), 3.10(s, 2H), 2.95(s, 3H), 2.70(d, 2H), 2.30(s, 3H), 2.20(m, 2H), 1.60(d, 6H)

EXAMPLE 81

2-[8-(4-Benzenesulphonyl)-3,8-diazabicyclo[3.2.1]oct-3-yl]-N-(2-methylphenyl)acetamide

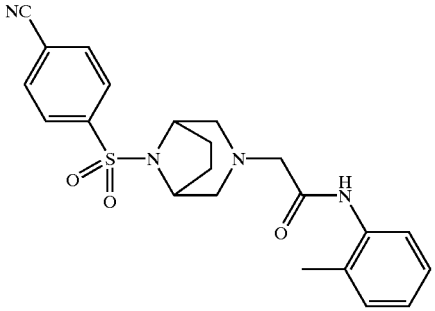

The title compound was prepared from the product of Example 20 step (iv) (0.34 mmol) and 4-cyanobenzenesulphonyl chloride (0.34 mmol) by the method of Example 58 step (ii) as a white solid. Yield: 10 mg MS: ESI(+ve) 425 (M+1)

$^1$H NMR δ (CDCl$_3$) 8.68(bs, 1H), 8.05(m, 3H), 7.83(d, 2H), 7.23–7.17(m, 2H), 7.07(m, 1H), 4.26(m, 2H), 3.19(s, 2H), 2.86(dd, 2H), 2.65(d, 2H), 2.27(s, 3H), 1.94(m, 2H), 1.74(m, 2H)

EXAMPLE 82

2-[8-(2-Benzenesulphonyl)-3,8-diazabicyclo[3.2.1]oct-3-yl]-N-(2-methylphenyl)acetamide

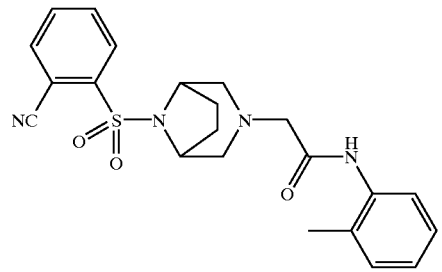

The title compound was prepared from the product of Example 20 step (iv) (0.34 mmol) and 2-cyanobenzenesulphonyl chloride (0.34 mmol) by the method of Example 58 step (ii) as a white solid. Yield: 8 mg MS: APCI(+ve) 425 (M+1)

$^1$H NMR δ (CDCl$_3$) 8.77(bs, 1H), 8.15(dd, 1H), 8.03(d, 1H), 7.88(ss, 1H), 7.78–7.69(m, 2H), 7.25–7.18(m, 2H), 7.07(t, 1H), 4.36(m, 2H), 3.20(s, 3H), 2.85(dd, 1H), 2.74(d, 1H), 2.30(s, 3H), 2.07–1.99(m, 4H)

EXAMPLE 83 cis-2-[4-(1,2-Dimethylimidazol-4-sulphonyl-4-yl)-3,5-dimethylpiperazin-1-yl]-N-(quinolin-5-yl)acetamide

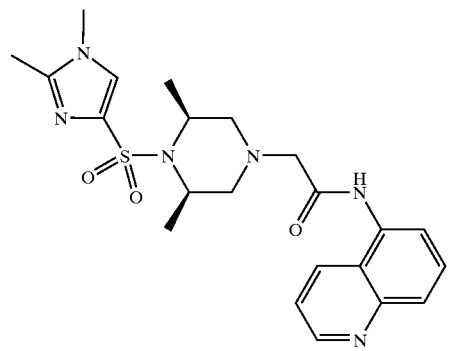

The title compound was prepared from the product of Example 58 step (i) (0.503 mmol) and 1,2-dimethylimidazole-4-sulphonyl chloride (0.503 mmol) by the method of Example 58 step (ii) as a white solid. Yield: 20 mg MS: APCI(+ve) 457 (M+1)

$^1$H NMR δ (CD$_3$OD) 8.88–8.89(m, 1H), 8.44(d, 1H), 7.97–7.94(m, 1H), 7.76–7.81(m, 2H), 7.56–7.60(m, 2H), 4.19–4.13(m, 2H), 3.65(s, 3H), 3.25(s, 2H), 2.79(d, 2H), 2.38(s, 3H), 2.54(dd, 2H), 1.55(d, 6H)

EXAMPLE 84 cis-2-[4-(S-Chloro-1,3-dimethylpyrazole-4-sulphonyl-4-yl)-3,5-dimethylpiperazin-1-yl]-N-(3-methoxy-2-methylphenyl)acetamide

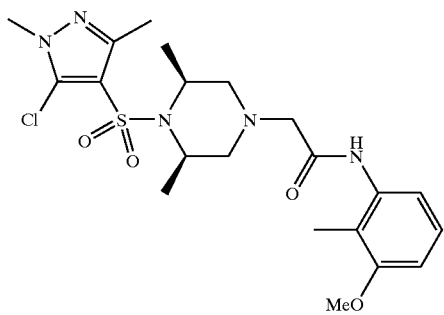

The title compound was prepared from the product of Example 65 step (i) (0.503 mmol) and 5-chloro-1,3-dimethyl-4-sulphonyl chloride (0.503 mmol) by the method of Example 58 step (ii) as a white solid. Yield: 6 mg MS: APCI(+ve) 485 (M+1)

$^1$H NMR δ (CD$_3$OD) 7.15–7.16(m, 2H), 6.81–6.84(m, 1H), 4.07–4.10(m,2H), 3.83(s, 3H), 3.82(s, 3H), 3.15(s, 2H), 2.79(d, 2H), 2.37(s, 3H), 2.56(dd, 2H), 2.12(s, 3H), 1.54(d, 6H)

EXAMPLE 85

2-[8-(2-(Isoxazol-3-yl)thiophen-5-yl)-3,8-diazabicyclo[3.2.1]oct-3-yl]-N-(2-methylphenyl)acetamide

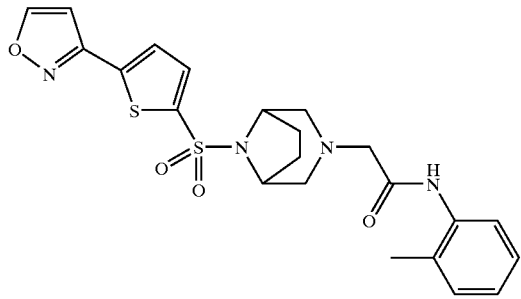

The title compound was prepared from the product of Example 20 step (iv) (0.34 mmol) and 2-(isoxazol-3-yl)thiophenesulphonyl chloride (0.34 mmol) as a white solid. Yield: 10 mg MS: ESI(+ve) 473 (M+1)

$^1$H NMR δ (CDCl$_3$) 8.72(bs, 1H), 8.05(d, 1H), 7.61(d, 1H), 7.46(d, 1H), 7.23(d, 2H), 7.06(t, 1H), 6.53(d, 1H), 4.33(m, 2H), 3.22(s, 2H), 2.89(dd, 2H), 2.73(d, 2H), 2.28(s, 3H), 1.94(m, 2H), 1.87(m, 2H)

EXAMPLE 86

2-[8-(1,1,2,2-Tetrahydroisoquinilin-7-sulphonyl)-3,8-diazabicyclo[3.2.1]oct-3-yl]-N-(2-methylphenyl)acetamide

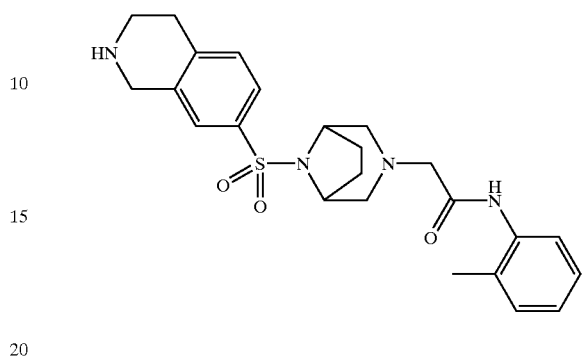

The title compound was prepared from the product of Example 20 step (iv) (0.34 mmol) and N-trifluoroacetyl-1,1,2,2-tetrahydroisoquinoline-7-sulphonyl chloride (0.34 mmol) by the method of Example 58 step (ii) followed by the method of Example 72 step (iii) as a white solid. Yield: 26 mg MS: ESI(+ve) 551 (M+1)

$^1$H NMR δ (CDCl$_3$) 8.73(bs, 1H), 8.04(d, 1H), 7.77–7.68 (m, 2H), 7.33(t, 1H), 7.25–7.17(m, 2H), 7.06(t, 1H), 4.83(d, 2H), 4.24(m, 2H), 3.92(dt, 2H), 3.19(s, 2H), 3.05(m, 2H), 2.85(dd, 2H), 2.66(d, 2H), 2.27(s, 3H), 1.90(m, 2H), 1.76(d, 2H)

EXAMPLE 87 cis-2-[4-(5-Chloro-1,3-dimethylpyrazole-4-sulphonyl-4-yl)-3,5-dimethylpiperazin-1-yl]-N-(2-methylphenyl)acetamide

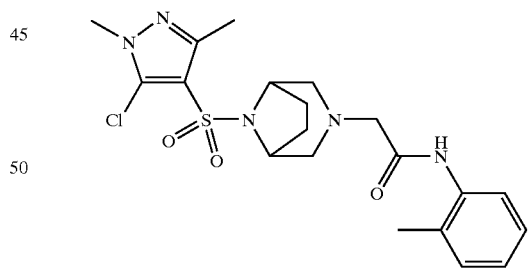

The title compound was prepared from the product of Example 20 step (iv) (0.34 mmol) and 5-chloro-1,3-dimethylpyrazole-4-sulphonyl chloride (0.34 mmol) by the method of Example 58 step (ii) as a white solid. Yield: 12 mg MS: ESI (+ve) 452 (M+1)

$^1$H NMR δ (CDCl$_3$) 8.77(bs, 1H), 8.04(d, 1H), 7.23–7.18 (m, 2H), 7.07(t, 1H), 4.25(m, 2H), 3.83(s, 3H), 3.19(s, 2H), 2.85(dd, 2H), 2.65(d, 2H), 2.43(s, 3H), 2.30(s, 3H), 1.95(s, 4H)

EXAMPLE 88 cis-2-[4-(3,5-Dimethylisoxazole-4-sulphonyl-4-yl)-3,5-dimethylpiperazin-1-yl]-N-(2-methylphenyl)acetamide

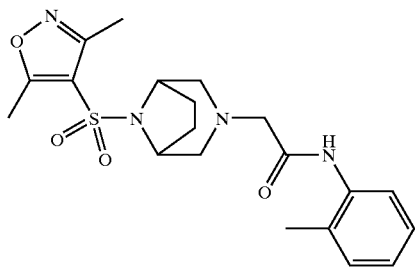

The title compound was prepared from the product of Example 20 step (iv) (0.34 mmol) and 3,5-dimethylisoxazole-4-sulphonyl chloride (0.34 mmol) by the method of Example 58 step (ii) as a white solid. Yield: 5.6 mg MS: ESI (+ve) 419 (M+1)

$^1$H NMR δ (CDCl$_3$) 8.72(bs, 1H), 8.04(d, 1H), 7.21(t, 2H), 7.08(t, 1H), 4.18(m, 2H), 3.20(s, 2H), 2.88(dd, 2H), 2.66(s, 3H), 2.61(d, 2H), 2.44(s, 3H), 2.31(s, 3H), 2.03(m, 4H)

EXAMPLE 89 cis-2-[4-(2-Methanesulphonylbenzenesulphonyl)-3,5-dimethylpiperazin-1-yl]-N-(2-methylphenyl)acetamide

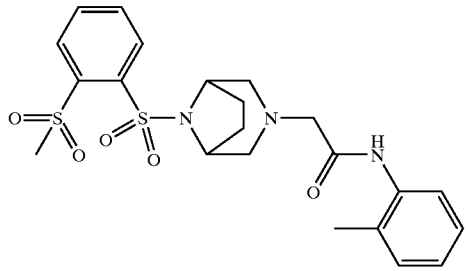

The title compound was prepared from the product of Example 20 step (iv) (0.34 mmol) and 2-methanesulphonylbenzenesulphonyl chloride (0.34 mmol) by the method of Example 58 step (ii) as a white solid. Yield: 13 mg MS: ESI (+ve) 478 (M+1)

$^1$H NMR δ (CDCl$_3$) 8.81(bs, 1H), 8.40(m, 1H), 8.28(m, 1H), 8.03(d, 1H), 7.80(m, 2H), 7.25–7.17(m, 2H), 7.06(t, 1H), 4.48(m, 2H), 3.46(s, 3H), 3.16(s, 2H), 2.82(dd, 2H), 2.68(d, 2H), 2.29(s, 3H), 1.95(d, 4H)

EXAMPLE 90 cis-2-[4-(3-Cyanobenzenesulphonyl)-3,5-dimethylpiperazin-1-yl]-N-(3-methoxy-2-methylphenyl)acetamide

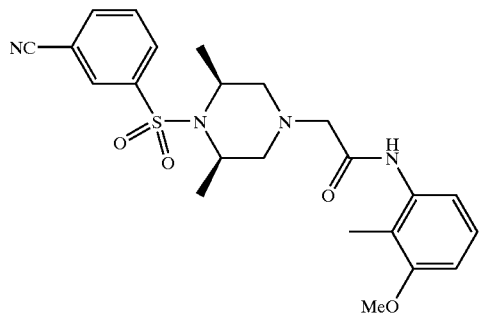

The title compound was prepared from the product of Example 65 step (i) (0.503 mmol) and 3-cyanobenzenesulphonyl chloride (0.503 mmol) by the method of Example 58 step (ii) as a white solid. Yield: 21 mg MS: ESI (+ve) 424 (M+1)

$^1$H NMR δ (CD$_3$OD) 7.77(s, 1H), 7.67(s, 1H), 7.43(d, 1H), 7.20(q, 1H), 6.95(t, 1H), 4.12–4.20(m, 2H), 3.78(s, 3H), 3.12(s, 2H), 2.72(d, 2H), 2.17–2.23(m, 5H), 1.54(d, 6H)

EXAMPLE 91 cis-2-[4-(4-Methanesulphonylbenzenesulphonyl)-3,5-dimethylpiperazin-1-yl]-N-(2-methylphenyl)acetamide

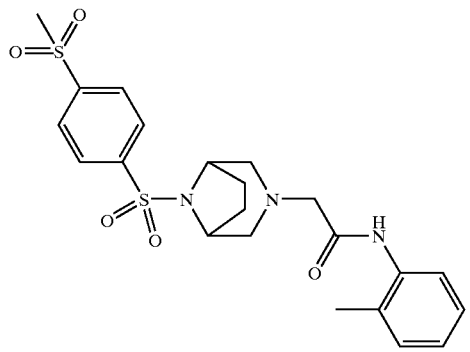

The title compound was prepared from the product of Example 20 step (iv) (0.34 mmol) and 4-methanesulphonylbenzenesulphonyl chloride (0.34 mmol) by the method of Example 58 step (ii) as a white solid. Yield: 25 mg MS: ESI (+ve) 478 (M+1)

$^1$H NMR δ (CDCl$_3$) 8.69(bs, 1H), 8.10(q, 4H), 8.04(d, 1H), 7.25–7.17(m, 2H), 7.07(t, 1H), 4.28(m, 2H), 3.20(s, 2H), 3.11(s, 3H), 2.87(dd, 2H), 2.67(d, 2H), 2.27(s, 3H), 1.93(m, 2H), 1.74(m, 2H)

EXAMPLE 92 cis-2-[4-(3-Cyanobenzenesulphonyl)-3,5-dimethylpiperazin-1-yl]-N-(5-cyano-2-methylphenyl)acetamide

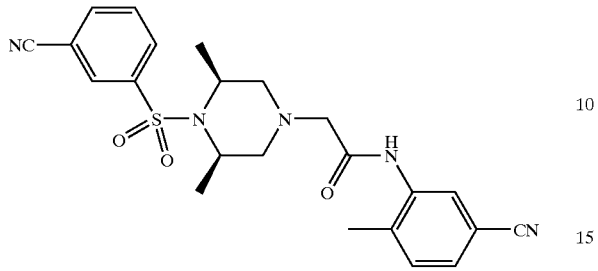

i) 2-Chloro-N-(5-cyano-2-methylphenyl)acetamide

The subtitle compound was prepared from 5-cyano-2-methylaniline (1.6 g) and chloroacetyl chloride (1.1 ml) by the method of Example 33 step (iii) as a white solid. Yield: 1.85 g MS: APCI (−ve) 207 (M−1)

ii) cis-2-[4-(3-Cyanobenzenesulphonyl)-3,5-dimethylpiperazin-1-yl]-N-(5-cyano-2-methylphenyl)acetamide The title compound was prepared from the product of step (i) (0.19 g) and the product from Example 80 step (ii) (0.2 g) by the method of Example 80 step (iii) as a white solid. Yield: 0.25 g MS: APCI(+ve) 452 (M+1)

$^1$H NMR δ (CDCl$_3$) 8.81(bs, 1H), 8.49(s, 1H), 8.13(s, 1H), 8.05(d, 1H), 7.90(d, 1H), 7.70(t, 1H), 7.29(d, 1H), 7.27(d. 1H), 4.20(m, 2H), 3.10(s, 2H), 2.70(d, 2H), 2.36(s, 3H), 2.20(m, 2H), 1.60(d, 6H)

EXAMPLE 93 cis-2-[4-(3-Cyanobenzenesulphonyl)-3,5-dimethylpiperazin-1-yl]-N-(5-acetamido-2-methylphenyl)acetamide

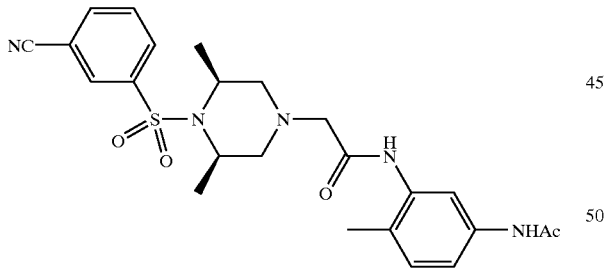

i) cis-2-Chloro-N-(5-acetamido-2-methylphenyl)acetamide

The subtitle compound was prepared from 5-acetamido-2-methylaniline (0.5 g) and chloroacetyl chloride (0.27 ml) by the method of Example 33 step (iii) as a beige solid. Yield: 0.55 g MS: APCI(+ve) 241 (M+1)

ii) cis-2-[4-(3-Cyanobenzenesulphonyl)-3,5-dimethylpiperazin-1-yl]-N—(5-acetamido-2-methylphenyl)acetamide The title compound was prepared from the product of step (i) (0.22 g) and the product of Example 80 step (ii) (0.2 g) by the method of Example 80 step (iii) as a white solid. Yield: 0.11 g MS: APCI(+ve) 468 (M+1)

$^1$H NMR δ (CDCl$_3$) 9.60(bs, 1H), 8.78(bs, 1H), 8.19(s, 1H), 8.17(d, 1H), 8.05(s, 1H), 7.98(d, 1H), 8.77(t, 1H), 7.75(s, 1H), 7.50(d, 1H), 7.10(d, 1H), 4.10(m, 2H), 2.75(d, 2H), 2.25(s, 3H), 2.16(m, 2H), 2.10(s, 3H), 1.50(d, 6H)

EXAMPLE 94

(R)-2-[4-(4-Cyanobenzenesulphonyl)-3-methylpiperazin-1-yl]-N-(quinolin-5-yl)acetamide

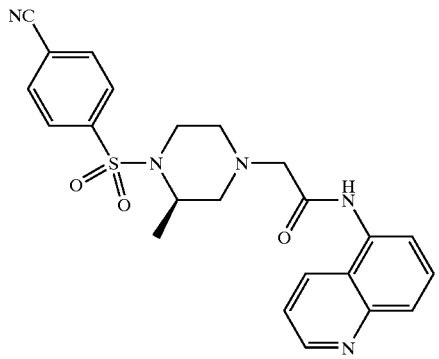

i) (R)-2-(3-Methylpiperazin-1-yl)-N-(quinolin-5-yl)acetamide

The subtitle compound was prepared from 2-chloro-N-(quinolin-5-yl)acetamide (1 g) (J Indian Chem Soc, 1940, 17, 619–621) and (R)-2-methylpiperazine (0.5 g) by the method of Example 58 step (i) as a white solid. Yield: 1.4 g MS: APCI(+ve) 285 (M+1)

ii) (R)-2-[4-(4-Cyanobenzenesulphonyl)-3-methylpiperazin-1-yl]-N-(quinolin-5-yl)acetamide The title compound was prepared from the product of step (i) (1.4 g) and 4-cyanobenzenesulphonyl chloride (1 g) by the method of Example 58 step (ii) as a white solid. Yield: 0.41 g MS: APCI(+ve) 450 (M+1)

$^1$H NMR δ (CDCl$_3$) 9.30(s, 1H), 8.95(d, 1H), 8.09(m, 2H), 7.99–7.94(m, 3H), 7.86–7.82(d, 2H), 7.73(m, 1H), 7.43(m, 1H), 4.27(m, 1H), 3.78(d, 1H), 3.42(m, 1H), 3.26(q, 2H), 2.98(d, 1H), 2.82(d, 1H), 2.55(dd, 1H), 2.39(m, 1H), 1.35(d, 3H)

EXAMPLE 95

(S)-2-[4-(4-Cyanobenzenesulphonyl)-3-methylpiperazin-1-yl]-N-(quinolin-5-yl)acetamide

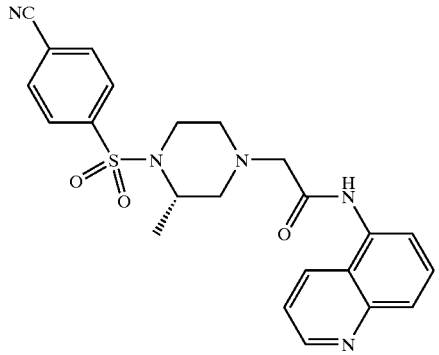

i) (S)-2-(3-Methylpiperazin-1-yl)-N-(quinolin-5-yl)acetamide to The subtitle compound was prepared from 2-chloro-N-(quinolin-5-yl)acetamide (1 g) (J Indian Chem Soc, 1940, 17, 619–621) and (S)-2-methylpiperazine (0.5 g) by the method of Example 58 step (i) as a white solid. Yield: 1.4 g MS: APCI(+ve) 285 (M+1)

ii) (S)-2-[4-(4-Cyanobenzenesulphonyl)-3-methylpiperazin-1-yl]-N-(quinolin-5-yl)acetamide The title compound was prepared from the product of step (i) (1.4 g) and 4-cyanobenzenesulphonyl chloride (1 g) by the method of Example 58 step (ii) as a white solid. Yield: 0.53 g MS: APCI(+ve) 450 (M+1)

$^1$H NMR δ (CDCl$_3$) 9.30(s, 1H), 8.95(d, 1H), 8.09(m, 2H), 7.99–7.94(m, 3H), 7.86–7.82(d, 2H), 7.73(m, 1H), 7.43(m, 1H), 4.27(m, 1H), 3.78(d, 1H), 3.42(m, 1H), 3.26(q, 2H), 2.98(d, 1H), 2.82(d, 1H), 2.55(dd, 1H), 2.39(m, 1H), 1.35(d, 3H)

EXAMPLE 96 cis-2-[4-(3-Cyanobenzenesulphonyl)-3,5-dimethylpiperazin-1-yl]-N-(2-methyl-5-methanesulphonylphenyl)acetamide

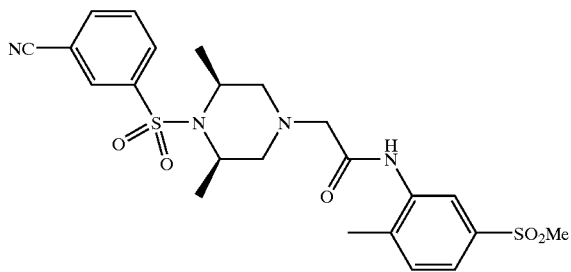

i) 2-Chloro-N-(2-methyl-5-methanesulphonylphenyl)acetamide

The subtitle compound was prepared from 5-methanesulphonyl-2-methylaniline (0.82 g) and chloroacetyl chloride (0.72 ml) by the method of Example 33 step (iii) as a beige solid. Yield: 0.61 g MS: APCI –ve) 260 (M–1)

ii) cis-2-[4-(3-Cyanobenzenesulphonyl)-3,5-dimethylpiperazin-1-yl]-N-(2-methyl-5-methanesulphonylphenyl)acetamide The title compound was prepared from the product of step (i) (0.14 g) and the product of Example 80 step (ii) by the method of Example 80 step (iii) as a white solid. Yield: 0.03 g MS: APCI(+ve) 505 (M+1)

$^1$H NMR δ (CDCl$_3$) 8.84(bs, 1H), 8.63(s, 1H), 8.10(s, 1H), 8.06(d, 1H), 7.90(d, 1H), 7:65(d, 1H), 7.64(d, 1H), 7.40(d, 1H), 4.25(m, 2H), 3.15(s, 2H), 3.07(s, 3H), 2.74(d, 2H), 2.40(s, 3H), 2.20(m, 2H), 1.60(d, 6H)

EXAMPLE 97 cis-2-[4-(3-Cyanobenzenesulphonyl)-3,5-dimethylpiperazin-1-yl]-N-(2-methyl-5-(4-amino-1-piperidinyl)methyl)phenyl]acetamide

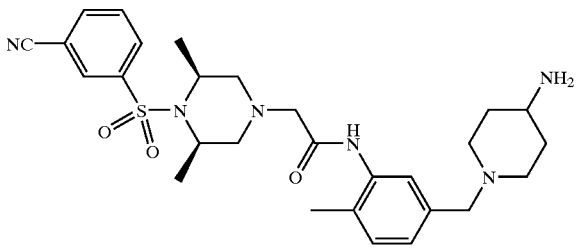

i) 2-Methyl-5-((1,1-dimethyl)-1-dimethylethyl)silyloxymethyl-aniline

A mixture of 2-methyl-5-hydoxymethylaniline (10 g), tert-butyldimethylsilyl chloride (10.84 g), imidazole (12.24 g) in dry N,N-dimethylformamide (80 ml) were stirred at ambient temperature for 18 h. The mixture was partitioned between ethyl acetate and saturated brine. The organic phase washed with water, collected, dried (MgSO$_4$) and solvent evaporated under reduced pressure to leave a brown gum which slowly crystalised on standing. Yield: 19.2 g MS: APCI(+ve) 252 (M+1)

ii) 2-Chloro-N-(2-methyl-5-((1,1-dimethyl)-1-dimethylethyl)silyloxymethyl)acetamide The subtitle compound was prepared from the product of step (i) (18.3 g) and chloroacetyl chloride (17.5 ml) by the method of Example 33 step (iii) as a beige solid. Yield: 23 g MS: APCI(–ve) 326 (M–1)

iii) cis-2-[4-(3-Cyanobenzenesulphonyl)-3,5-dimethylpiperazin-1-yl]-N-(2-methyl-5-((1,1-dimethyl)-1-dimethyl)silyloxymethyl)phenyl]acetamide The subtitle compound was prepared from the product of step (ii) (1.25 g) and the product of Example 80 step (ii) (1 g) by the method of Example 80 step (iii) as a beige foam. Yield: 1.3 g MS: APCI(+ve) 571 (M+1)

iv) cis-2-[4-(3-Cyanobenzenesulphonyl)-3,5-dimethylpiperazin-1-yl]-N-(2-methyl-5-hydroxymethyl)phenyl]acetamide A solution of the product of step (iii) (1.3 g) in tetrahydrofuran (9 ml) was treated with 1M tetrabutylammonium fluoride in tetrahydrofuran (2.6 ml) at ambient temperature. After stirring for 1.5 h the solvent was evaporated under reduced pressure to leave a brown gum. Purification was by silica gel chromatography eluting with ethyl acetate/isohexane (9:1) to give the subtitle compound as a white solid. Yield: 0.93 g MS: APCI(+ve) 457 (M+1)

v) cis-2-[4-(3-Cyanobenzenesulphonyl)-3,5-dimethylpiperazin-1-yl]-N-(2-methyl-5-iodomethyl)phenyl]acetamide The product from step (iv) (0.1 g) in tetrahydrofuran (2 ml), N,N-diisopropylethylamine (0.15 ml), potassium iodide (2 mg) was treated with methanesulphonyl chloride (0.34 ml). After stirring at ambient temperature for 40 h. The solvent was evaporated under reduced pressure to leave a beige gum. This was used directly in the next step.

vi) cis-2-[4-(3-Cyanobenzenesulphonyl)-3,5-dimethylpiperazin-1-yl]-N-(2-methyl-5-(4-amino-1-piperidinyl)methyl)phenyl]acetamide The crude product from step (v) (0.2 g) was treated with 1,1-dimethylethyl, 4-aminopiperidinyl-4-carboxylate (0.13 g) in tetrahydrofuran (2 ml) at 55° C. for 24 h. The solvent was evaporated under reduced pressure. The residue was then treated with 4M hydrogen chloride in 1,4-dioxane (3 ml) for 5 h. The solvents were then evaporated under reduced pressure. Purification was by reverse phase HPLC to give the title compound as a white solid. Yield. 0.1 g MS: APCI(+ve) 539 (M+1)

$^1$H NMR δ (DMSO) 9.84(bs, 1H), 9.19(s, 1H), 8.33(s, 1H), 8.16(m, 4H), 7.82(t, 1H), 7.76(s, 1H), 7.32(d, 1H), 7.19(d, 1H), 4.22(s, 2H), 4.11(m, 2H), 3.41(d, 2H), 3.25(bs, 2H), 3.10(s, 2H), 3.01(m, 2H), 2.70(d, 2H), 2.40(m, 2H), 2.34(s, 3H), 2.08(d, 2H), 1.96(dd, 2H), 1.75(q, 2H), 1.45(d, 6H)

EXAMPLE 98

(R)-2-[4-(4-Methanesulphonylbenzenesulphonyl)-3-methylpiperazin-1-yl]-N-(quinolin-5-yl)acetamide

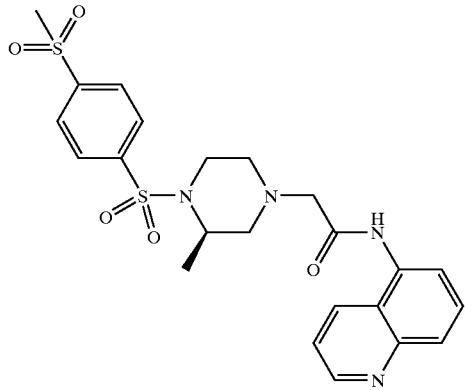

i) (R)-1,1-Dimethylethyl, (4-Methanesulphonylbenzenesulphonyl-3-methylpiperazin-1-yl-1-carboxylate The subtitle compound was prepared from (R)-1,1-dimethylethyl, 3-methylpiperazin-1-yl-1-carboxylate (0.75 g) (J. Med. Chem, 1993, 36 (6), 690)and 4-methanesulphonyl-benzenesulphonyl chloride (0.96 g) by the method of Example 58 step (ii) as white solid. Yield: 0.9 g $^1$H NMR δ (DMSO) 8.15(d, 2H), 8.07(d, 2H), 4.08(bs, 1H), 3.85(bs, 1H), 3.65(bs, 1H), 3.33(s, 2H), 3.32(s, 3H), 3.09(t, 1H), 1.36(s, 9H), 0.93(d, 3H)

ii) (R)-1-(4-Methanesulphonylbenzenesulphonyl-3-methylpiperazine, hydrochloride salt The subtitle compound was prepared from the product of step (i) (0.209 g) by the method of Example 27 step (iv) as a white solid. Yield: 0.15 g MS: APCI(+ve) 319 (M+1)

iii) (R)-2-[4-(4-Methanesulphonylbenzenesulphonyl)-3-methylpiperazin-1-yl]-N-(quinolin-5-yl)acetamide The title compound was prepared from the product of step (ii) (0.14 g) and 2-chloro-N-(quinolin-5-yl)acetamide (0.97 g) (J Indian Chem Soc, 1940, 17, 619–621) by the method of Example 33 step (iv) as a white solid. Yield: 0.135 g MS: APCI(+ve) 503 (M+1)

$^1$H NMR δ (DMSO) 9.88(s, 1H), 8.91(d, 1H), 8.32(d, 1H), 8.16(d, 2H), 8.09(d, 2H), 7.88(dd, 1H), 7.73(m, 2H), 7.55(q, 1H), 4.09(d, 1H), 3.66(d, 1H), 3.38(d, 1H), 3.31(s, 3H), 3.22(s, 2H), 2.91(d, 1H), 2.73(d, 1H), 2.31(m, 2H), 2.15(t, 1H), 1.21(d, 3H)

EXAMPLE 99

(R)-2-[4-(4-Acetamidobenzenesulphonyl)-3-methylpiperazin-1-yl]-N-(quinolin-5-yl)acetamide

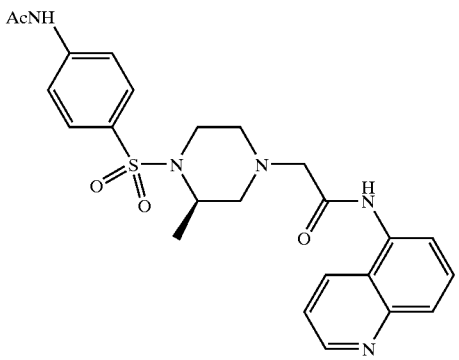

i) (R)-1,1-Dimethylethyl, (4-Acetamidobenzenesulphonyl-3-methylpiperazin-1-yl-1-carboxylate The subtitle compound was prepared from (R)-1,1-dimethylethyl, 3-methylpiperazin-1-yl-1-carboxylate (4 g) (J. Med. Chem, 1993, 36(6), 690) and 4-acetamidobenzenesulphonyl chloride (4.68 g) by the method of Example 58 step (ii) as white solid. Yield: 4.9 g MS: APCI(+ve) 398 (M+1)

ii) (R)-1-(4-Acetamidobenzenesulphonyl)-3-methylpiperazine, hydrochloride salt

The subtitle compound was prepared from the product of step (i) (4.9 g) by the method of Example 27 step (iv) as a white solid. Yield: 4.38 g $^1$H NMR δ (DMSO) 10.60(s, 1H), 8.92(bs, 1H), 8.91(d, 2H), 8.04(t, 1H), 7.85(d, 2H), 7.78(d, 2H), 7.45(d, 1H), 6.66(d, 1H), 3.27(t, 2H), 3.06(m, 2H), 2.87(m, 2H), 2.73(m, 3H), 2.10(s, 3H), 1.30(d, 2H), 1.16(d, 3H)

iii) (R)-2-[4-(4-Acetylaminobenzenesulphonyl)-3-methylpiperazin-1-yl]-N-(quinolin-5-yl)acetamide The title compound was prepared from the product of step (ii) (0.65 g) and 2-chloro-N-(quinolin-5-yl)acetamide (0.39 g) (J Indian Chem Soc, 1940, 17, 619–621) by the method of Example 33 step (iv) as a white solid. Yield: 0.064 g MS: APCI(+ve) 439 (M−42(+H, −Ac))

$^1$H NMR δ (DMSO) 9.89(s, 1H), 8.91(s, 1H), 8.31(d, 1H), 7.87(m, 1H), 7.75(s, 2H), 7.50(m, 1H), 7.43(d, 2H), 6.63(d, 2H), 6.01(s, 2H), 3.90(s, 1H), 3.42(d, 1H), 3.42(d, 1H), 3.24(s, 1H), 3.20(d, 2H), 2.86(d, 1H), 2.68(d, 1H), 2.31(d, 1H), 2.18(t, 1H), 1.18(d, 3H)

EXAMPLE 100 cis-2-[4-(3-Cyanobenzenesulphonyl)-3,5-dimethylpiperazin-1-yl]-N-(2-methyl-5-(1-piperazinylmethyl)phenyl)acetamide

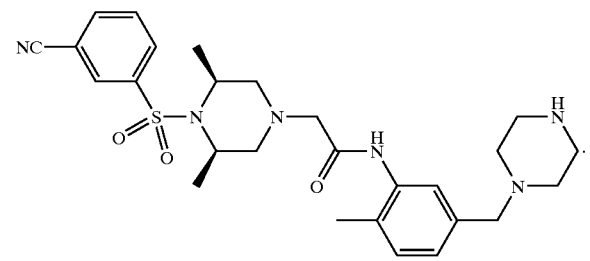

The title compound was prepared from the product of Example 97 step (v) (0.2 g) and 1,1-dimethylethyl, piperazine-1-carboxylate (0.12 g) by the method of Example 97 step (vi) to give the title compound as a white solid. Yield: 74 mg MS: APCI(+ve) 525 (M+1)

$^1$H NMR δ (DMSO) 9.21(s, 1H), 9.0(bs, 2H), 8.33(s, 1H), 8.17(d, 2H), 7.82(t, 1H), 7.69(s, 1H), 7.28(d, 1H), 7.16(d, 1H), 4.14(m, 2H), 3.27(bs, 4H), 3.15(s, 2H), 3.05(bs, 2H), 2.69(d, 2H), 2.21(s, 3H), 2.0(d, 2H), 1.44(d, 6H)

EXAMPLE 101 cis-2-[4-(3-Cyanobenzenesulphonyl)-3,5-dimethylpiperazin-1-yl]-N-(2-methyl-5-(4-piperidinylamino)methyl)phenyl)acetamide

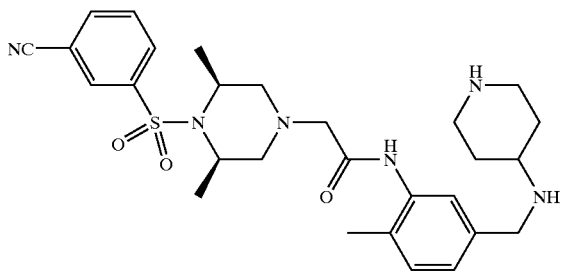

The title compound was prepared from the product of Example 97 step (v) (0.2 g) and 1,1-dimethylethyl, 4-aminopiperidinyl-1-carboxylate (0.12 g) by the method of Example 97 step (vi) as a white solid. Yield: 34 mg MS: APCI(+ve) 539 (M+1)

$^1$H NMR δ (DMSO) 9.18(s, 1H), 9.09(s, 2H), 8.81(m, 1H), 8.60(m, 1H), 8.33(s, 1H), 8.15(d, 2H), 7.82(t, 1H), 7.75(s, 1H), 7.30(d, 1H), 7.21(d, 1H), 4.10(m, 4H), 3.40(d, 2H), 3.32(s, 2H), 2.92(q, 2H), 2.68(d, 2H), 2.23(s, 3H), 1.94(dd, 2H), 1.73(q, 2H), 1.43(d, 6H)

EXAMPLE 102 cis-2-[4-(3-Cyanobenzenesuphonyl)-3,5-dimethylpiperazin-1-yl]-N-(2-methyl-5-(1-morpholinyl)methyl)phenyl)acetamide

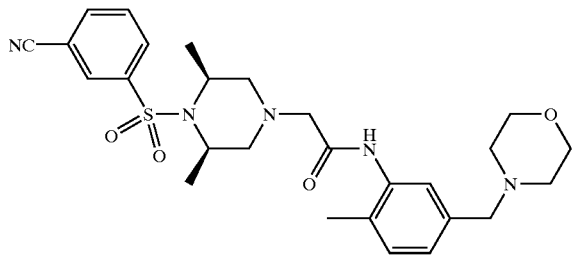

The title compound was prepared from the product of Example 97 step (v) (0.2 g) and morpholine (0.058 g) by the method of Example 97 step (vi). The solvents evaporated under reduced pressure and the residue purified by reverse phase HPLC to give the title compound as a white solid. Yield: 97 mg MS: APCI(+ve) 526 (M+1)

$^1$H NMR δ (DMSO) 10.11(bs, 1H), 9.22(s, 1H), 8.34(s, 1H), 8.16(d, 2H), 7.83(d, 1H), 7.78(d, 1H), 7.33(d, 1H), 7.21(d, 1H), 4.31(s, 2H), 4.12(t, 4H), 3.63(m, 2H), 3.3(m, 4H), 2.70(d, 2H), 2.23(s, 3H), 1.97(dd, 2H), 1.43(d, 6H)

EXAMPLE 103 cis-2-[4-(3-Cyanobenzenesulphonyl)-3,5-dimethylpiperazin-1-yl]-N-(2-methyl-5-(2-hydroxyethylamino)methyl)phenyl)acetamide

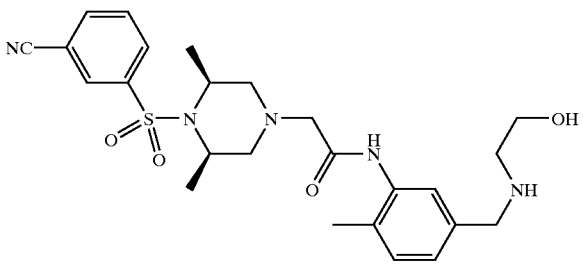

The title compound was prepared from the product of Example 97 step (v) (0.2 g) and ethanolamine (0.041 g) by the method of Example 97 step (vi). The solvents evaporated under reduced pressure and the residue purified by reverse phase HPLC to give the title compound as a white solid. Yield: 37 mg MS: APCI(+ve) 500 (M+1)

$^1$HNMR δ (DMSO) 8.27(s, 1H), 8.18(d, 1H), 8.02(d, 1H), 7.74–7.82(m, 3H), 7.35(d, 2H), 7.25(d, 1H), 4.27(t, 2H), 4.20(s, 2H), 3.83(t, 2H), 3.40(s, 2H), 3.25(s, 1H), 3.14(t, 2H), 2.97(d, 2H), 2.33(s, 5H), 1.56(d, 6H)

EXAMPLE 104 cis-2-[4-(3-Cyanobenzenesulphonyl)-3,5-dimethylpiperazin-1-yl]-N-(2-methyl-5-(S,S)-(2,5-diazabicyclo[2.2.1]hept-2-yl)methyl)phenyl)acetamide

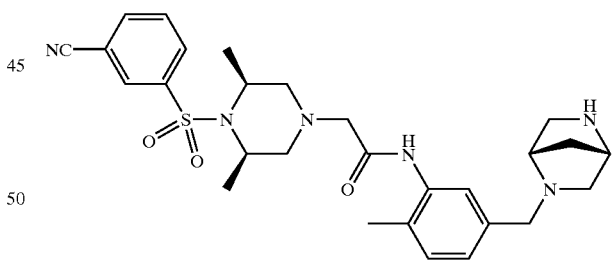

The title compound was prepared from the product of Example 97 step (v) (0.2 g) and 1,1-dimethylethyl, (S,S)-2,5-diazabicyclo[2.2.1]heptane-5-carboxylate (0.13 g) by the method of Example 97 step (vi) as a white solid. Yield: 107 mg MS: APCI(+ve) 537 (M+1)

$^1$H NMR δ (DMSO) 9.2(s, 1H), 8.34(s, 1H), 8.16(d, 2H), 7.83(d, 1H), 7.79(s, 1H), 7.31(d, 1H), 7.24(d, 1H), 4.46(s, 1H), 4.32(m, 2H), 4.12(s, 2H), 3.35(d, 2H), 3.11(s, 2H), 2.68(d, 2H), 2.23(s, 3H), 1.98(t, 3H), 1.44(d, 6H)

EXAMPLE 105

(R)-2-[4-(2-Pyridinesulphonyl)-3-methylpiperazin-1-yl]-N-(quinolin-5-yl)acetamide

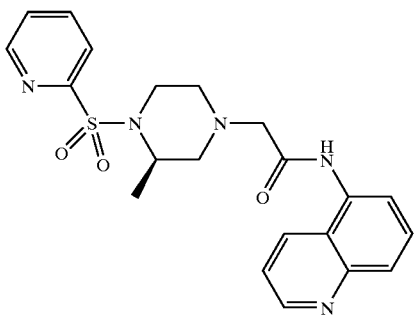

i) (R)-1,1-Dimethylethyl, (2-Pyridinesulphonyl-3-methylpiperazin-1-yl-1-carboxylate A solution of 1,1-dimethylethyl, 3-(R)-methylpiperazine-1-carboxylate (2 g) (J. Med. Chem, 1993, 36(6), 690), 4-N,N'-dimethylaminopyridine (1.22 g) in pyridine (10 ml) was treated with 2-pyridinesulphonyl chloride (2.7 g) at 0° C. The ice bath was removed and the mixture further stirred for 1 h at ambient temperature. The mixture was partitioned between dichloromethane and water. The organic phase further washed with brine, collected, dried (MgSO$_4$) and solvent evaporated under reduced pressure. Purification was by silica gel chromatography eluting with ethyl acetate/dichloromethane mixtures to give the subtitle compound as white solid. Yield: 3.3 g MS: ESI(+ve) 342 (M+1)

ii) (R)-1-(2-Pyridinesulphonyl-3-methylpiperazine, hydrochloride salt

The subtitle compound was prepared from the product of step (i) (2.5 g) by the method of Example 27 step (iv) as a white solid. Yield: 2.5 g MS: ESI(+ve) 242 (M+1)

iii) (R)-2-[4-(2-Pyridinesulphonyl)-3-methylpiperazin-1-yl]-N-(quinolin-5-yl)acetamide The title compound was prepared from the product of step (ii) (0.6 g) and 2-chloro-N-(quinolin-5-yl)acetamide (0.39 g) (J Indian Chem Soc, 1940, 17, 619–621) by the method of Example 80 step (iii). Purification was by silica gel chromatography eluting with ethyl acetate to give a white solid. Yield: 0.41 g MS: ESI(+ve) 424 (M+1)

$^1$H NMR δ (DMSO) 8.8(d, 1H), 8.35(d, 1H), 8.10(t, 1H), 7.97(d, 1H), 7.90(d, 1H), 7.7(m, 3H), 7.55(m, 1H), 4.10(m, 1H), 3.7(m, 1H) 3.5(t, 1H), 3.3(m, 2H), 3.2(m, 1H), 2.95(d, 1H), 2.7(d, 1H), 2.4–2.1(m, 2H), 1.2(d, 3H)

EXAMPLE 106 cis-2-[4-(3-Cyanobenzenesulphonyl)-3,5-dimethylpiperazin-1-yl]-N-(2-methyl-3-(4-amino-1-piperidinyl)methyl)phenyl]acetamide

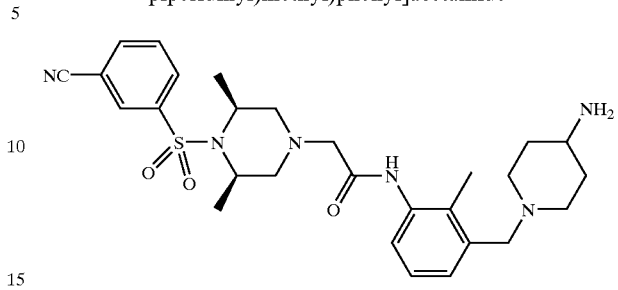

i) 2-Methyl-3-((1,1-dimethyl)-1-dimethylethyl)silyloxymethylaniline

The subtitle compound was prepared from 2-methyl-3-hydoxymethylaniline (5 g) and tert-butyldimethylsilyl chloride (5.42 g) by the method of Example 97 step (i) as an oil which crystalised on standing. Yield: 9.12 g MS: APCI(+ve) 252 (M+1)

ii) 2-Chloro-N-(2-methyl-3-((1,1-dimethyl)-1-dimethylethyl)silyloxymethyl)acetamide The subtitle compound was prepared from the product of step (i) (4.13 g) and chloroacetyl chloride (1.5 ml) by the method of Example 33 step (iii) as a beige solid. Yield: 3.12 g MS: APCI(+ve) 328 (M+1)

iii) cis-2-[4-(3-Cyanobenzenesulphonyl)-3,5-dimethylpiperazin-1-yl]-N-(2-methyl-5-((1,1-dimethyl)-1-dimethylethyl)silyloxymethyl)phenyl]acetamide The subtitle compound was prepared from the product of step (ii) (1.25 g) and the product of Example 80 step (ii) (1 g) by the method of Example 80 step (iii) as a cream solid. Yield: 1.5 g MS: APCI(+ve) 571 (M+1)

iv) cis-2-[4-(3-Cyanobenzenesulphonyl)-3,5-dimethylpiperazin-1-yl]-N-(2-methyl-5-hydroxymethyl)phenyl]acetamide The subtitle compound was prepared from the product of step (iii) (1.4 g) and 1M tetrabutylammonium fluoride in tetrahydrofuran (2.7 ml) by the method of Example 97 step (iv) as a white solid. Yield: 1 g MS: APCI(+ve) 457 (M+1)

v) cis-2-[4-(3-Cyanobenzenesulphonyl)-3,5-dimethylpiperazin-1-yl]-N-(2-methyl-3-iodomethyl)phenyl]acetamide The product from step (iv) (0.1 g) in tetrahydrofuran (2 ml), N,N-diisopropylethylamine (0.15 ml), potassium iodide (2 mg) was treated with methanesulphonyl chloride (0.34 ml). After stirring at ambient temperature for 40 h. The solvent was evaporated under reduced pressure to leave a beige gum. This was used directly in the next step.

vi) cis-2-[4-(3-Cyanobenzenesulphonyl)-3,5-dimethylpiperazin-1-yl]-N-(2-methyl-5-(4-amino-1-piperidinyl)methyl)phenyl]acetamide The crude product from step (v) (0.2 g) was treated with 1,1-dimethylethyl, 4-aminopiperidinyl-4-carboxylate (0.13 g) in tetrahydrofuran (2 ml) at 55° C. for 24 h. The solvent was evaporated under reduced pressure. The residue was then treated with 4M hydrogen chloride in 1,4-dioxane (3 ml) for 5 h. The solvents were then evaporated under reduced pressure. Purification was by reverse phase HPLC to give the title compound as a white solid. Yield. 0.068 g MS: APCI(+ve) 539 (M+1)

¹H NMR δ (CDCl₃/DMSO) 8.87(bs, 1H), 8.67(bs, 1H), 8.14(s, 1H), 8.10(d, 1H), 7.95(d, 1H), 7.80(d, 1H), 7.75(t, 1H), 7.30(m, 2H), 4.30(bs, 1H), 4.20(m, 2H), 3.10(s, 2H), 2.80(d, 2H), 2.30(s, 3H), 2.20(m, 4H), 1.60(d, 6H)

EXAMPLE 107 cis-2-[4-(3-Cyanobenzenesulphonyl)-3,5-dimethylpiperazin-1-yl]-N-(2-methyl-3-(4-piperidinylamino)methyl)phenyl)acetamide

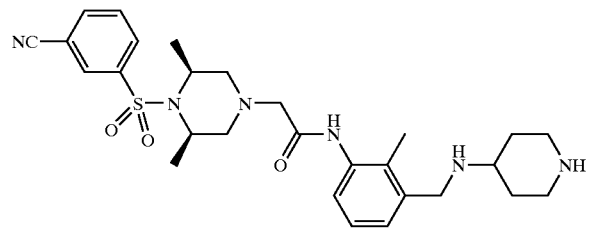

The title compound was prepared from the product of Example 106 step (v) (0.2 g) and 1,1-dimethylethyl, 4-aminopiperidinyl-1-carboxylate (0.12 g) by the method of Example 106 step (vi) as a white solid. Yield: 38 mg MS: APCI(+ve) 539 (M+1)

¹H NMR δ (DMSO) 9.33(bs, 1H), 9.10(bs, 1H), 8.8(bd, 1H), 8.60(bd, 1H), 8.37(s, 1H), 8.20(m, 1H), 7.90(t, 1H), 7.40(d, 1H), 7.30(m, 2H), 4.20(bs, 2H), 4.10(m, 2H), 3.10(s, 2H), 3.00(m, 2H), 2.7(m, 2H), 2.30(m, 2H), 2.20(s, 3H), 2.00–1.80(m, 4H), 1.40(s, 6H)

EXAMPLE 108 cis-2-[4-(3-Cyanobenzenesulphonyl)-3,5-dimethylpiperazin-1-yl]-N-(2-methyl-3-(1-piperazinylmethyl)phenyl)acetamide

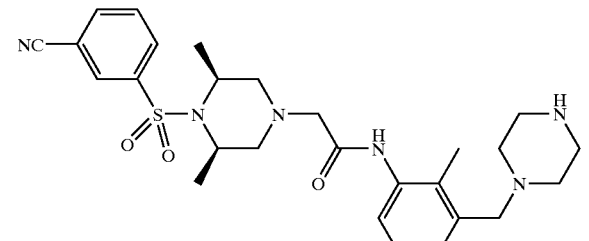

The title compound was prepared from the product of Example 106 step (v) (0.2 g) and 1,1-dimethylethyl, piperazine-1-carboxylate (0.12 g) by the method of Example 106 step (vi) as a white solid. Yield: 74 mg MS: APCI(+ve) 525 (M+1)

¹H NMR δ (DMSO) 8.34(s, 1H), 8.20(m, 2H), 7.80(t, 1H), 7.40(t, 1H), 7.20(2×d, 2H), 4.20(m, 2H), 3.90(bs, 2H), 3.20(m, 6H), 3.00–2.60(m, 6H), 2.20(s, 3H), 2.00(m, 2H), 1.50(d, 6H)

EXAMPLE 109 cis-2-[4-(3-Cyanobenzenesulphonyl)-3,5-dimethylpiperazin-1-yl]-N-(2-methyl-3 -(S,S)-(2,5-diazabicyclo[2.2.1]hept-2-yl)methyl)phenyl) acetamide

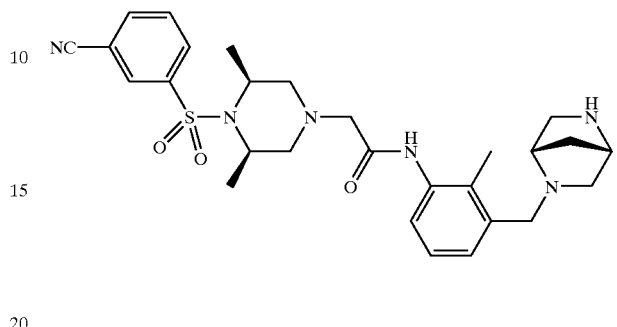

The title compound was prepared from the product of Example 106 step (v) (0.2 g) and 1,1-dimethylethyl, (S,S)-2,5-diazabicyclo[2.2.1]heptane-5-carboxylate (0.13 g) by the method of Example 106 step (vi) as a white solid. Yield: 82 mg MS: APCI(+ve) 537 (M+1)

¹H NMR δ (DMSO) 8.38(s, 1H), 8.20(m, 2H), 7.80(t, 1H), 7.50(d, 1H), 7.30(m, 2H), 4.40(s, 1H), 4.30(m, 2H), 4.10(m, 2H), 3.30(m, 2H), 3.10(s, 2H), 2.80(m, 2H), 2.22(s, 3H), 2.00(m, 4H), 1.50(d, 6H)

EXAMPLE 110 cis-2-[4-(3-Cyanobenzenesulphonyl)-3,5-dimethylpiperazin-1-yl]-N-((2-methyl-3-(1-morpholinyl)methyl)phenyl)acetamide

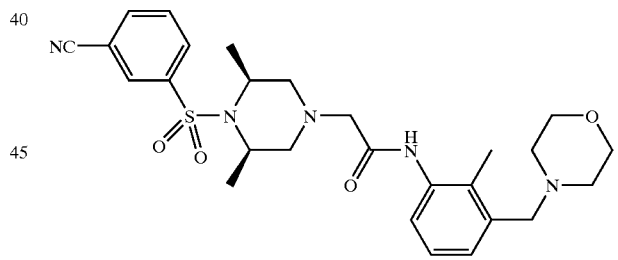

The title compound was prepared from the product of Example 106 step (v) (0.2 g) and morpholine (0.058 g) by the method of Example 106 step (vi) as a white solid. Yield: 69 mg MS: APCI(+ve) 526 (M+1)

¹H NMR δ (DMSO) 8.34(s, 1H), 8.20(m, 2H), 7.80(t, 1H), 7.60(d, 1H), 7.40(m, 2H), 4.40(s, 2H), 4.20(m, 2H), 4.00(bs, 2H), 3.70(bs, 2H), 3.30(bs+s, 6H), 2.80(d, 2H), 2.30(s, 3H), 2.00(m, 2H), 1.50(d, 6H)

EXAMPLE 111

Cis-2-[4-(3-Cyanobenzenesulphonyl)-3,5-dimethylpiperazin-1-yl]-N-((2-methyl-3-(2-(1-pyrrolidinyl)ethoxy)phenyl)acetamide

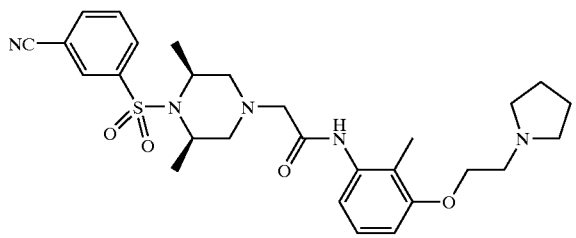

i) 2-Methyl-3-((1,1-dimethyl)-1-dimethylethyl)silyloxyaniline

The subtitle compound was prepared from 3-amino-2-methylphenol (10) and tert-butyldimethylsilyl chloride (12.22 g) by the method of Example 97 step (i) as a brown oil. Yield: 15 g $^1$H NMR δ (CDCl$_3$) 6.86(t, 1H), 6.33(d, 1H), 6.27(d, 1H), 3.58(bs, 2H), 2.04(s, 3H), 1.0l(s, 9H), 0.20(s, 6H)

ii) 2-Chloro-N-(2-methyl-3-((1,1-dimethyl)-1-dimethylethyl)silyloxy)phenyl)acetamide The product from step (i) (5 g), PyBrop (9.82 g), chloroacetic acid (1.99 g), N,N-diisopropylethylamine (11 ml) in dichloromethane (100 ml) were stirred at ambient temperature for 16 h. The mixture was partitioned between water and dichloromethane, the organic phase collected, dried (MgSO$_4$) and solvent evaporated under reduced pressure. Purification was by silica gel chromatography eluting with 10% diethyl ether in iso-hexane containing 1% triethylamine to give the subtitle compound as a pale yellow oil. Yield: 3.5 g $^1$H NMR δ (CDCl$_3$) 8.21(bs, 1H), 7.48(d, 1H), 7.09(t, 1H), 6.68(d, 1H), 4.23(s, 2H), 2.16(s, 3H), 1.02(s, 9H), 0.22(s, 6H)

iii) Cis-2-[4-(3-Cyanobenzenesulphonyl)-3,5-dimethylpiperazin-1-yl]-N-((2-methyl-3-((1,1-dimethyl)-1-dimethylethyl)silyloxy)phenyl)acetamide The subtitle compound was prepared from the product of step (ii) (1 g) and the product of Example 80 step (ii) (0.89 g) by the method of Example 80 step (iii) as a beige solid. Yield: 1.6 g $^1$H NMR δ (CDCl$_3$) 8.67(s, 1H), 8.12(s, 1H), 8.03(d, 1H), 7.85(d, 1H), 7.67(t, 1H), 7.59(d, 1H), 7.07(t, 1H), 6.64(d, 1H), 4.05–4.10(m, 2H), 3.10(s, 2H), 2.73(d, 2H), 2.19(d, 2H), 2.10(s, 3H), 1.54(s, 6H), 1.01(s, 9H), 0.22(s, 6H)

iv) Cis-2-[4-(3-Cyanobenzenesulphonyl)-3,5-dimethylpiperazin-1-yl]-N-((2-methyl-3-hydroxy)phenyl)acetamide The subtitle compound was prepared from the product of step (iii) (1.6 g) and tetra-butylammonium fluoride (3.18 ml) by the method of Example 97 step (iv) as a white solid Yield: 0.5 g MS APCI(+ve) 443 (M+1)

v) Cis-2-[4-(3-Cyanobenzenesulphonyl)-3,5-dimethylpiperazin-1-yl]-N-((2-methyl-3-(2-(1-pyrrolidinyl)ethoxy)phenyl)acetamide The product from step (iv) (0.1 g), 1-(2-chloroethyl)pyrrolidine hydrochloride (76 mg), ceasium carbonate (0.36 g) in 1-methyl-2-pyrrolidinone (2 ml) were stirred at 70° C. for 16 h. The mixture was partitioned between ethyl acetate and water, the organic phase collected, dried (MgSO$_4$) and solvent evaporated under reduced pressure. Purification was by reverse phase HPLC eluting with 5 to 90% methanol in 0.1% aqueous trifluoroacetic acid to give the the title compound as a white solid. Yield: 7 mg MS: APCI(+ve) 540 (M+1)

$^1$H NMR δ (CD$_3$OD) 8.15(s, 1H), 8.05(d, 1H), 7.89(d, 1H), 7.67(t, 1H), 7.06(s, 1H), 7.04(s, 1H), 6.74(t, 1H), 4.01–4.09(m, 4H), 2.99(s, 2H), 2.88(t, 2H), 2.61–2.66(m, 6H), 2.05(s, 3H), 1.95(dd, 2H), 1.71–1.77(m, 4H), 1.44(d, 6H)

EXAMPLE 112

(±) Cis-2-[4-(3-Cyanobenzenesulphonyl)-3,5-dimethylpiperazin-1-yl]-N-((2-methyl-3-(1-methylpiperidin-3-yl)methoxy)phenyl)acetamide

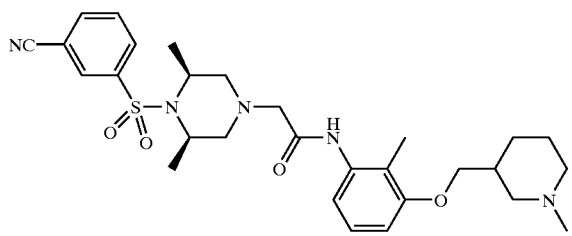

The title compound was prepared from the product of Example 111 step (iv) (0.1 g) and (±) 1-methyl-3-chloromethylpiperidine (83 mg) by the method of Example 111 step (v) as a white solid. Yield: 19 mg MS: APCI(+ve) 554 (M+1)

$^1$H NMR δ (CD$_3$OD) 8.24(s, 1H), 8.14(d, 1H), 7.98(d, 1H), 7.77(t, 1H), 7.10–7.15(m, 2H), 6.78–6.81(m, 1H), 4.12–4.18(m, 2H), 3.80–3.92(m, 2H), 3.09(s, 3H), 2.75–2.85(m, 1H), 2.74(d, 2H), 2.31(s, 3H), 2.12(s, 3H), 1.64–2.17(m, 8H), 1.53(d, 6H), 1.15–1.19(m, 2H)

EXAMPLE 113

Cis-2-[4-(3-Cyanobenzenesulphonyl)-3,5-dimethylpiperazin-1-yl]-N-((2-methyl-4-(2-(1-pyrrolidinyl)ethoxy)phenyl)acetamide

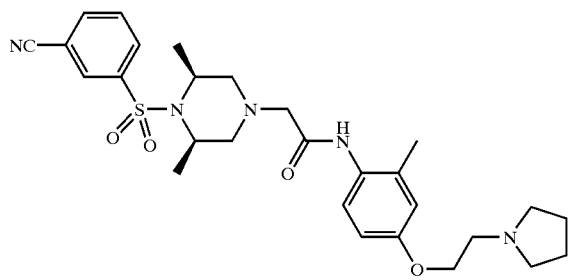

i) 2-Methyl-4-((1,1-dimethyl)-1-dimethylethyl)silyloxyaniline

The subtitle compound was prepared from 4-amino-3-methylphenol (10 g) and tert-butyldimethylsilyl chloride (12.22 g) by the method of Example 97 step (i) as a brown oil. Yield: 14 g $^1$H NMR δ (CDCl$_3$) 6.53–6.58(m, 3H), 3.33(bs, 2H), 2.12(s, 3H), 0.98(s, 9H), 0.15(s, 6H)

ii) 2-Chloro-N-(2-methyl-3-((1,1-dimethyl)-1-dimethylethyl)silyloxy)phenyl)acetamide The subtitle compound was prepared from the product of step (i) (5 g) by the method of Example 111 step (ii) as pale yellow oil. Yield: 5 g $^1$H NMR δ (CDCl$_3$) 8.06(bs, 1H), 7.57–7.60(m, 1H), 6.53–6.58(m, 3H), 3.33(bs, 2H), 2.12(s, 3H), 0.98(s, 9H), 0.15(s, 6H)

iii) Cis-2-[4-(3-Cyanobenzenesulphonyl)-3,5-dimethylpiperazin-1-yl]-N-((2-methyl-4-((1,1-dimethyl)-1-dimethylethyl)silyloxy)phenyl)phenyl)acetamide The subitle compound was prepared from the product of step (ii) (1 g) and the product of Example 80 step (ii) (0.89 g) by the method of Example 80 step (iii) as a white solid. Yield: 1.6 g $^1$H NMR δ (CDCl$_3$) 8.48(s, 1H), 8.12(s, 1H), 8.04(d, 1H), 7.86(d, 1H), 7.64–7.70(m, 2H), 6.67–6.70(m, 2H), 4.114.15 (m, 2H), 3.08(s, 2H), 2.73(d, 2H), 2.22(s, 3H), 2.16(dd, 2H), 1.55(d, 6H), 0.97(s, 9H), 0.18(s, 6H)

iv) Cis-2-[4-(3-Cyanobenzenesulphonyl)-3,5-dimethylpiperazin-1-yl]-N-((2-methyl-4-hydroxy)phenyl) acetamide The subtitle compound was prepared from the product of step (iii) (1.6 g) and tetrabutylammonium fluoride (3.21 ml) by the method of Example 97 step (iv) as a white solid Yield: 0.4 g MS APCI(+ve) 443 (M+1)

v) Cis-2-[4-(3-Cyanobenzenesulphonyl)-3,5-dimethylpiperazin-1-yl]-N-((2-methyl-4-(2-(1-pyrrolidinyl) ethoxy)phenyl)acetamide The title compound was prepared from the product of step (iv) (0.1 g) and 1-(2-chloroethyl)pyrrolidine hydrochloride (76 mg) by the method of Example 111 step (v) as a white solid. Yield: 10 mg MS: APCI(+ve) 540 (M+1)

$^1$H NMR δ (CD$_3$OD) 8.24(s, 1H), 8.15(d, 1H), 7.98(d, 1H), 7.77(t, 1H), 7.30(d, 1H), 6.83(d, 1H), 6.77(dd, 1H), 4.13–4.18(m, 2H), 4.10(t, 2H), 3.07(s, 2H), 2.91(t, 2H), 2.73(d, 2H), 2.65–2.69(m, 4H), 2.25(s, 3H), 2.04(dd, 2H), 1.79–1.86(m, 4H), 1.53–1.54(d, 6H),

EXAMPLE 114

(±) Cis-2-[4-(3-Cyanobenzenesulphonyl)-3,5-dimethylpiperazin-1-yl]-N-((2-methyl-4-(1-methylpiperidin-3-yl)methoxy)phenyl)acetamide

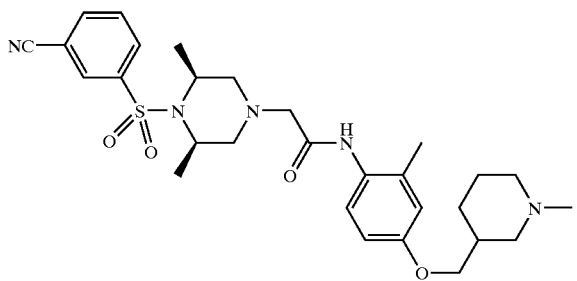

The title compound was prepared from the product of Example 113 step (iv) (0.1 g) and (±) 1-methyl-3-chloromethylpiperidine (83 mg) by the method of Example 111 step (v) as a white solid. Yield: 19 mg MS: APCI(+ve) 554 (M+1)

$^1$H NMR δ (CD$_3$OD) 8.24(s, 1H), 8.15(d, 1H), 7.98(d, 1H), 7.77(t, 1H), 7.29(d, 1H), 6.79(d, 1H), 6.74(dd, 1H), 4.13–4.16(m, 2H), 3.75–3.88(m, 2H), 3.08(s, 2H), 3.02–3.04(m, 1H), 2.82–2.85(m, 1H), 2.73(d, 2H), 2.29(s, 3H), 2.21(s, 3H), 1.62–2.10(m, 8H), 1.53(d, 6H), 1.09–1.13 (m, 1H),

EXAMPLE 115

(±) Cis-2-[4-(3-Cyanobenzenesulphonyl)-3,5-dimethylpiperazin-1-yl]-N-((2-methyl-5-(1-methylpiperidin-3-yl)methoxy)phenyl)acetamide

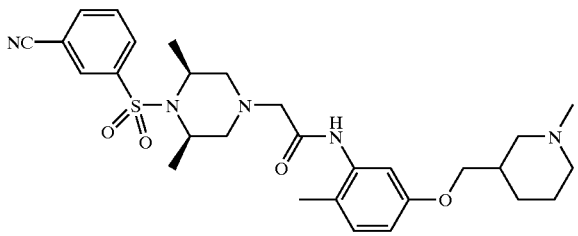

i) 2-Methyl-5-((1,1-dimethyl)-1-dimethylethyl) silyloxyaniline

The subtitle compound was prepared from 3-amino-4-methylphenol (10 g) and tert-butyldimethylsilyl chloride (12.22 g) by the method of Example 97 step (i) as a brown oil. Yield: 15 g $^1$H NMR δ (CDCl$_3$) 6.84–6.88(m, 1H), 6.18–6.22(m, 2H), 3.52(bs, 2H), 2.08(s, 3H), 0.97(s, 9H), 0.17(s, 6H)

ii) 2-Chloro-N-(2-methyl-5-((1,1-dimethyl)-1-dimethylethyl)silyloxy)phenyl)acetamide The subtitle compound was prepared from the product of step (i) (5 g) by the method of Example 111 step (ii) as pale yellow oil. Yield: 5.3 g $^1$H NMR δ (CDCl$_3$) 8.19(bs, 1H), 7.57(d, 1H), 7.03(d, 1H), 6.61(dd, 1H), 4.22(s, 2H), 2.23(s, 3H), 0.98(s, 9H), 0.21(s, 6H)

iii) Cis-2-[4-(3-Cyanobenzenesulphonyl)-3,5-dimethylpiperazin-1-yl]-N-((2-methyl-5-((1,1-dimethyl)-1-dimethylethyl)silyloxy)phenyl)phenyl)acetamide The subtitle compound was prepared from the product of step (ii) (1 g) and the product of Example 80 step (ii) (0.89 g) by the method of Example 80 step (iii) as a white solid. Yield: 1.8 g $^1$H NMR δ (CDCl$_3$) 8.64(s, 1H), 8.12(s, 1H), 8.04(d, 1H), 7.87(d, 1H), 7.68–7.70(m, 2H), 7.01(d, 1H), 6.56(dd, 1H), 4.09–4.16(m, 2H), 3.08(s, 2H), 2.72(d, 2H), 2.22(s, 3H), 2.16(dd, 2H), 1.55(d, 6H), 0.97(s, 9H), 0.19(s, 6H)

iv) Cis-2-[4-(3-Cyanobenzenesulphonyl)-3,5-dimethylpiperazin-1-yl]-N-((2-methyl-5-hydroxy)phenyl) acetamide The subtitle compound was prepared from the product of step (iii) (1.81 g) and tetra-butylammonium fluoride (3.24 ml) by the method of Example 97 step (iv) as a white solid Yield: 0.8 g MS APCI(+ve) 443 (M+1)

v) (±) Cis-2-[4-(3-Cyanobenzenesulphonyl)-3,5-dimethylpiperazin-1-yl]-N-((2-methyl-5-(1-methylpiperidin-3-yl)methoxy)phenyl)acetamide The title compound was prepared from the product of step (iv) (0.1 g) and (±) 1-methyl-3-chloromethylpiperidine (76 mg) by the method of Example 111 step (v) as a white solid. Yield: 5 mg MS: APCI(+ve) 540 (M+1)

$^1$H NMR δ (CD$_3$OD) 8.24(s, 1H), 8.14(d, 1H), 7.98(d, 1H), 7.77(t, 1H), 7.32(d, 1H), 7.10(d, 1H), 6.67(dd, 1H), 4.12–4.18(m, 2H), 3.73–3.86(m, 2H), 3.09(s, 2H), 3.02–3.05(m, 1E), 2.83–2.86(m, 1H), 2.74(d, 2H), 2.29(s, 3H), 2.24(s, 3H), 1.58–2.11(m, 9H), 1.54(d, 6H), 1.09–1.13 (m, 1H),

EXAMPLE 116

(±) Cis-2-[4-(3-Cyanobenzenesulphonyl)-3,5-dimethylpiperazin-1-yl]-N-((2-methyl-6-(1-methylpiperidin-3-yl)methoxy)phenyl)acetamide

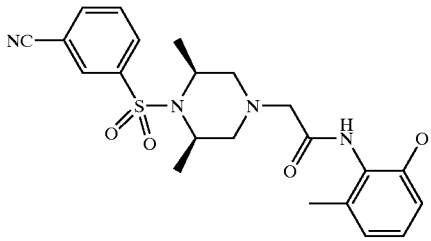

i) 2-Methyl-6-((1,1-dimethyl)-1-dimethylethyl)silyloxyaniline

The subtitle compound was prepared from 2-amino-3-methylphenol (10) and tert-butyldimethylsilyl chloride (12.22 g) by the method of Example 97 step (i) as a brown oil. Yield: 14 g $^1$H NMR δ (CDCl$_3$) 6.53–6.70(m, 3H), 3.66(bs, 2H), 2.17(s, 3H), 1.02(s, 9H), 0.24(s, 6H)

ii) 2-Chloro-N-(2-methyl-6-((1,1-dimethyl)-1-dimethylethyl)silyloxy)phenyl)acetamide The subtitle compound was prepared from the product of step (i) (5 g) by the method of Example 111 step (ii) as pale yellow oil. Yield: 4.6 g $^1$H NMR δ (CDCl$_3$) 7.97(bs, 1H), 7.07(t, 1H), 6.86(d, 1H), 6.72(d, 1H), 4.22(s, 2H), 2.23(s, 3H), 1.00(s, 9H), 0.22(s, 6H)

iii) Cis-2-[4-(3-Cyanobenzenesulphonyl)-3,5-dimethylpiperazin-1-yl]-N-((2-methyl-6-((1,1-dimethyl)-1-dimethylethyl)silyloxy)phenyl)acetamide The subitle compound was prepared from the product of step (ii) (1 g) and the product of Example 80 step (ii) (0.89 g) by the method of Example 80 step (iii) as a white solid. This product was used directly in the next step iv) Cis-2-[4-(3-Cyanobenzenesulphonyl)-3,5-dimethylpiperazin-1-yl]-N-((2-methyl-6-hydroxy)phenyl)acetamide The subtitle compound was prepared from the product of step (iii) (2 g) and tetra-butylammonium fluoride (3.18 ml) by the method of Example 97 step (iv) as a white solid Yield: 0.8 g MS APCI(+ve) 441 (M−1)

v) (±) Cis-2-[4-(3-Cyanobenzenesulphonyl)-3,5-dimethylpiperazin-1-yl]-N-((2-methyl-6-(1-methylpiperidin-3-yl)methoxy)phenyl)acetamide The title compound was prepared from the product of step (iv) (0.1 g) and (±) 1-methyl-3-chloromethylpiperidine (76 mg) by the method of Example 111 step (v) as a white solid. Yield: 26 mg MS: APCI(+ve) 540 (M+1)

$^1$H NMR δ (CD$_3$OD) 8.29(s, 1H), 8.17(d, 1H), 7.98(d, 1H), 7.78(t, 1H), 7.17(t, 1H), 6.87(s, 1H), 6.84(s, 1H), 4.19–4.20(m, 2H), 3.83–3.88(m, 2H), 3.12(s, 2H), 2.80–3.0 (m, 3H), 2.28(s, 3H), 2.20(s, 3H), 1.6–2.1(m, 9H), 1.55(d, 6H), 1.0–1.2(m, 1H)

EXAMPLE 117

Cis-2-[4-(1-Methylimidazol-4-sulphonyl-4-yl)-3,5-dimethylpiperazin-1-yl]-N-((2-methyl-3-(2-(1-pyrrolidinyl)ethoxy)phenyl)acetamide

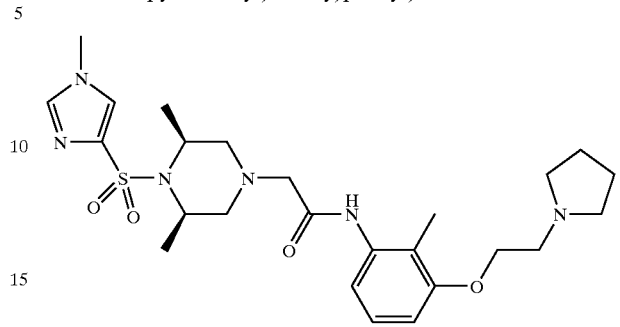

i) Cis-1-(1-Methylimdazol-4-sulphonyl-4-yl)-2,6-dimethyl-4-phenylmethylpiperazine 1-methylimidazol-4-sulphonyl chloride (19.45 g) was added in small portions to a solution of cis-4-benzyl-2,6-dimethylpiperazine (20 g) in pyridine (53 ml) at 120° C. After heating for a further 10 min at reflux the solvent was evaporated under reduced pressure. The mixture was partitioned between dichloromethane and dilute sodium hydroxide solution. The organic phase collected, dried (MgSO$_4$) and solvent evaporated under reduced pressure. Purification was by silica gel chromatography eluting with 0 to 5% methanol in dichloromethane to give the subtitle compound as pale yellow solid. Yield: 14.2 g $^1$H NMR δ (CDCl$_3$) 7.22–7.46(m, 7H), 4.07–4.15(m, 2H), 3.73(s, 3H), 3.42(d, 2H), 2.53(d, 2H), 2.08(dd, 2H), 1.46(d, 6H)

ii) Cis-1-(1-Methylimidazol-4-sulphonyl-4-yl)-2,6-dimethylpiperazine

The subtitle compound was prepared from the product of step (i) (14.07 g) by the method of Example 80 step (ii) as tan solid. Yield: 12.16 g MS: APCI (+ve) 259 (M+1)

iii) Cis-2-[4-(1-Methylimdazol-4-sulphonyl-4-yl)-3,5-dimethylpiperazin-1-yl]-N-((2-methyl-3-((1,1-dimethyl)-1-dimethylethyl)silyloxy)phenyl)acetamide The subtitle compound was prepared from the product of step (ii) (0.82 g) and the product of Example 111 step (ii) (1 g) by the method of Example 80 step (iii) as a white solid. Yield: 1.6 g $^1$H NMR δ (CDCl$_3$) 8.83(s, 1H), 7.61(d, 1H), 7.47(s, 1H), 7.40(s, 1H), 7.07(t, 1H), 6.63(d, 1H), 4.21–4.24(m, 2H), 3.75(s, 3H), 3.10(s, 2H), 2.65(d, 2H), 2.17(s, 3H), 1.56(d, 6H), 1.02(s, 9H), 0.22(s, 6H)

iv) Cis-2-[4-(1-Methylimidazol-4-sulphonyl-4-yl)-3,5-dimethylpiperazin-1-yl]-N-((2-methyl-3-hydroxy)phenyl)acetamide The subtitle compound was prepared from the product of step (iii) (1.51 g) by the method of Example 111 step (iv) as a white solid. Yield: 0.4 g MS: APCI(+ve) 422 (M+1)

v) Cis-2-[4-(1-Methylimidazol-4-sulphonyl-4-yl)-3,5-dimethylpiperazin-1-yl]-N-((2-methyl-3-(2-(1-pyrrolidinyl)ethoxy)phenyl)acetamide The title compound was prepared from the product of step (iv) (95 mg) and 1-(2-chloroethyl)pyrrolidine (83 mg) by the method of Example 111 step (v) as a white solid. Yield: 19 mg MS: APCI(+ve) 519 (M+1)

$^1$H NMR δ (CD$_3$OD) 7.76(s, 1H), 7.67(s, 1H), 7.13–7.24 (m, 2H), 6.84(d, 1H), 4.12–4.19(m, 4H), 3.78(s, 3H), 3.11(s, 2H), 3.01(t, 2H), 2.67–2.76(m, 6H), 2.18–2.28(m, 5H), 1.54(d, 6H)

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 $\mu$l of test solution comprising 200 $\mu$l of a suspension of THP-1 cells (2.5×10$^6$ cells/ml) containing 10$^{-4}$M ethidium bromide, 25 $\mu$l of a high potassium buffer solution containing 10$^{-5}$M bbATP, and 25 $\mu$l of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of the Examples demonstrated antagonist activity, having a pIC$_{50}$ figure >5.0.

What is claimed is:

1. A compound of the formula

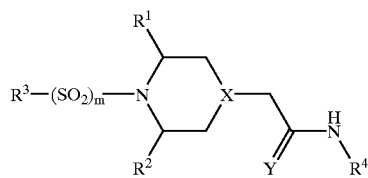

(I)

wherein,

X represents a nitrogen atom or a group C(R$^5$);

Y represents an oxygen or sulphur atom or a group NR$^6$;

either R$^1$ and R$^1$ each independently represent a hydrogen atom or a C$_1$–C$_4$ alkyl group but do not both simultaneously represent a hydrogen atom, or R$^1$ and R$^2$ together represent a group —CH$_2$ZCH$_2$—;

Z represents a bond, an oxygen or sulphur atom or a group CH$_2$ or NR$^7$;

m is 0 or 1;

R$^3$ represents a 5- to 10-membered unsaturated ring system which may comprise from 1 to 4 ring heteroatoms independently selected from nitrogen, oxygen and sulphur, the ring system being optionally substituted by one or more substituents independently selected from halogen, nitro, cyano, NR$^8$R$^9$, C$_1$–C$_4$ alkyl-C(O)NH—, NHR$^{12}$C(O)—, C$_1$–C$_4$ alkyl-SO$_2$—, C$_1$–C$_4$ alkyl-SO$_2$NH—, C$_1$–C$_4$ alkyl-NHSO$_2$—, C$_1$–C$_4$ alkoxy, and C$_1$–C$_4$ alkyl optionally substituted by one or more fluorine atoms;

R$^4$ represents a phenyl or pyridinyl group, each of which is substituted in an ortho position with a substituent selected from halogen, C$_1$–C$_4$ alkoxy, C$_1$–C$_4$ alkylthio, and C$_1$–C$_4$ alkyl optionally substituted by one or more fluorine atoms, the phenyl or pyridinyl group being optionally further substituted by one or more substituents independently selected from halogen, cyano, hydroxyl, C$_1$–C$_4$ alkylthio, C$_1$–C$_4$ alkyl-NH—, NHR$^{13}$—C$_1$–C$_4$ alkyl-, C$_1$–C$_4$ alkyl-SO$_2$—, C$_1$–C$_4$ alkyl-SO$_2$NH—, C$_1$–C$_4$ alkyl-NHSO$_2$—, C$_1$–C$_4$ alkyl-C(O)NH—, C$_1$–C$_4$ alkyl-NHC(O)—, -D-G, C$_1$–C$_4$ alkoxy optionally substituted by —NR$^{14}$R$^{15}$ or by R$^{16}$, and C$_1$–C$_4$ alkyl optionally substituted by one or more fluorine atoms or by one or more hydroxyl groups, or R$^4$ represents a 9- or 10-membered unsaturated bicyclic ring system selected from naphthyl, benzimidazolyl, quinolinyl, indolinyl, isoquinolinyl, benzofuranyl, isobenzofuranyl, benzothienyl, indolyl, isoindolyl, benzthiazolyl and benzoxazolyl, the bicyclic ring system being optionally substituted by one or more substituents independently selected from halogen, oxo, C$_1$–C$_4$ alkyl, C$_1$–C$_4$ alkoxy, C$_1$–C$_4$ alkylthio and —NR$^{10}$R$^{11}$;

D represents an oxygen atom or a group (CH$_2$)$_n$ or CH$_2$NH;

n is 1,2 or 3;

G represents a piperazinyl, morpholinyl or 2,5-diazabicyclo[2.2.1]heptyl group, or G represents a piperazinyl group optionally substituted by amino;

R$^5$ represents a hydrogen atom, or a hydroxyl or C$_1$–C$_4$ alkoxy group;

R$^6$ represents a hydrogen atom, or a cyano, nitro, hydroxyl, C$_1$–C$_4$ alkyl or C$_1$–C$_4$ alkoxy group;

R$^7$, R$^8$ and R$^9$ each independently represent a hydrogen atom or a C$_1$–C$_4$ alkyl group;

R$^{10}$ and R$^{11}$ each independently represent a hydrogen atom or a C$_1$–C$_4$ alkyl group, or R$^{10}$ and R$^{11}$ together with the nitrogen atom to which they are attached form a 5- or 6-membered saturated heterocyclic ring comprising one or two ring nitrogen atoms;

R$^{12}$ represents a hydrogen atom, or a C$_1$–C$_4$ alkyl group optionally substituted by amino;

R$^{13}$ represents a hydrogen atom, or a C$_1$–C$_4$ alkyl group optionally substituted by hydroxyl;

R$^{14}$ and R$^{15}$ each independently represent a hydrogen atom or a C$_1$–C$_4$ alkyl group optionally substituted by hydroxyl, or R$^{14}$ and R$^{15}$ together with the nitrogen atom to which they are attached form a 5- or 6-membered saturated heterocyclic ring comprising one or two ring nitrogen atoms; and R$^{16}$ represents a 1-(C$_1$–C$_4$-alkyl)-piperidinyl group;

with the proviso that when m is 0, X is N and Y is O, then R$^4$ does not represent 2-benzothiazolyl;

or a pharmaceutically acceptable salt thereof.

2. A compound according to claim 1, wherein X represents a nitrogen atom.

3. A compound according to claim 1, wherein Y represents an oxygen atom.

4. A compound according to claim 1, wherein, in R$^3$, the 5- to 10-membered unsaturated ring system is selected from phenyl, pyridinyl, pyrimidinyl, naphthyl, furanyl, pyrryl, thienyl, isothiazolyl, imidazolyl, benzimidazolyl, tetrazolyl, pyrazinyl, quinolinyl, isoquinolinyl, benzofuranyl, isobenzofuranyl, benzothienyl, pyrazolyl, indolyl, isoindolyl, purinyl, oxazolyl, isoxazolyl, thiazolyl, triazinyl, benzothiazolyl, benzooxazolyl, imidazopyrazinyl, triazolopyrazinyl, naphthyridinyl, furopyridinyl, thiopyranopyrimidinyl, pyridazinyl, quinazolinyl, pteridinyl, triazolopyrimidinyl, triazolopyrazinyl, thiapurinyl, oxapurinyl, deazapurinyl, thiazolopyrimidinyl, indolinyl, benzooxadiazolyl, benzothiadiazolyl, tetrahydroisoquinilinyl, 2-(isoxazol-3-yl)thienyl, and thienopyrimidinyl.

5. A compound according to claim 1, wherein, in $R^3$, the ring system is optionally substituted by one or more substituents independently selected from methyl, amino, cyano, methoxy, chloro, nitro, $NH_2C(O)—$, $CH_3C(O)NH—$, $CH_3SO_2—$, $CH_3SO_2NH—$ and $NH_2CH_2CH_2NHC(O)—$.

6. A compound according to claim 1, wherein, in $R^4$, an ortho substituent in the phenyl or pyridinyl group is halogen or $C_1$–$C_4$ alkyl optionally substituted by one or more fluorine atoms.

7. A compound of formula (I) or a pharmaceutically acceptable salt thereof as defined in claim 1 which is selected from:

(+)-N-(2,6-Dimethylphenyl)-2-(3-methyl-4-(thieno[2,3-d]pyrimidin-4-yl)piperazin-1-yl)acetamide, cis-[2-(3,5-Dimethyl-4-(thieno[2,3-d]pyrimidin-4-yl)piperazin-1-yl)]-N-(2,6-dimethylphenyl)acetamide, (+)-2-[3-Methyl-4-(4-methylphenyl)piperazin-1-yl]-N-(2,6-dimethylphenyl)acetamide, cis-N-[3-Hydroxymethyl-2-methylphenyl]-2-(3,5-dimethyl-4-(thieno[2,3-d]pyrimidin-4-yl)piperazin-1-yl)acetamide, (R)-2-[4-(1-Methylimidazol-4-sulphonyl-4-yl)-3-ethylpiperazin-1-yl]-N-(quinolin-5-yl)acetamide, cis-2-[3,5-Dimethyl-4-(thieno[2,3-d]pyrimidin-4-yl)piperazin-1-yl]-N-(2-methylphenyl)acetamide, cis-N-(2-Chlorophenyl)-2-[3,5-dimethyl-4-(thieno[2,3-d]pyrimidin-4yl)piperazin-1-yl]acetamide, cis-N-(2-Chlorophenyl)-2-[3,5-dimethyl-4-(9-methyl-9H-purin-6yl)piperazin-1-yl]acetamide, cis-2-(3,5-Dimethyl-4-(thieno[2,3-d]pyrimidin-4-yl)piperazin-1-yl)-N-(isoquinolin-5-yl)acetamide, cis-2-(3,5-Dimethyl-4-thieno[2,3-d]pyrimidin-4-yl)piperazin-1-yl)-N-(quinolin-5-yl)acetamide, cis-2-(3,5-Dimethyl-4-(thieno[2,3-d]pyrimidin-4-yl)piperazin-1-yl)-N-(2-methyl-5-methylsulphonamidophenyl)acetamide, cis-2-(3,5-Dimethyl-4-(thieno[2,3-d]pyrimidin-4-yl)piperazin-1-yl)-N-(2-trifluoromethylphenyl)acetamide, cis-2-(3,5-Dimethyl-4-(thieno[2,3-d]pyrimidin-4-yl)piperazin-1-yl)-N-(3-methylpyridin-2-yl)acetamide, cis-2-(3,5-Dimethyl-4-(thieno[2,3-d]pyrimidin-4-yl)piperazin-1-yl)-N-(isoquinolin-1-yl)acetamide, cis-4-(4-Amino-5-cyanopyrimidin-2-yl)-3,5-dimethylpiperazin-1-yl)-N-(2-chlorophenyl)acetamide, cis-2-(4-Benzenesulphonyl-3,5-dimethylpiperazin-1-yl)-N-(2-chloro-phenyl)acetamide, (+)-N-(2,6-Dimethylphenyl)-2-[(3methy-4-thiazolo(5,4-d)pyrimidin-7-yl)piperazin-1-yl]acetamide, cis-N-(2-Chlorophenyl)-2-[(3,5-dimethyl-4-quinazolin-4-yl)piperazin-1-yl]acetamide, N-(2-Chloropbenyl)-2-[(8-(thieno[2,3-d]pyrimidin-4-yl)-3,8-diazabicyclo[3.2.1]oct-3-yl]acetamide, N-(2-Methylphenyl)-2-[8-(9-methyl-9H-purin-4yl)-3,8-diazabicyclo[3.2.1]oct-3-yl]acetamide, 2-[8-(9-Methyl-9H-purin-6-yl)-3,8-diazabicyclo[3.2.1]oct-3-yl]-N-(quinolin-5-yl)acetamide, N-(Quinolin-5-yl)-2-[8-thiazolo[5,4-d]pyrimidin-7-yl)-3,8-diazabicyclo[3.2.1]oct-3-yl]acetamide, N-(2-Methylphenyl)-2-[(8-thiazolo[5,4-d]pyimidin-7-yl)-3,8-diazabicyclo[3.2.1]oct-3-yl]acetamide, N-(2-Methyl-5-(methylsulphonyl)amidophenyl)-2-[8-(9methyl-9H-purin-6-yl)-3,8-diazabicyclo[3.2.]oct-3-yl]acetamide, N-[2-Methyl-5-(methylsulphonyl)amidophenyl]-2-[(8-thiazolo[5,4-d]pyrimidin-7-yl)-3,8-diazabicyclo[3.2.1]oct-3-yl]acetamide, N-[2-Methyl-5-(methylsulphonyl)amidophenyl]-2-[4-(thieno[2,3d]pyrimidin-4-yl)-3,8-diazabicyclo[3.2.]oct-3-yl]acetamide, cis-2-(3,5-Dimethyl-4-(thieno[2,3-d]pyrimidin-4-yl)piperazin-1-yl)-N-(2-methyl-5-(1-piperazinylmethyl)phenyl)acetamide, hydrochloride salt, N-(2-Methylphenyl)-2-[(8-(thieno[2,3-d]pyrimidin-4-yl)-3,8-diazabicyclo[3.2.1]oct-3-yl]acetamide, N-[5-(Methanesulphonylamido-2-methylphenyl)-2[8-(thieno[2,3d]pyrimidin-4-yl)-8-azabicyclo[3.2.1]oct-3-yl]acetamide, N-(2-Methyl-5-(1-piperazinylmethyl)phenyl)-2-[(8-(thieno[2,3d]pyrimidin-4yl)-3,8-diazabicyclo[3.2.1]oct-3-yl]acetamide, cis-N-(5-(2-Aminoethoxy)-2-methy-phenyl)-2-(3,5-dimethyl-4-(thieno[2,3-d[pyrimidin-4-yl)piperazin-1-yl)acetamide, hydrochloride salt, cis-N-(5-(2-(N-Methylamino)ethoxy)-2-methyl-phenyl)-2-(3,5-dimethyl-4-(thieno[2,3-d]pyrimidin-4-yl)piperazin-1-yl)acetamide, hydrochloride salt, cis-N-(5-(2-(N-Methylamino)ethoxy)-2-methyl-phenyl)-2-(4-benzenesulphonyl)-3,5-dimethyl)piperazin-1-yl)acetamide, cis-N-[5-(2-Aminoethoxy)-2-methyl-phenyl)-2-(4-benzenesulphonyl-3,5-dimethyl)piperazin-1-yl]acetamide, hydrochloride salt, N-(2-Oxo-2,3-dihydro-1H-indol-4-yl)-2-(8-thieno[2,3-d]pyrimidin-4-yl-3,8-diazabicyclo[3.2.1]oct-3-yl)acetamide N-(3-Fluoro-2-methyl-phenyl)-2-((8quinazolin-4-yl)-3,8-diazabicyclo[3.2.1]oct-3-yl)acetamide, N-(2-Methylphenyl)-2-[8-(benzenesulphonyl)-3,8-diazabicyclo[3.2.1]oct-3-yl]acetamide, N-(3-Fluoro-2-methylphenyl)-2-[8-(benzenesulphonyl)-3,8-diazabicyclo[3.2.1]oct-3-yl]acetamide, cis-N-(3-Fluoro-2-methyl-phenyl)-2-(4-benzenesulphonyl)-3,5-dimethyl)piperain-1-yl)acetamide, N-(2-Methylphenyl)-2-[8-(3-cyanobenzenesulphonyl)-3,8-diazabicyclo[3.2.1]oct-3-yl]acetamide, 2-[8-(3-Methoxybenzenesulphonyl)-3,8-diazabicyclo[3.2.1]oct-3-yl]-N-(2-methylphenyl)acetamide, 2-[8-(Benzo[1,2,5]oxadiazole-4-sulphonyl)-3,8-diazabicyclo[3.2.]oct-3-yl]-N-(2-methylphenyl)acetamide, 2-[8-(Benzo[1,2,5]thiadiazole-4-sulphonyl)-3,8-diazabicyclo[3.2.1]oct-3-yl]-N-(2-methylphenyl)acetamide, 2-[8-(5-Chlorothieno-2-yl)sulphonyl)-3,8-diazabicyclo[3.2.1]oct-3-yl]-N-(2-methylphenyl)acetamide, 2-[8-(2-Chlorobenzenesulphonyl)-3,8-diazabicyclo[3.2.1]oct-3-yl]-N-(2-methylphenyl)acetamide, 2-[8-(5-Chloro-2-methoxybenzenesulphonyl)-3,8-diazabicyclo[3.2.1]oct-3-yl]-N-(2-methylphenyl)acetamide, 2-[8-(4-Acetylaminomethoxybenzenesulphonyl)-3,8-diazabicyclo[3.2.1]oct-3-yl]-N-(2-methylphenyl)acetamide, N-(2-Methylphenyl)-2-[(8-(3-methylthieno[2,3-d]pyrimidin-4-yl)-3,8-diazabicyclo[3.2.1]oct-3-yl]acetamide, cis-2-(3,5-Dimethyl-4-(thieno[2,3-d]pyrimidin-4-yl)piperazin-1-yl)-N-(1-methyl-1H-benzoimidazol-2-yl)acetamide, cis-2-(3,5-Dimethyl-4-(thieno[2,3-d]pyrimidin-4-yl)piperazin-1-yl)-N-(2-methyl-5-(4-piperidinyloxy)phenyl)acetamide, hydrochloride salt, cis-2-(3,5-Dimethyl-4-benzenesulphonyl)piperazin-1-yl)-N-(2-methyl-5-(4-piperidinyloxy)phenyl)acetamide, cis-2-(3,5-Dimethyl-4-(quinazolin-4-yl)piperazin-1-yl)-N-(2-methyl-5-(4-piperidinyloxy)phenyl)acetamide, cis-2-(3,5-Dimethyl-4-(4-quinazolinyl)piperazin-1-yl)-N-(2-methyl-5-(piperazin-4-yl-methyl)phenyl)acetamide, cis-2-(3,5-Dimethyl-4-(4-quinazolinyl)piperazin-1-yl)-N-(2-methyl-5-(2-(N-methylamino)ethoxy)phenyl)acetamide, cis-2-[4-(3-Cyanobenzenesulphonyl)-3,5-dimethylpiperazin-1-yl]-N-(2-methylpheriyl)acetamide, cis-N-(2-Methylphenyl)-2-[4-(3-nitrobenzenesulphonyl)-3,5-dimethylpiperazin-1-yl]-acetamide, cis-2-[4-(3-Aminobenzenesulphonyl)-3,5-dimethylpiperazin-1-yl]-N-(2-methylphenyl)acetamide, cis-2-(3,5-Dimethyl-4-(3-cyanobenzenesulphonyl)piperazin-1-yl)-N-(quinolin-5-yl)acetamide, cis-2-(3,5-Dimethyl-4-(4-cyanobenzenesulphonyl)piperazin-1-yl)-N-(quinolin-5-yl)acetamide, cis-2-(4-(3-Cyanobenzenesulphonyl)-3,5-dimethylpiperazin-1-yl)-N-(3-fluoro-2-methylphenyl)acetamide, cis-2-(4-(4-Cyanobenzenesulphonyl)-3,5-dimethylpiperazin-1-yl)-N-(3-fluoro-2-methylphenyl)acetamide, cis-2-[4-(3-Acetylaminobenzenesulphonyl)-3,5-dimethylpiperazin-1-yl]-N-(2-methylphenyl)acetamide, cis-2-[4-(3-Aminocarbonylbenzenesulphonyl)-3,5-dimethylpiperazin-1-yl]-N-(2-methylphenyl)acetamide, cis-2-[4-(3-Methanesulphonylaminobenzenesulphonyl)-3,5dimethylpiperazin-1-yl]-N-(2-methylphenyl)acetamide cis-2-[4-(2-Methanesulphonylbenzenesulphonyl)-3,5-dimethylpiperazin-1-yl]-N-(3-methoxy-2-methylphenyl)acetamide, cis-2-[4-(2-Methanesulphonylbenzenesulphonyl)-3,5-dimethylpiperazn-1-yl]-N-(3-fluoro-2-methylphenyl)acetamide, cis-2-[4-(1-Methylimidazol-4-sulphonyl-4-yl)-3,5-dimethylpiperazin-1-yl]-N-(quinolin-5-yl)acetamide, cis-2-[4-(1-Methylimidazol-4-sulphonyl-4-yl)-3,5-dimethylpiperazin-1-yl]-N-(3-methoxy-2-methylphenyl)acetamide, cis-2-[4-(1-Methylimidazol-4-sulphonyl-4-yl)-3,5dimethylpiperazin-1-yl]-N-(3-fluoro-2-methylphenyl)acetamide, cis-2-[4-(3-Methanesulphonylbenzenesulphonyl)-3,5-dimethylpiperazin-1-yl]-N-(2-trifluoromethyphenyl)acetamide, cis-2-[4-(2-Aminoethylaminocarbonylbenzenesulphonyl)-3,5-dimethylpiperazin-1-yl]-N-(2-methylphenyl)acetamide, cis-2-[4-(1,1,2,2-Tetrahydroisoquinilin-7-sulphonyl-7-yl)-3,5-dimethylpiperazin-1-yl]-N-(2,6-dimethylphenyl)acetamide, cis-2-[4-(3-Cyanobenzenesulphonyl)-3,5-dimethylpiperazin-1-yl]-N-(2,6-dimethylphenyl)acetamide, cis-2-[4-(4-Cyanobenzenesulphonyl)-3,5-dimethylpiperazin-1-yl]-N-(2-methylphenyl)acetamide, cis-2-[4-(2-Cyanobenzenesulphonyl)-3,5-dimethylpiperazin-1-yl]-N-(2,6-dimethyphenyl)acetamide, hydrochloride salt, cis-2-[4-(3-Cyanobenzenesulphonyl)-3,5-dimethylpiperazin-1-yl]-N-(2-chlorophenyl)acetamide, 2-[8-(Isquinolin-1-yl)-3,8-diazabicyclo[3.2.1]oct-3-y]-N-(2-methylphenyl)acetamide, cis-2-[4-(4-Acetamidobenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(2-trifluoromethylphenyl)acetamide, cis-2-[4-(3-Cyanobenzenesulphonyl)-3,5-dimethylpiperazin-1-yl]-N-(2-methyl-5-methanesulphonamidophenyl)acetamide, 2-[8-(4-Benzenesulphonyl)-3,8-diazabicyclo[3.2.1]oct-3-yl]-N-(2-methylphenyl)acetamide, 2-[8-(2-Benzenesulphonyl)-3,8-diazabicyclo[3.2.1]oct-3-yl]-N-(2-methylphenyl)acetamide, cis-2-[4-(1,2-Dimethylimidazol-4-sulphonyl-4-yl)-3,5-dimethylpiperazin-1-yl]-N-(quinolin-5-yl)acetamide, cis-2-[4-(5-Chloro-1,3-dimethylpyrazole-4-sulphonyl-4-yl)-3,5-dimethylpiperazin-1-yl]-N-(3-methoxy-2-methylphenyl)acetamide, 2-[8-(2-(Isoxazol-3-yl)thiophen-5-yl)-3,8-diazabicyclo[3.2.1]oct-3-yl]-N-(2-methylphenyl)acetamide, 2-[8-(1,1,2,2-Tetrahydroisoquinilin-7-sulphonyl)-3,8-diazabicyclo[3.2.1]oct-3-yl]-N-(2-methylphenyl)acetamide, cis-2-[4-(5-Chloro-1,3-dimethylpyrazole-4-sulphonyl-4-yl)-3,5-dimethylpiperazin-1-yl]-N-(2-methylphenyl)acetamide, cis-2-[4-(3,5-Dimethylisoxazole-4-sulphonyl-4-yl)-3,5-dimethylpiperazin-1-yl]-N-(2-methylphenyl)acetamide, cis-2-[4-(2-Methanesulphonylbenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(3-methoxy-2-methylphenyl)acetamide, cis-2-[4-(4-Methanesulphonylbenzenesulphonyl)-3,5-dimethylpiperazin-1-yl]-N-(2-methylphenyl)acetamide, cis-2-[4-(3-Cyanobenzenesulphonyl)-3,5-dimethylpiperazin-1-yl]-N-(5-cyano-2-methylphenyl)acetamide, cis-2-[4-(3-Cyanobenzenesulphonyl)-3,5-dimethylpiperazin-1-yl]-N-(5-acetamido-2-methylphenyl)acetamide, (R)-2-[4-(4-Cyanobenzenesulphonyl)-3-methylpiperazin-1-yl]-N-(quinolin-5-yl)acetamide, (S)-2-[4-(4-Cyanobenzenesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-5-methanesulphonyl)phenyl)acetamide, cis-2-[4-(3-Cyanobenzenesulphonyl)-3,5-dimethylpiperazin-1-yl]-N-(2-methyl-5-(4-amino-1-piperidinyl)methyl)phenyl]acetamide, (R)-2-[4-(4-Methanesulphonylbenzenesulphonyl)-3-methylpiperazin-1-yl]-N-(quinolin-5-yl)acetamide, (R)-2-[4-(4-Acetamidobenzenesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-5-(1-piperazinylmethyl)phenyl)acetamide, cis-2-[4-(3-Cyanobenzenesulphonyl)-3,5-dimethylpiperazin-1-yl]-N-(2-methyl-5-(4-piperidinylamino)methyl)phenyl)acetamide, cis-2-[4-(3-Cyanobenzenesulphonyl)-3,5-dimethylpiperazin-1-yl]-N-(2-methyl-5-(1-morpholinyl)methyl)phenyl)acetamide, cis-2-[4-(3-Cyanobenzenesulphonyl)-3,5-dimethylpiperazin-1-yl]-N-(2-methyl-5-(2-hydroxyethylamino)methyl)phenyl)acetamide, cis-2-[4-(3-Cyanobenzenesulphonyl)-3,5-dimethylpiperazin-1-yl]-N-(2-methyl-5-(S,S)-(2,5-diazabicyclo[2.2.1]hept-2-yl)methyl)phenyl)acetamide, (R)-2-[4-(2-Pyridinesulphonyl)-3-methylpiperazin-1-yl]-N-(quinolin-5-yl)acetamide, cis-2-[4-(3-Cyanobenzenesulphonyl)-3,5-dimethylpiperazin-1-yl]-N-(2-methyl-3-(4-amino-1-piperidinyl)methyl)phenyl]acetamide, cis-2-[4-(3-Cyanobenzenesulphonyl)-3,5-dimethylpiperazin-1-yl]-N-(2-methyl-3-(4-piperidinylamino)methyl)phenyl)acetamide, cis-2-[4-(3-Cyanobenzenesulphonyl)-3,5-dimethylpiperazin-1-yl]-N-(2-methyl-3-(1-piperazinylmethyl)phenyl)acetamide, cis-2-[4-(3-Cyanobenzenesulphonyl)-3,5-dimethylpiperazin-1-yl]-N-(2-methyl-3-(S,S)-(2,5-diazabicyclo[2.2.1]hept-2-yl)methyl)phenyl) acetamide, cis-2-[4-(3-Cyanobenzenesulphonyl)-3,5-dimethylpiperazin-1-yl]-N-((2-methyl-3-(1-morpholinyl)methyl)phenyl)acetamide, cis-2-[4-(3-Cyanobenzenesulphonyl)-3,5-dimethylpiperazin-1-yl]-N-((2-methyl-3-(2-(1-pyrrolidinyl)ethoxy)phenyl)acetamide, (±) cis-2-[4-(3-Cyanobenzenesulphonyl)-3,5-dimethylpiperazin-1-yl]-N-((2-methyl-3-(1-methylpiperidin-3-yl)methoxy)phenyl)acetamide, cis-2-[4-(3-Cyanobenzenesulphonyl)-3,5-dimethylpiperazin-1-yl]-N-((2-methyl-4-(2-(1-pyrrolidinyl)ethoxy)phenyl)acetamide, (±) cis-2-[4-(3-Cyanobenzenesulphonyl)-3,5-dimethylpiperazin-1-yl]-N-((2-methyl-4-(1-methylpiperidin-3-yl)methoxy)phenyl)acetamide, (±) cis-2-[4-(3-Cyanobenzenesulphonyl)-3,5-dimethylpiperazin-1-yl]-N-((2-methyl-5-(1-methylpiperidin-3-yl)methoxy)phenyl)acetamide, (±) cis-2-[4-(3-Cyanobenzenesulphonyl)-3,5-dimethylpiperazin-1-yl]-N-((2-methyl-6-(1-methylpiperidin-3-yl)methoxy)phenyl)acetamide, and cis-2-[4-(1-Methylimidazol-4-sulphonyl-4-yl)-3,5-dimethylpiperazin-1-yl]-N-((2-methyl-3-(2-(1-pyrrolidinyl)ethoxy)phenyl)acetamide.

8. A pharmaceutical composition comprising a compound of formula (I), or a pharmaceutically acceptable salt thereof, as claimed in any one of claims 1 to 6 and 7 in association with a pharmaceutically acceptable adjuvant, diluent or carrier.

9. A process for the preparation of a compound of formula (I) as defined in claim 1, which comprises (a) reacting a compound of the formula

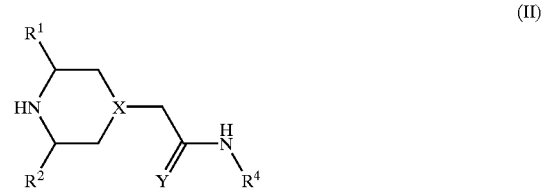

(II)

wherein X, Y, $R^1$, $R^2$ and $R^4$ are as defined in formula (I), with a compound of the formula (III), $R^3$—$(SO_2)_m$—$L^1$, wherein $L^1$ represents a leaving group and m and $R^3$ are as defined in formula (I); or (b) when X represents a nitrogen atom and Y represents an oxygen atom, reacting a compound of the formula

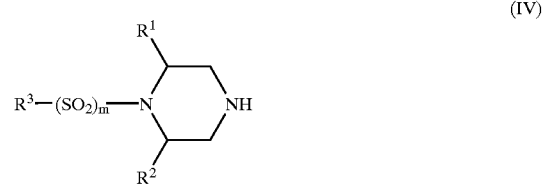

(IV)

wherein m, $R^1$, $R^2$ and $R^3$ are as defined in formula (I), with a compound of the formula

(V)

wherein $L^2$ represents a leaving group and $R^4$ is as defined in formula (I); or (c) reacting a compound of the formula

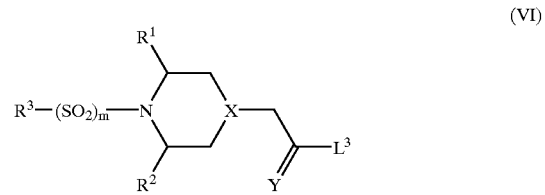

(VI)

wherein $L^3$ represents a leaving group and m, X, Y, $R^1$, $R^2$ and $R^3$ are as defined in formula (I), with a compound of the formula (VII), $H_2N$—$R^4$ wherein $R^4$ is as defined in formula (I);

and optionally after (a),(b) or (c) converting the compound of formula (I) obtained to a pharmaceutically acceptable salt thereof.

10. A process for the preparation of a pharmaceutical composition as claimed in claim 8 which comprises mixing a compound of formula (I), or a pharmaceutically acceptable salt thereof, as defined in any one of claims 1 to 8 with a pharmaceutically acceptable adjuvant, diluent or carrier.

\* \* \* \* \*